United States Patent
Di Malta et al.

(10) Patent No.: US 7,119,086 B2
(45) Date of Patent: Oct. 10, 2006

(54) PHENYLSULFONYL-1,3-DIHYDRO-2H-INDOLE-2-ONE DERIVATIVES, THEIR PREPARATION AND THEIR THERAPEUTIC USE

(75) Inventors: Alain Di Malta, Saint-Clement-de-Riviere (FR); Georges Garcia, Frontignan (FR); Richard Roux, Vailhauques (FR); Bruno Schoentjes, Rouen (FR); Claudine Serradeil-Le Gal, Escalquens (FR); Bernard Tonnerre, Vailhauques (FR); Jean Wagnon, Montpellier (FR)

(73) Assignee: Sanofi-Aventis, Paris (FR)

( * ) Notice: Subject to any disclaimer, the term of this patent is extended or adjusted under 35 U.S.C. 154(b) by 274 days.

(21) Appl. No.: 10/484,370

(22) PCT Filed: Jul. 15, 2002

(86) PCT No.: PCT/FR02/02500

§ 371 (c)(1),
(2), (4) Date: Jan. 16, 2004

(87) PCT Pub. No.: WO03/008407

PCT Pub. Date: Jan. 30, 2003

(65) Prior Publication Data

US 2004/0180878 A1 Sep. 16, 2004

(30) Foreign Application Priority Data

Jul. 17, 2001 (FR) .................................. 01 10359

(51) Int. Cl.
*A61K 31/496* (2006.01)
*A61K 31/551* (2006.01)
*C07D 401/14* (2006.01)
*C07D 417/14* (2006.01)

(52) U.S. Cl. ............ 514/218; 514/252.19; 514/252.11; 514/253.09; 514/252.02; 514/254.02; 514/254.05; 540/575; 544/238; 544/295; 544/357; 544/364; 544/369; 544/370

(58) Field of Classification Search ................ 540/575; 544/364, 357, 238, 295, 369, 370; 514/218, 514/252.19, 253.09, 252.02, 254.02, 254.05, 514/252.11
See application file for complete search history.

(56) References Cited

U.S. PATENT DOCUMENTS 5,594,023 A  1/1997  Wagnon et al.
5,773,612 A  6/1998  Wagnon et al.
2005/0070718 A1 * 3/2005  Lubisch et al. ............. 548/181

FOREIGN PATENT DOCUMENTS

GB  2 326 639  12/1998
WO  WO 95/18105  7/1995

OTHER PUBLICATIONS

Akerlund, Prog. Brain Res. vol. 139, p. 359-65 (2002) (Abstract).*
Tsatsaris et al. Drugs, vol. 64(4), p. 375-82 (2004) (Abstract).*
Paranjape et al. Expert Opinion on Investigational Drugs, vol. 10(5), p. 825-834 (2001).*
Barberis et al. Journal of Endocrinology, vol. 156, p. 223-229 (1998).*
Salam, Expert Opin.Investig. Drugs, vol. 14(5), p. 687-691 (2005).*

* cited by examiner

*Primary Examiner*—Emily Bernhardt
(74) *Attorney, Agent, or Firm*—Balaram Gupta

(57) ABSTRACT

The invention relates to compounds of formula:

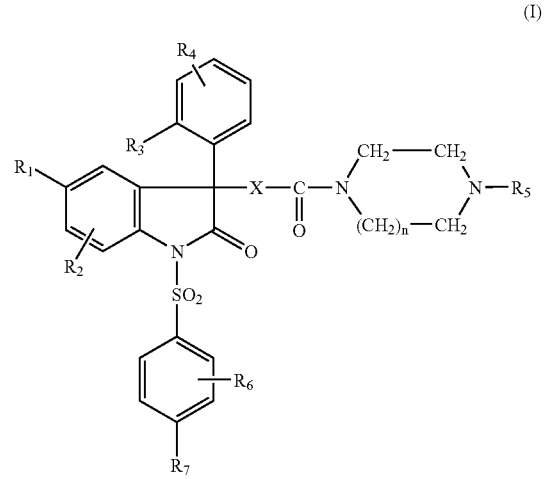

(I)

and also to the salts thereof with mineral or organic acids, and the solvates and/or hydrates thereof, with affinity for and selectivity towards the arginine-vasopressin $V_{1b}$ receptors and/or for the ocytocin receptors and, furthermore, for certain compounds, affinity for the $V_{1a}$ receptors.

The invention also relates to the process for preparing them, to the intermediate compounds of formula (IV) that are useful for preparing them, to pharmaceutical compositions containing them and to their use for preparing medicinal products.

26 Claims, No Drawings

PHENYLSULFONYL-1,3-DIHYDRO-2H-INDOLE-2-ONE DERIVATIVES, THEIR PREPARATION AND THEIR THERAPEUTIC USE

The present invention relates to 1,3-dihydro-2H-indol-2-one derivatives, to their preparation and to their therapeutic application.

The compounds according to the present invention show affinity for the arginine-vasopressin (AVP) $V_{1b}$ receptors and/or for the ocytocin (OT) receptors and, furthermore, some of them show affinity for the AVP $V_{1a}$ receptors.

AVP is a hormone which is known for its anti-diuretic effect and its effect in regulating arterial pressure. It stimulates several types of receptors: $V_1$ ($V_{1a}$, $V_{1b}$), $V_2$. These receptors are located in particular in the liver, the blood vessels (coronary, renal and cerebral vessels), the platelets, the kidneys, the uterus, the adrenal glands, the pancreas, the central nervous system and the pituitary. AVP thus exerts cardiovascular, hepatic, pancreatic, anti-diuretic and platelet-aggregating effects and effects on the central and peripheral nervous system, and on the uterus.

OT is a neurohypophyseal hormone, of cyclic nonapeptide structure similar to that of AVP. The OT receptors are found essentially on uterine smooth muscle and on the myoepithelial cells of the mammary glands. Thus, OT plays an important role in parturition since it is involved in uterine muscle contraction and in lactation. Moreover, the OT receptors are also located on other peripheral tissues and in the central nervous system; OT may thus have effects in the cardiovascular, renal, endocrine or behavioural fields.

The location of the various receptors is described in: S. Jard et al., Vasopressin and oxytocin receptors: an overview, in Progress in Endocrinology, H. Imura and K. Shizurne ed., Experta Medica, Amsterdam, 1988, 1183–1188, and in the following articles: J. Lab. Clin. Med., 1989, 114 (6), 617–632 and Pharmacol. Rev., 1991, 43 (1), 73–108.

More particularly, the AVP $V_{1a}$ receptors are located in many peripheral organs and in the brain. They have been cloned in particular in rats and man and they regulate most of the known effects of AVP: platelet aggregation; uterine contractions; blood vessel contraction; secretion of aldosterone, cortisol, CRF (corticotropin-releasing factor) and ACTH (adrenocorticotrophic hormone); hepatic glycogenolysis, cell proliferation and the main central effects of AVP (hypothermia, memory, etc.).

The $V_{1b}$ receptors were initially identified in the adenohypophysis of various animal species (rat, pig, cattle, sheep, etc.), including man (S. Jard et al., Mol. Pharmacol., 1986, 30, 171–177; Y. Arsenijevic et al., J. Endocrinol., 1994, 141, 383–391; J. Schwartz et al., Endocrinology, 1991, 129 (2), 1107–1109; Y. De Keyser et al., FEBS Letters, 1994, 356, 215–220) in which they stimulate the release of adenocorticotrophic hormone via AVP and potentiate the effects of CRF on the release of ACTH (G. E. Gillies et al., Nature, 1982, 299, 355). In the hypothalamus, the $V_{1b}$ receptors also induce a direct release of CRF (Neuroendocrinology, 1994, 60, 503–508) and are, in these various respects, involved in stress situations.

These $V_{1b}$ receptors have been cloned in rats, man and mice (Y. De Keyser, FEBS Letters, 1994, 356, 215–220; T. Sugimoto et al., J. Biol. Chem., 1994, 269 (43), 27088–27092; M. Saito et al., Biochem. Biophys. Res. Commun., 1995, 212 (6), 751–757; S. J. Lolait et al., Neurobiology, 1996, 92, 6783–6787; M. A. Ventura et al., Journal of Molecular endocrinology, 1999, 22, 251–260) and various studies (in situ hybridization, PCR (Polymerase Chain Reaction), etc.) reveal the ubiquitous presence of these receptors in various central tissues (brain, hypothalamus and adenohypophysis in particular) and peripheral tissues (kidney, pancreas, adrenal glands, heart, lungs, intestine, stomach, liver, mesentery, bladder, thymus, spleen, uterus, retina, thyroid, etc.) and in certain tumours (pituitary, pulmonary, etc. tumours) suggesting a broad biological and/or pathological role for these receptors and a potential involvement in various diseases.

By way of example, in rats, studies have shown that AVP regulates the endocrine pancreas via the $V_{1b}$ receptors, by stimulating the secretion of insulin and glucagon (B. Lee et al., Am. J. Physiol. 269 (Endocrinol. Metab. 32): E1095-E1100, 1995) or the production of catecholamines in the adrenal medulla which is the site of a local synthesis of AVP (E. Grazzini et al., Endocrinology, 1996, 137 (a), 3906–3914). Thus, in the adrenal medullary tissue, AVP via these receptors is thought to have a crucial role in certain types of adrenal pheochromocytomas secreting AVP and thereby inducing a sustained production of catecholamines which is the cause of hypertension conditions that are resistant to angiotensin II receptor antagonists and to conversion enzyme inhibitors. The adrenal cortex is also rich in $V_{1a}$ receptors involved in the production of glucocorticoids and mineralocorticoids (aldosterone and cortisol). Via these receptors, AVP (circulating or synthesized locally) may induce a production of aldosterone with an efficacy comparable to that of angiotensin II (G. Guillon et al., Endocrinology, 1995, 136 (3), 1285–1295). Cortisol is a powerful regulator of the production of ACTH, the stress hormone.

Recent studies have also shown that the adrenal glands are capable of releasing CRF and/or ACTH directly via activation of the $V_{1b}$ and/or $V_{1a}$ receptors borne by the medullary cells (G. Mazzocchi et al., Peptides, 1997, 18 (2), 191–195; E. Grazzini et al., J. Clin. Endocrinol. Metab., 1999, 84 (6), 2195–2203).

The $V_{1b}$ receptors are also considered as a marker of tumours. ACTH-secreting tumours, such as certain pituitary tumours, certain bronchial carcinomas (SCLCs (Small-Cell Lung Cancers)), pancreatic, adrenal and thyroid carcinomas, inducing Cushing's syndrome in certain cases (J. Bertherat et al., Eur. J. Endocrinol., 1996, 135, 173; G. A. Wittert et al., Lancet, 1990, 335, 991–994; G. Dickstein et al., J. Clin. Endocrinol. Metab., 1996, 81 (8), 2934–2941) overexpress the $V_{1b}$ receptors. As regards the $V_{1a}$ receptors, these are a marker more specific for small-cell lung cancers (SCLCs) (P. J. Woll et al., Biochem. Biophys. Res. Commun., 1989, 164 (1), 66–73). Thus, the compounds according to the present invention are obvious diagnostic tools and offer a novel therapeutic approach in the proliferation and detection of these tumours, even at an early stage (radiolabelling; SPECT (Single Photon Emission Computed Tomography); PET Scan (Positron Emission Tomography Scanner)).

The abundant presence of the $V_{1b}$ receptor messenger in the stomach and intestine suggests an involvement of AVP via this receptor on the release of gastrointestinal hormones such as cholecystokinin, gastrin or secretin (T. Sugimoto et al., Molecular cloning and functional expression of $V_{1b}$ receptor gene, in Neurohypophysis: Recent Progress of Vasopressin and Oxytocin Research; T. Saito, K. Kurokawa and S. Yoshida ed., Elvesier Science, 1995, 409–413).

1,3-Dihydro-2H-indol-2-one derivatives have been disclosed in certain patent applications as ligands of the arginine-vasopressin receptors and/or the Ocytocin receptors: mention may be made of patent applications WO 93/15051, EP 636 608, EP 636 609, WO 95/18105, WO 97/15556 and WO 98/25901.

Novel 1,3-dihydro-2H-indol-2-one derivatives have now been found, which show affinity for and selectivity towards the arginine-vasopressin $V_{1b}$ receptors and/or the ocytocin receptors and, furthermore, some of them show affinity for the $V_{1a}$ receptors. These derivatives show no affinity for the AVP $V_2$ receptors.

Thus, according to one of its aspects, one subject of the present invention is compounds of formula:

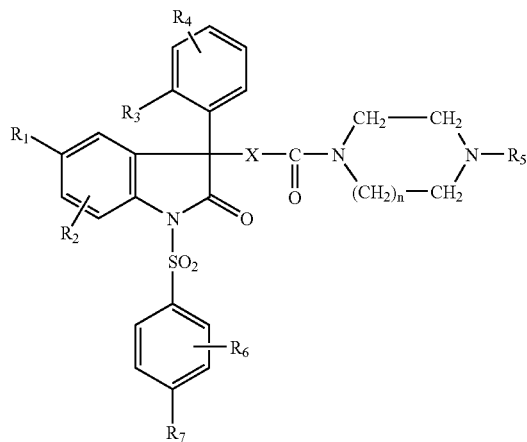

(I)

in which:
n is 1 or 2;
X represents a group —CH$_2$—; —O—; —NH—; —O—CH$_2$—; —NH—CH$_2$—; —NH—CH$_2$—CH$_2$—;
R$_1$ represents a halogen atom; a (C$_1$–C$_4$)alkyl; a (C$_1$–C$_4$) alkoxy;
R$_2$ represents a hydrogen atom; a halogen atom; a (C$_1$–C$_4$) alkyl; a (C$_1$–C$_4$)alkoxy; a trifluoromethyl radical;
R$_3$ represents a halogen atom; a (C$_1$–C$_3$)alkyl; a (C$_1$–C$_3$) alkoxy; a trifluoromethyl radical; a trifluoromethoxy radical;
R$_4$ represents a hydrogen atom; a halogen atom; a (C$_1$–C$_3$) alkyl; a (C$_1$–C$_3$)alkoxy;
R$_5$ represents a radical chosen from:

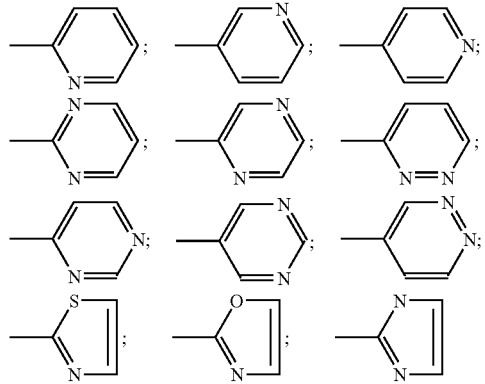

R$_6$ represents a (C$_1$–C$_4$)alkoxy;
R$_7$ represents a (C$_1$–C$_4$)alkoxy;

and also the salts thereof with mineral or organic acids, the solvates thereof and/or the hydrates thereof.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of addition salts with acids. Such addition salts form part of the invention.

The salts are advantageously prepared with pharmaceutically acceptable acids, but salts of other acids that are useful for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

The term "halogen" means a chlorine, bromine, fluorine or iodine atom.

The term "alkyl" means a linear or branched alkyl radical of one to three carbon atoms or of one to four carbon atoms, such as a methyl, ethyl, propyl, isopropyl, butyl, isobutyl, sec-butyl or tert-butyl radical.

The term "alkoxy" means a linear or branched alkoxy radical of one to three carbon atoms or of one to four carbon atoms, such as a methoxy, ethoxy, propoxy, isopropoxy, butoxy, isobutoxy, sec-butoxy or tert-butoxy radical.

Advantageously, the invention relates to compounds of formula (I) in which R$_5$ represents a radical chosen from:

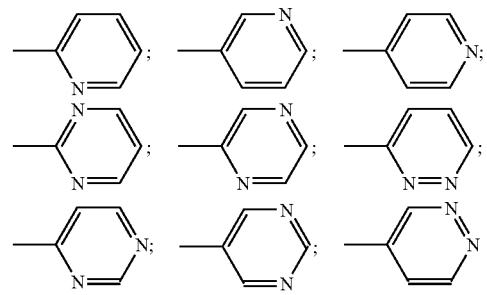

According to the present invention, the compounds of formula (I) that are preferred are those in which R$_1$ represents a chlorine atom or a methyl radical.

According to the present invention, the compounds of formula (I) that are preferred are those in which R$_2$ represents a hydrogen atom, a chlorine atom, a methyl radical, a methoxy radical or a trifluoromethyl radical.

According to the present invention, the compounds of formula (I) that are preferred are those in which R$_3$ represents a chlorine atom, a fluorine atom, a methoxy radical, an ethoxy radical, an isopropoxy radical, a trifluoromethoxy radical or a trifluoromethyl radical.

According to the present invention, the compounds of formula (I) that are preferred are those in which R$_4$ represents a hydrogen atom or a methoxy radical.

According to the present invention, the compounds of formula (I) that are preferred are those in which R$_5$ represents a 2-pyridyl, a 3-pyridyl, a 4-pyridyl, a 2-pyrimidinyl, a 2-pyrazinyl, a 3-pyridazinyl or a 1,3-thiazol-2-yl.

According to the present invention, the compounds of formula (I) that are preferred are those in which R$_6$ is in position –2 of the phenyl and represents a methoxy radical.

According to the present invention, the compounds of formula (I) that are preferred are those in which $R_7$ represents a methoxy radical.

Particularly, the compounds of formula (I) that are preferred are those in which:

n and X are as defined for a compound of formula (I);
$R_1$ represents a chlorine atom or a methyl radical;
$R_2$ represents a hydrogen atom or is in position −4 or −6 of the indol-2-one and represents a chlorine atom, a methyl radical, a methoxy radical or a trifluoromethyl radical;
$R_3$ represents a chlorine atom, a fluorine atom, a methoxy radical, an ethoxy radical, an isopropoxy radical, a trifluoromethyl radical or a trifluoromethoxy radical;
$R_4$ represents a hydrogen atom or a methoxy radical;
$R_5$ represents a 2-pyridyl, a 3-pyridyl, a 4-pyridyl, a 2-pyrimidinyl, a 2-pyrazinyl, a 3-pyridazinyl or a 1,3-thiazol-2-yl;
$R_6$ is in position −2 of the phenyl and represents a methoxy radical;
$R_7$ represents a methoxy radical;

and also the salts thereof with mineral or organic acids, and the solvates and/or hydrates thereof.

More particularly, the compounds of formula (I) that are preferred are those in which:
n is 1 or 2;
X represents a group —CH$_2$—; —O—; —NH—;
$R_1$ represents a chlorine atom;
$R_2$ represents a hydrogen atom;
$R_3$ represents a methoxy radical, an ethoxy radical or an isopropoxy radical;
$R_4$ represents a hydrogen atom;
$R_5$ represents a radical chosen from:

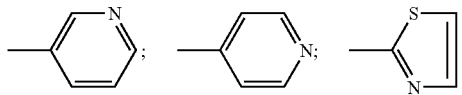

$R_6$ is in position −2 of the phenyl and represents a methoxy radical;
$R_7$ represents a methoxy radical;

and also the salts thereof with mineral or organic acids, and the solvates and/or hydrates thereof.

More particularly also, the compounds of formula (I) that are preferred are those in which:
n is 1;
X represents a group —CH$_2$—; —O—; —NH—;
$R_1$ represents a chlorine atom or a methyl radical;
$R_2$ represents a hydrogen atom or is in position −4 or −6 of the indol-2-one and represents a chlorine atom; a methyl radical; a methoxy radical;
$R_3$ represents a chlorine atom, a fluorine atom or a methoxy radical;
$R_4$ represents a hydrogen atom;
$R_5$ represents a radical chosen from:

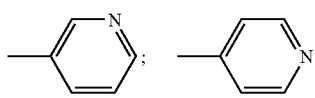

$R_6$ is in position −2 of the phenyl and represents a methoxy radical;
$R_7$ represents a methoxy radical;

and also the salts thereof with mineral or organic acids, and the solvates and/or hydrates thereof.

Finally, more particularly, the compounds of formula (I) that are preferred are those in which:
n is 1;
X represents a group —O—; —NH—; —NH—CH$_2$—CH$_2$—;
$R_1$ represents a chlorine atom;
$R_2$ represents a hydrogen atom;
$R_3$ represents a chlorine atom or a methoxy radical;
$R_4$ represents a hydrogen atom;
$R_5$ represents a radical

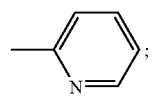

$R_6$ is in position −2 of the phenyl and represents a methoxy radical;
$R_7$ represents a methoxy radical;

and also the salts thereof with mineral or organic acids, and the solvates and/or hydrates thereof.

The following compounds:
5-chloro-3-(2-ethoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one;
5-chloro-3-(2-isopropoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one;
5-chloro-1-[(2,4-dimethoxyphenyl)sulphonyl]-3-(2-methoxyphenyl)-2-oxo-2,3-dihydro-1H-indol-3-yl 4-(2-pyridyl)-1-piperazinecarboxylate;
5-chloro-1-[(2,4-dimethoxyphenyl)sulphonyl]-3-(2-isopropoxyphenyl)-2-oxo-2,3-dihydro-1H-indol-3-yl 4-(4-pyridyl)-1-piperazinecarboxylate;
N-[5-chloro-1-[(2,4-dimethoxyphenyl)sulphonyl]-3-(2-methoxyphenyl)-2-oxo-2,3-dihydro-1H-indol-3-yl]-4-(4-pyridyl)homopiperazine-1-carboxamide;
N-[5-chloro-1-[(2,4-dimethoxyphenyl)sulphonyl]-3-(2-isopropoxyphenyl)-2-oxo-2,3-dihydro-1H-indol-3-yl]-4-(3-pyridyl)piperazine-1-carboxamide;
N-[5-chloro-1-[(2,4-dimethoxyphenyl)sulphonyl]-3-(2-isopropoxyphenyl)-2-oxo-2,3-dihydro-1H-indol-3-yl]-4-(4-pyridyl)piperazine-1-carboxamide;
5-chloro-1-[(2,4-dimethoxyphenyl)sulphonyl]-3-(2-methoxyphenyl)-3-[[3-oxo-3-[4-(2-pyridyl)-1-piperazinyl]propyl]amino]-1,3-dihydro-2H-indol-2-one;
5,6-dichloro-1-[(2,4-dimethoxyphenyl)sulphonyl]-3-(2-methoxyphenyl)-3-[2-oxo-2-[4-(4-pyridyl)-1-piperazinyl]ethyl]-1,3-dihydro-2H-indol-2-one;
5-chloro-1-[(2,4-dimethoxyphenyl)sulphonyl]-3-(2-methoxyphenyl)-6-methyl-3-[2-oxo-2-[4-(4-pyridyl)-1-piperazinyl]ethyl]-1,3-dihydro-2H-indol-2-one;
5-chloro-1-[(2,4-dimethoxyphenyl)sulphonyl]-3-(2-methoxyphenyl)-6-methyl-2-oxo-2,3-dihydro-1H-indol-3-yl 4-(4-pyridyl)-1-piperazinecarboxylate;
5-chloro-1-[(2,4-dimethoxyphenyl)sulphonyl]-6-methoxy-3-(2-methoxyphenyl)-2-oxo-2,3-dihydro-1H-indol-3-yl 4-(4-pyridyl)-1-piperazinecarboxylate;
N-[5-chloro-3-(2-chlorophenyl)-1-[(2,4-dimethoxyphenyl)sulphonyl]-2-oxo-2,3-dihydro-1H-indol-3-yl]-4-(2-pyridyl)piperazine-1-carboxamide;

N-[5-chloro-1-[(2,4-dimethoxyphenyl)sulphonyl]-3-(2-methoxyphenyl)-6-methyl-2-oxo-2,3-dihydro-1H-indol-3-yl]-4-(4-pyridyl)piperazine-1-carboxamide;

N-[6-chloro-3-(2-chlorophenyl)-1-[(2,4-dimethoxyphenyl)sulphonyl]-5-methyl-2-oxo-2,3-dihydro-1H-indol-3-yl]-4-(4-pyridyl)piperazine-1-carboxamide;

5-chloro-1-[(2,4-dimethoxyphenyl)sulphonyl]-3-(2-fluorophenyl)-3-[2-oxo-2-[4-(4-pyridyl)-1-piperazinyl]ethyl]-1,3-dihydro-2H-indol-2-one;

5,6-dichloro-1-[(2,4-dimethoxyphenyl)sulphonyl]-3-(2-fluorophenyl)-3-[2-oxo-2-[4-(4-pyridyl)-1-piperazinyl]ethyl]-1,3-dihydro-2H-indol-2-one;

5-chloro-3-(2,3-dimethoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one;

5-chloro-1-[(2,4-dimethoxyphenyl)sulphonyl]-3-(2-ethoxyphenyl)-3-[2-oxo-2-[4-(3-pyridyl)-1-piperazinyl]ethyl]-1,3-dihydro-2H-indol-2-one;

5-chloro-1-[(2,4-dimethoxyphenyl)sulphonyl]-3-(2-isopropoxyphenyl)-3-[2-oxo-2-[4-(3-pyridyl)-1-piperazinyl]ethyl]-1,3-dihydro-2H-indol-2-one;

5-chloro-1-[(2,4-dimethoxyphenyl)sulphonyl]-3-(2-isopropoxyphenyl)-3-[2-oxo-2-[4-(4-pyridyl)-1-homopiperazine]ethyl]-1,3-dihydro-2H-indol-2-one;

5-chloro-1-[(2,4-dimethoxyphenyl)sulphonyl]-3-(2-isopropoxyphenyl)-3-[2-oxo-2-[4-(1,3-thiazol-2-yl)-1-piperazinyl]ethyl]-1,3-dihydro-2H-indol-2-one;

5-chloro-1-[(2,4-dimethoxyphenyl)sulphonyl]-3-(2-ethoxyphenyl)-2-oxo-2,3-dihydro-1H-indol-3-yl 4-(3-pyridyl)-1-piperazinecarboxylate;

5-chloro-1-[(2,4-dimethoxyphenyl)sulphonyl]-3-(2-ethoxyphenyl)-2-oxo-2,3-dihydro-1H-indol-3-yl 4-(4-pyridyl)-1-piperazinecarboxylate;

in the form of optically pure isomers or in the form of a mixture, and also the salts thereof with mineral or organic acids, and the solvates and/or hydrates thereof, are most particularly preferred.

According to another of its aspects, a subject of the present invention is a process for preparing the compounds of formula (I), characterized in that:

a compound of formula:

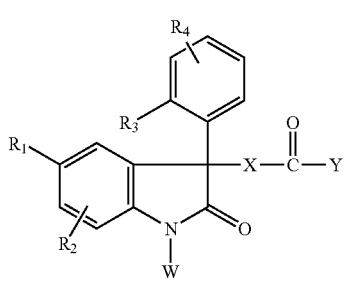

(II)

in which $R_1$, $R_2$, $R_3$, $R_4$ and X are as defined for a compound of formula (I), and:

Y represents a hydroxyl or a chlorine atom when X represents a group —CH$_2$—; —OCH$_2$—; —NH—CH$_2$—; —NH—CH$_2$—CH$_2$—;

or Y represents a phenoxy when X represents a group —O—; —NH—;

W represents a hydrogen atom when X represents a group —CH$_2$—; —OCH$_2$—;

or W represents a group

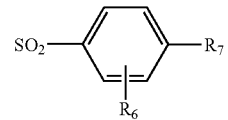

in which $R_6$ and $R_7$ are as defined for a compound of formula (I) when X represents a group —O—; —NH—; —NH—CH$_2$—; —NH—CH$_2$—CH$_2$—;

is reacted with a compound of formula:

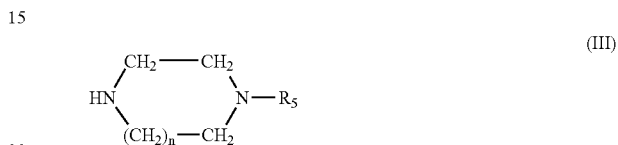

(III)

in which n and $R_5$ are as defined for a compound of formula (I);

when W represents a group

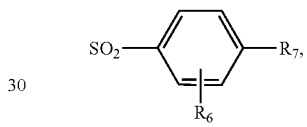

to give the expected compound of formula (I);

or, when W represents a hydrogen atom, the compound thus obtained of formula:

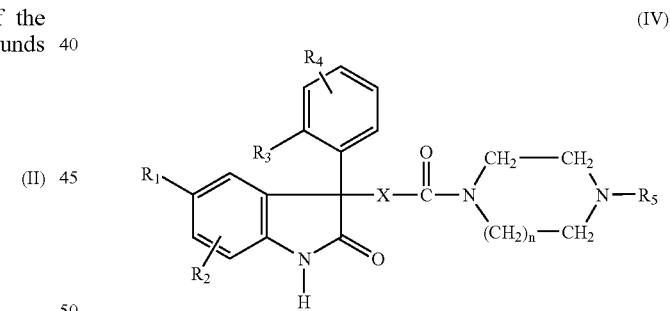

(IV)

is reacted, in the presence of a base, with a sulphonyl halide of formula:

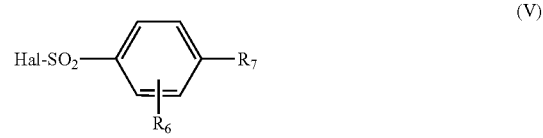

(V)

in which $R_6$ and $R_7$ are as defined for a compound of formula (I) and Hal represents a halogen atom.

Optionally, the compound of formula (I) is converted into a salt thereof with mineral or organic acids.

When Y represents a hydroxyl, the reaction of the compound of formula (II) with the compound of formula (III) is carried out in the presence of a coupling agent used in peptide chemistry, such as benzotriazol-1-yloxytris(dimethylamino)phosphonium hexafluorophosphate or benzotriazol-1-yloxytripyrrolidinophosphonium hexafluorophosphate and in the presence of a base such as triethylamine or N,N-diisopropylethylamine, in a solvent such as dichloromethane or N,N-dimethylformamide, at a temperature of between 0° C. and room temperature.

When Y represents a chlorine atom, the reaction of compound (II) with compound (III) is carried out in the absence or presence of a base such as triethylamine or N,N-diisopropylethylamine, in a solvent such as dichloromethane or chloroform and at a temperature of between −60° C. and room temperature. In the absence of base, an excess of compound (III) is used.

When Y represents a phenoxy, the reaction of compound (II) with compound (III) is carried out in a solvent such as dichloromethane, chloroform or tetrahydrofuran or a mixture of these solvents and at a temperature of between room temperature and the reflux temperature of the solvent.

This thus gives directly either a compound of formula (I) or a compound of formula (IV). The reaction of compound (IV) with the sulphonyl halide (V) is carried out in the presence of a strong base, for instance a metal hydride such as sodium hydride or an alkali metal alkoxide such as potassium tert-butoxide, in a solvent such as N,N-dimethylformamide or tetrahydrofuran and at a temperature of between −70° C. and room temperature. The reaction is preferably carried out using a compound of formula (V) in which Hal represents a chlorine atom.

The compounds of formula (I) thus obtained may be subsequently separated from the reaction medium and purified according to the standard methods, for example by crystallization or chromatography.

The compounds of formula (I) thus obtained are isolated in free base or salt form, according to the standard techniques.

The compounds of formula (II) are prepared according to various operating modes.

The compounds of formula (II) in which —X— represents a —CH$_2$— group, Y represents a hydroxyl and W represents hydrogen are prepared according to Scheme 1 below in which R$_1$, R$_2$, R$_3$ and R$_4$ are as defined for a compound of formula (I) and Alk represents a (C$_1$–C$_2$)-alkyl.

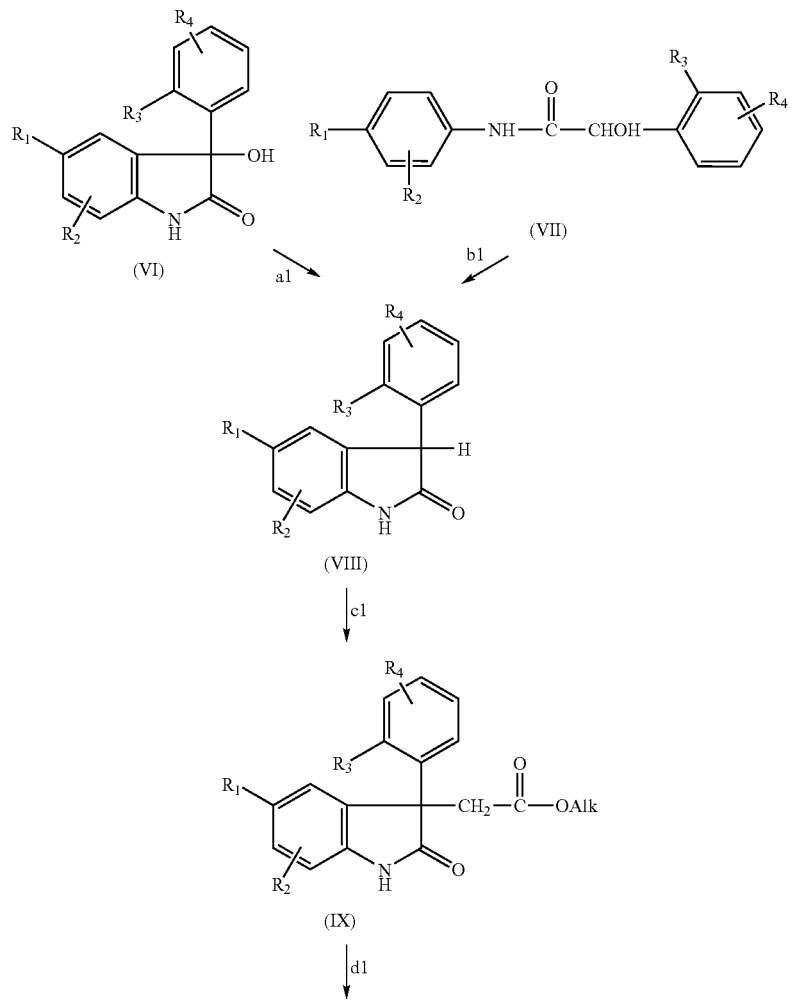

SCHEME 1

-continued

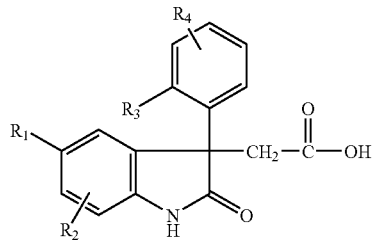

(II):

X = —CH$_2$—;  Y = —OH;  W = H;

In step a1 of Scheme 1, a compound of formula (VIII) is prepared by dehydroxylation of a corresponding compound of formula (VI) by the action of triethylsilane according to Bioorganic and Medicinal Chemistry Letters, 1997, 7 (10), 1255–1260.

A compound of formula (VIII) may also be prepared by a cyclization reaction (step b1) of a compound of formula (VII) in strong acidic medium, for example sulphuric acid or polyphosphoric acid, according to the method described in WO 95/18105 or in J. Org. Chem., 1968, 33, 1640–1643.

In step c1, the compound of formula (VIII) is reacted with a compound of formula Hal-CH$_2$COOAlk in which Hal represents a halogen atom, preferably bromine or chlorine, and Alk represents a (C$_1$–C$_2$)alkyl, in the presence of a base such as an alkali metal carbonate (for example potassium carbonate) and an alkali metal iodide (for example potassium iodide) or in the presence of a strong base such as an alkali metal hydride (for example sodium hydride), or an alkali metal alkoxide (for example sodium ethoxide), to give the compound of formula (IX). The reaction is carried out in a solvent such as acetone or N,N-dimethylformamide and at a temperature of between 0° C. and the reflux temperature of the solvent.

In step d1, the expected compound of formula (II) is obtained by hydrolysis, in alkaline medium, of the compound of formula (IX) using an alkali metal hydroxide such as sodium hydroxide, potassium hydroxide or lithium hydroxide in a solvent such as water, methanol, ethanol, tetrahydrofuran or dioxane or a mixture of these solvents, at a temperature of between 0° C. and the reflux temperature of the solvent.

The compounds of formula (VI) are known and are prepared according to known methods, such as those described in WO 95/18105.

For example, a compound of formula (VI) is prepared by reaction of a 1H-indole-2,3-dione derivative of formula:

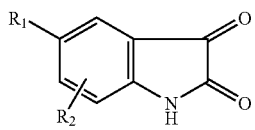
(X)

in which R$_1$ and R$_2$ are as defined for a compound of formula (I), with an organomagnesium derivative of formula:

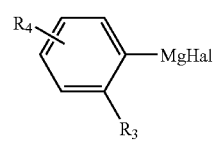
(XI)

in which R$_3$ and R$_4$ are as defined for a compound of formula (I) and Hal represents a halogen atom, preferably bromine or iodine, in a solvent such as tetrahydrofuran or diethyl ether and at a temperature of between 0° C. and the reflux temperature of the solvent.

A compound of formula (VI) in which R$_3$ is as defined for a compound of formula (I) and R$_4$, other than hydrogen, is in position −3 or −6 of the phenyl, may also be prepared by reacting a compound of formula:

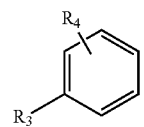
(XXXIV)

in which R$_3$ is as defined for a compound of formula (I) and R$_4$ is in position −2 or −5 of the phenyl, with a lithium derivative such as n-butyllithium, and the lithiated intermediate thus obtained is then reacted with a compound of formula (X). The reaction is carried out in a solvent such as diethyl ether, tetrahydrofuran, hexane or a mixture of these solvents, at a temperature of between −70° C. and room temperature.

The 1H-indole-2,3-dione derivatives (X) are commercially available or are prepared according to the methods described in Tetrahedron Letters, 1998, 39, 7679–7682; Tetrahedron Letters, 1994, 35, 7303–7306; J. Org. Chem., 1977, 42 (8), 1344–1348; J. Org. Chem., 1952, 17, 149–156; J. Am. Chem. Soc., 1946, 68, 2697–2703; Organic Synthèses, 1925, V, 71–74 and Advances in Heterocyclic Chemistry, A. R. Katritzky and A. J. Boulton, Academic Press, New York, 1975, 18, 2–58.

The organomagnesium derivatives (XI) are prepared according to the standard methods that are well known to those skilled in the art.

In particular, the compounds of formula (VI) in which R$_3$=(C$_1$–C$_2$)alkoxy and R$_4$=H, or R$_3$=R$_4$=(C$_1$–C$_2$)alkoxy with R$_4$ in position −3 or −6 of the phenyl, R$_2$ is other than a halogen atom and R$_1$ is as defined for a compound of formula (I), may be prepared according to the process described in Scheme 2.

SCHEME 2

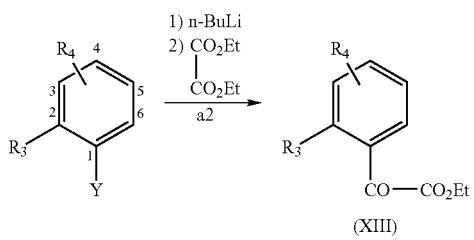

(XII): $R_3$ = ($C_1$–$C_2$)alkoxy, $R_4$ = H;
$R_3$ = $R_4$ = ($C_1$–$C_2$)alkoxy with
$R_4$ in position -3 or -6;
Y = H or Br.

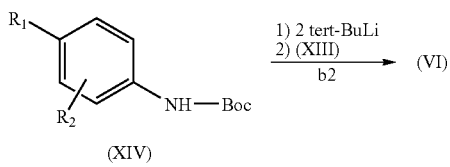

In step a2 of Scheme 2, a compound of formula (XII) is first reacted with a lithium derivative such as n-butyllithium, in the absence or presence of a base such as N,N,N',N'-tetramethylethylenediamine, and the lithiated intermediate thus obtained is then reacted with diethyl oxalate to give the compound of formula (XIII). The reaction is carried out in a solvent such as diethyl ether, tetrahydrofuran, hexane or a mixture of these solvents and at a temperature of between −70° C. and room temperature.

In step b2, a compound of formula (XIV) is first reacted with two equivalents of a lithium derivative such as tert-butyllithium, and the lithiated intermediate thus obtained is then reacted with the compound of formula (XIII) to give the expected compound of formula (VI). The reaction is carried out in a solvent such as diethyl ether, tetrahydrofuran, pentane or a mixture of these solvents and at a temperature of between −70° C. and room temperature.

The compounds of formula (XII) are commercially available or are synthesized conventionally.

The compounds of formula (XIV) are prepared by reacting the corresponding aniline derivatives with di-tert-butyl dicarbonate according to the conventional methods.

The compounds of formula (VII) are known and are prepared according to known methods such as those disclosed in WO 95/18105 or in J. Org. Chem., 1968, 33, 1640–1643.

The compounds of formula (II) in which X=—CH$_2$—, Y represents a chlorine atom and W=H are prepared from the corresponding compounds of formula (II) in which Y=OH by reaction with thionyl chloride in a solvent such as toluene and at a temperature of between 0° C. and the reflux temperature of the solvent.

The compounds of formula (II) in which —X— represents an —O— group, Y represents a phenoxy and

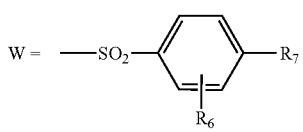

are prepared according to Scheme 3 below in which $R_1$, $R_2$, $R_3$, $R_4$, $R_6$ and $R_7$ are as defined for a compound of formula (I).

SCHEME 3

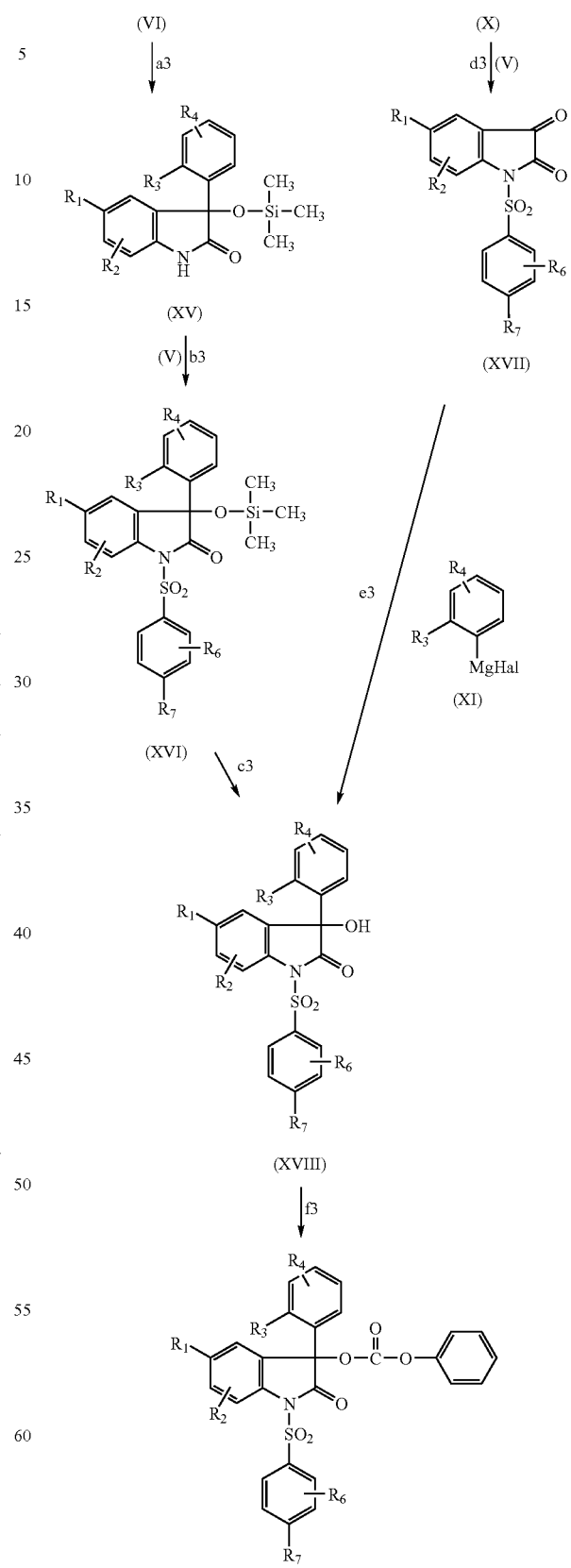

(II): X = —O—; Y = phenoxy; W = —SO$_2$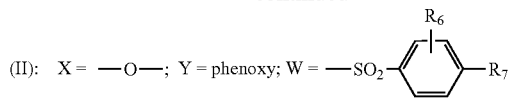

In step a3 of Scheme 3, the hydroxyl of a compound of formula (VI) is selectively protected using, for example, hexamethyldisilazane according to the method described in Synthetic Communications, 1993, 23 (12), 1633–1641.

The compound of formula (XV) thus obtained is reacted, in step b3, with a sulphonyl halide of formula (V), in the presence of a strong base, according to the conditions described above.

In step c3, the deprotection of the trimethylsilyl group of the compound of formula (XVI) thus obtained gives the compound of formula (XVIII). The reaction is carried out by the action of a strong acid such as hydrochloric acid or trifluoroacetic acid, in a solvent such as dichloromethane, acetone, tetrahydrofuran or water or a mixture of these solvents and at a temperature of between room temperature and the reflux temperature of the solvent.

A compound of formula (XVIII) may also be obtained by reaction, in step d3, of a compound of formula (X) with a sulphonyl halide of formula (V), according to the conditions described above, followed by reaction of the compound of formula (XVII) thus obtained with an organomagnesium derivative of formula (XI) according to the conditions described previously.

In step f3, the compound of formula (XVIII) thus obtained is reacted with phenyl chloroformate, in the presence of a base such as pyridine, in a solvent such as dichloromethane or without a solvent, at a temperature of between 0° C. and 100° C., to give the expected compound of formula (II).

The compound of formula (VI) is prepared according to the methods described previously. A compound of formula (VI) may also be prepared by oxidation with air of a compound of formula (VIII) in the presence of a base such as sodium hydride and in the presence of dimethyl disulphide.

A compound of formula (VI) may also be prepared by hydrolysis of a halide of formula:

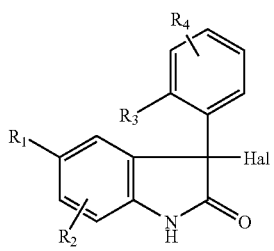

(XIX)

in which R$_1$, R$_2$, R$_3$ and R$_4$ are as defined for a compound of formula (I) and Hal represents a halogen atom, preferably bromine or chlorine. The reaction is carried out in a solvent such as tetrahydrofuran and at a temperature of between room temperature and the reflux temperature of the solvent.

The compounds of formula (XIX) are known and are prepared according to known methods such as those described in WO 95/18105.

The compounds of formula (II) in which -X— represents an —NH— group, Y represents a phenoxy and W represents a group

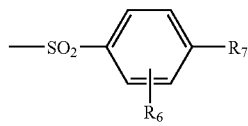

are prepared according to the processes described in WO 95/18105.

The compounds of formula (II) in which —X— represents an —O—CH$_2$— group, Y represents a hydroxyl and W represents hydrogen are prepared according to Scheme 4 below in which R$_1$, R$_2$, R$_3$ and R$_4$ are as defined for a compound of formula (I).

SCHEME 4

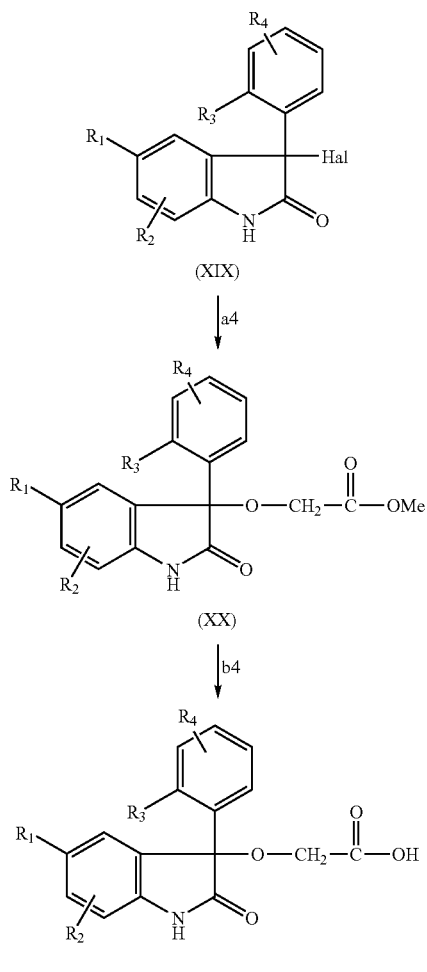

(II): —X— = —O—CH$_2$—; Y = OH; W = H.

In step a4 of Scheme 4, a compound of formula (XIX) is reacted with methyl glycolate, in the presence of a strong base such as sodium hydride, in a solvent such as tetrahydrofuran or dichloromethane and at a temperature of between 0° C. and the reflux temperature of the solvent.

The compound of formula (XX) thus obtained is hydrolysed in step b4 in alkaline medium according to the methods described previously in step d1 of Scheme 1, to give the expected compound of formula (II).

The compounds of formula (II) in which X=—O—CH$_2$—, Y represents a chlorine atom and W=H are prepared from the corresponding compounds of formula (II) in which Y=OH by reaction with thionyl chloride according to the method mentioned previously.

The compounds of formula (II) in which —X— represents an —NH—CH$_2$— group, Y represents a hydroxyl and W represents a group

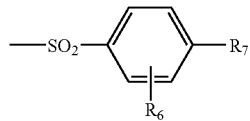

are prepared according to Scheme 5 below, in which R$_1$, R$_2$, R$_3$, R$_4$, R$_6$ and R$_7$ are as defined for a compound of formula (I).

In step a5 of Scheme 5, a compound of formula (XIX) is reacted with glycine tert-butyl ester, in the presence of a base such as triethylamine or N,N-diisopropylethylamine, in a solvent such as dichloromethane, chloroform or tetrahydrofuran or a mixture of these solvents and at a temperature of between 0° C. and room temperature.

The compound of formula (XXI) thus obtained is reacted, in step b5, with a sulphonyl halide of formula (V), in the presence of a strong base, according to the conditions described previously.

In step c5, the compound of formula (XXII) thus obtained is hydrolysed in acidic medium using a strong acid such as hydrochloric acid or trifluoroacetic acid, in a solvent such as dichloromethane, tetrahydrofuran, acetone or water, a mixture of these solvents or without a solvent, and at a temperature of between 0° C. and room temperature. The expected compound of formula (II) is thus obtained.

The compounds of formula (II) in which X=—NH—CH$_2$—, Y represents a chlorine atom and

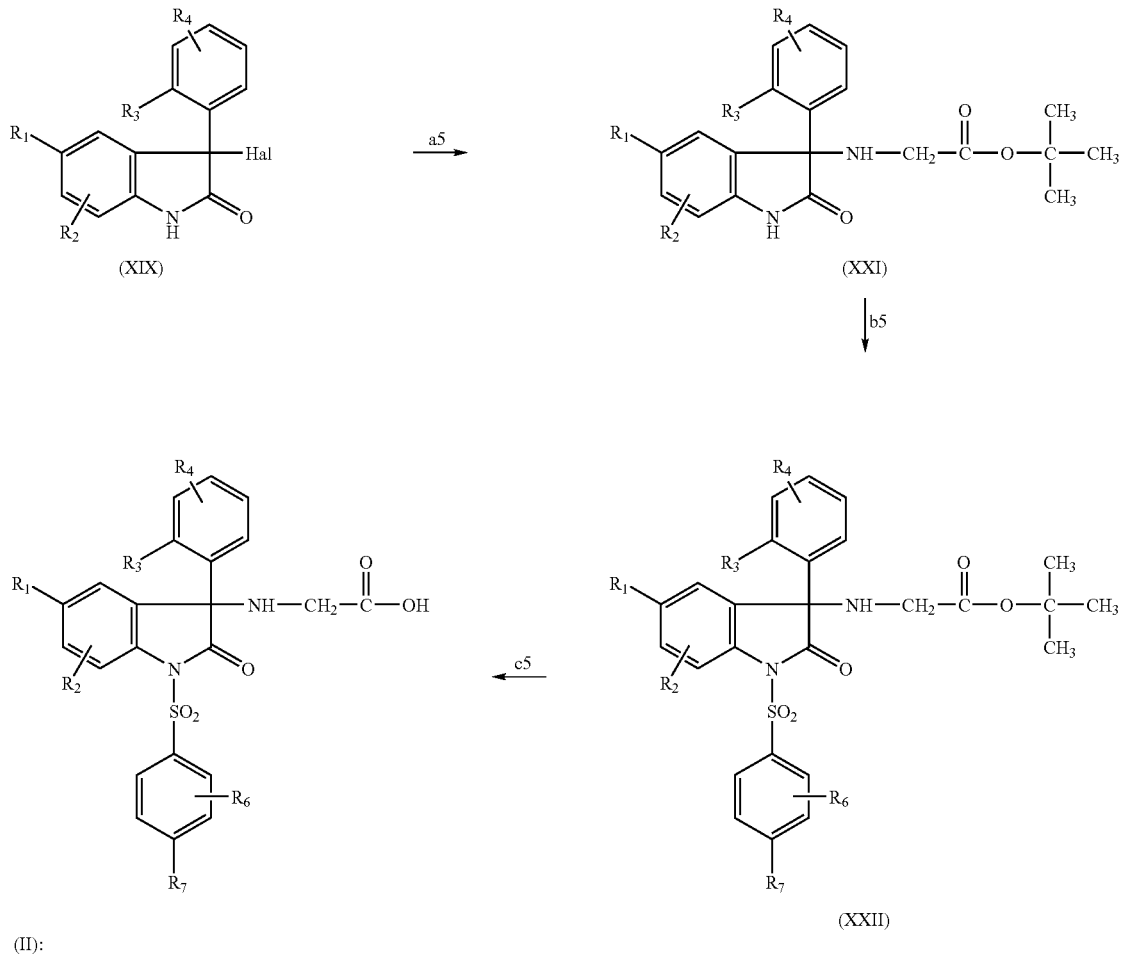

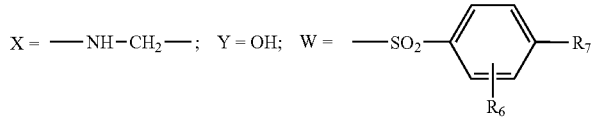

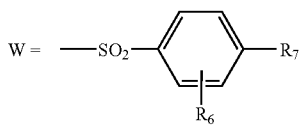

are prepared from the corresponding compounds of formula (II) in which Y=OH, according to the methods described previously.

The compounds of formula (I) in which —X— represents an —NH—CH$_2$—CH$_2$— group, Y represents a hydroxyl and W represents a group

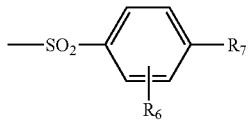

are prepared according to Scheme 6 below, in which R$_1$, R$_2$, R$_3$, R$_4$, R$_6$ and R$_7$ are as defined for a compound of formula (I).

In step a6 of Scheme 6, a compound of formula (XIX) is reacted with β-alanine tert-butyl ester, in the presence of a base such as triethylamine or N,N-diisopropylethylamine, in a solvent such as dichloromethane, chloroform or tetrahydrofuran or a mixture of these solvents and at a temperature of between 0° C. and room temperature.

The compound of formula (XXIII) thus obtained is reacted, in step b6, with a sulphonyl halide of formula (V), in the presence of a strong base, according to the conditions described previously.

In step c6, the compound of formula (XXIV) thus obtained is hydrolysed in acidic medium according to the conditions described previously in step c5 of Scheme 5. The expected compound of formula (II) is thus obtained.

The compounds of formula (II) in which —X—=—NH—CH$_2$—CH$_2$—, Y represents a chlorine atom and

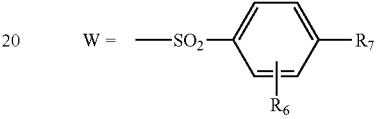

SCHEME 6

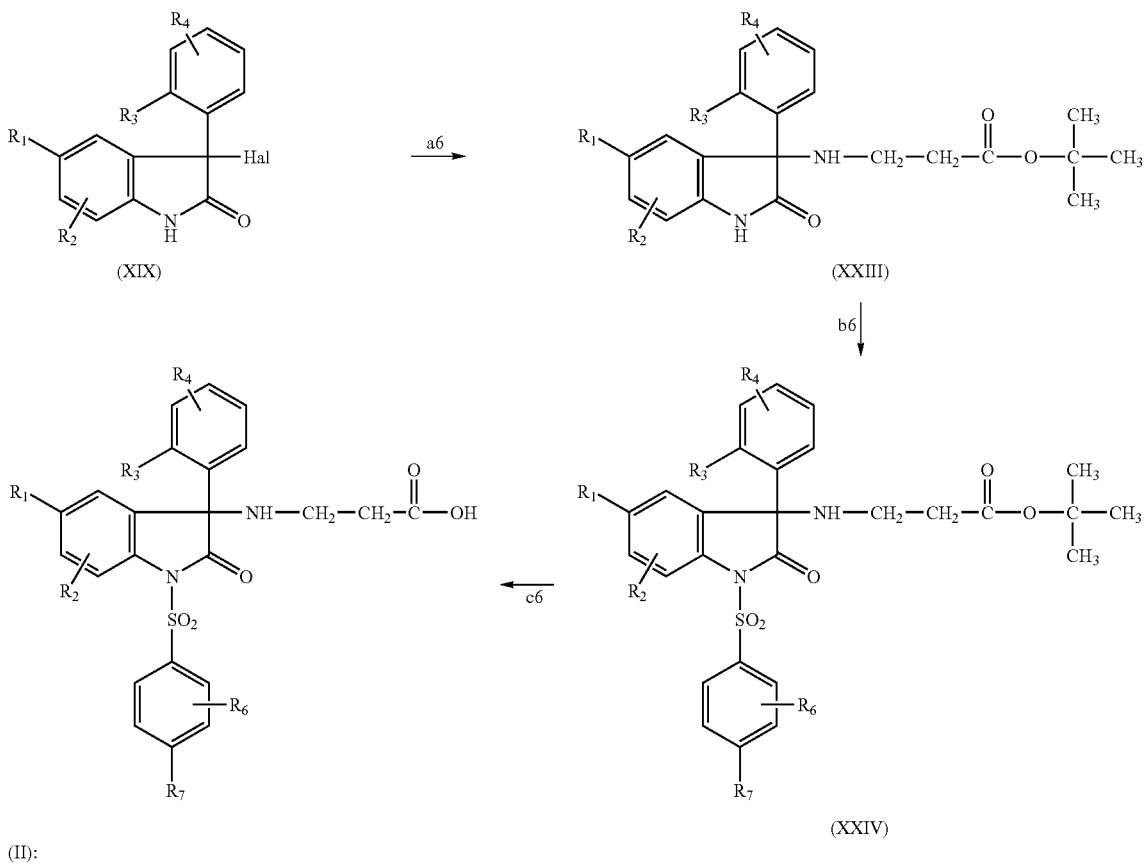

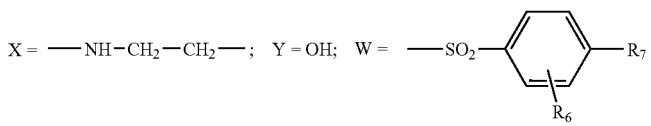

are prepared from the corresponding compounds of formula (II) in which Y=—OH according to the methods described previously.

The compounds of formula (III) are commercially available or prepared according to known methods as described in J. Org. Chem., 1953, 18, 1484–1488, J. Med. Chem., 1978, 21 (6), 536–542, Chem. Pharm. Bull., 1991, 39 (9), 2288–2300, Tetrahedron Letters, 1998, 39, 617–620 or in WO 97/28129.

For example, a compound of formula (III) is prepared by reaction of a compound of formula:

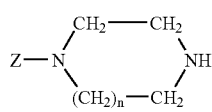  (XXV)

in which n is as defined for a compound of formula (I) and Z represents hydrogen or an N-protecting group, with a compound of formula:

Hal-R$_5$  (XXVI)

in which R$_5$ is as defined for a compound of formula (I) and Hal represents a halogen atom, preferably chlorine, bromine or iodine.

The reaction is carried out in the presence or absence of base, in an inert solvent such as ethanol, 2-propanol, n-butanol or acetonitrile and at a temperature of between 0° C. and the reflux temperature of the solvent. When a base is used, it is chosen from organic bases such as diisopropylethylamine or from alkali metal carbonates such as sodium carbonate or potassium carbonate. In the absence of base, the reaction is carried out using an excess of the compound of formula (XXV). The reaction may also be carried out without solvent, by heating the mixture of compounds (XXV) and (XXVI) to temperatures of the order of 140° C. and 180° C.

Where appropriate, when Z represents an N-protecting group, it is removed according to the standard methods to give the expected compounds of formula (III).

The compounds of formula (XXV) or of formula (XXVI) are known or are prepared according to known methods.

The compounds of formula (V) are known or prepared by known methods such as those described in EP-0 469 984 B and WO 95/18105. For example, the compounds of formula (V) may be prepared by halogenation of the corresponding benzenesulphonic acids or salts thereof, for example the sodium or potassium salts thereof. The reaction is carried out in the presence of a halogenating agent such as phosphorus oxychloride, thionyl chloride, phosphorus trichloride, phosphorus tribromide or phosphorus pentachloride, without a solvent or in an inert solvent such as a halogenated hydrocarbon or N,N-dimethylformamide and at a temperature of between –10° C. and 200° C.

The 2,4-dimethoxybenzenesulphonyl chloride is prepared according to J. Am. Chem. Soc., 1952, 74, 2008. The 3,4-dimethoxybenzenesulphonyl chloride is commercially available, or prepared according to J. Med. Chem., 1977, 20 (10), 1235–1239.

To obtain the compounds of formula (I) in the form of optically pure isomers, the standard separation techniques may be used: for example fractional recrystallizations of a salt formed from the racemic base with an optically active acid, the principle of which is well known, or the standard techniques of chiral-phase chromatography.

The optically pure compounds of formula (I) may also be prepared from an optically pure intermediate compound that is useful for preparing the compounds of formula (I).

Thus, when it is desired to prepare an optically pure compound of formula (I) in which —X—=—CH$_2$—, the optical resolution of a compound of formula (II) in which —X—=—CH$_2$—, Y=OH and W=H is carried out according to the process described in J. Am. Chem. Soc., 1989, 111, 7650–7651 using (R)-pantolactone as chiral reagent or using a chiral amine such as (+)-cinchonine.

An optically pure compound of formula (I) in which —X—=—O— may be prepared according to the process described in Scheme 7 below, in which R$_1$, R$_2$, R$_3$, R$_4$, n and R$_5$ are as defined for a compound of formula (I) and R represents a phenyl or an isobutyl.

SCHEME 7

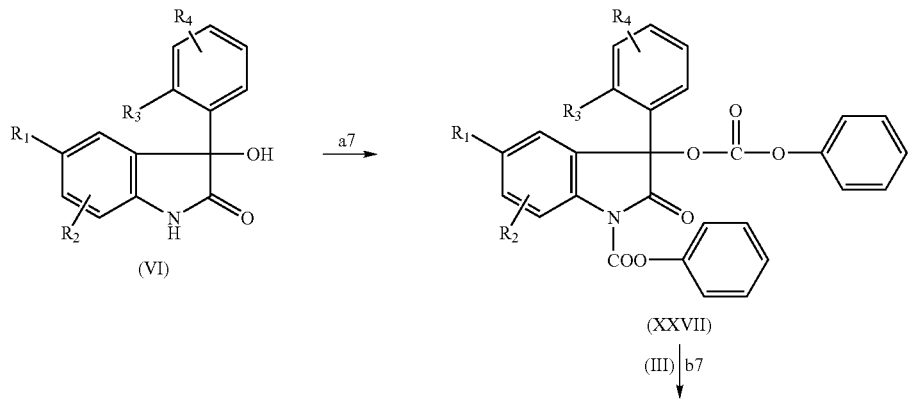

-continued

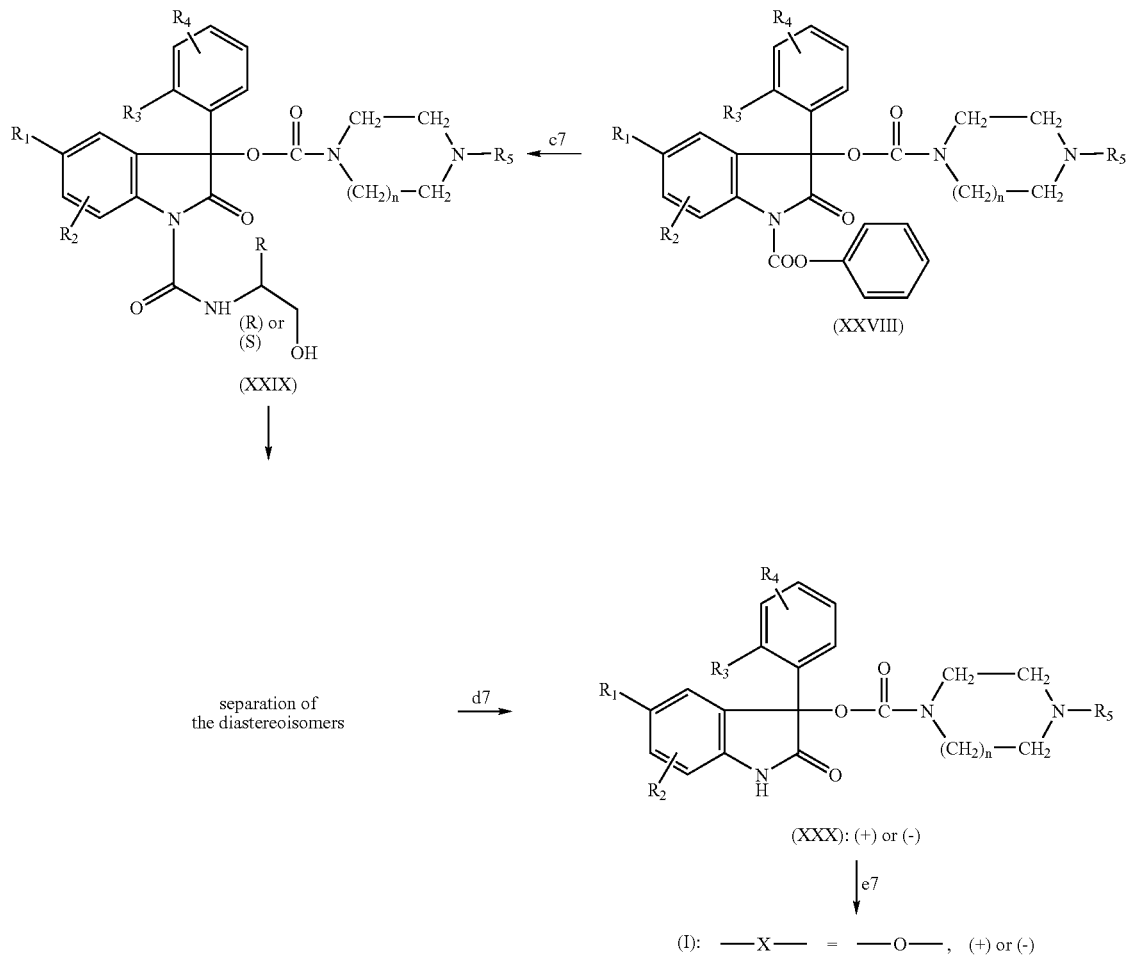

In step a7 of Scheme 7, a compound of formula (VI) is reacted with phenyl chloroformate, in the presence of a base such as pyridine, in a solvent such as dichloromethane or without a solvent and at a temperature of between 0° C. and 100° C.

The compound of formula (XXVII) thus obtained is reacted, in step b7, with a compound of formula (III), in a solvent such as dichloromethane, chloroform or tetrahydrofuran or a mixture of these solvents, at a temperature of between room temperature and the reflux temperature of the solvent, to obtain a compound of formula (XXVIII).

By reacting compound (XXVIII) with L-leucinol (R=isobutyl) or D-leucinol or with (R)-(−)-α-phenylglycinol (R=phenyl) or (S)-(+)-α-phenylglycinol, this gives, in step c7, a mixture of diastereoisomers of a compound of formula (XXIX) that may be separated, for example, by chromatography or crystallization.

By reaction, in step d7, of one of the diastereoisomers of the compound of formula (XXIX) with a strong base such as sodium methoxide, in a solvent such as methanol or tetrahydrofuran or a mixture of these solvents, at a temperature of between 0° C. and the reflux temperature of the solvent, an optically pure compound of formula (XXX) is obtained.

The reaction of compound (XXX) with a sulphonyl halide of formula (V) according to the methods described previously gives an optically pure compound of formula (I) in which X=—O—.

When it is desired to prepare an optically pure compound of formula (I) in which —X—=—NH—, a compound of formula (II) in which —X—=—NH—, Y=phenoxy and

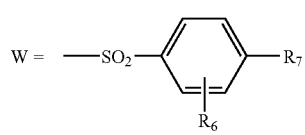

is prepared in optically pure form according to the process described in Scheme 8 below in which $R_1$, $R_2$, $R_3$, $R_4$, $R_6$ and $R_7$ are as defined for a compound of formula (I) and Hal represents a halogen atom, preferably chlorine or bromine.

SCHEME 8

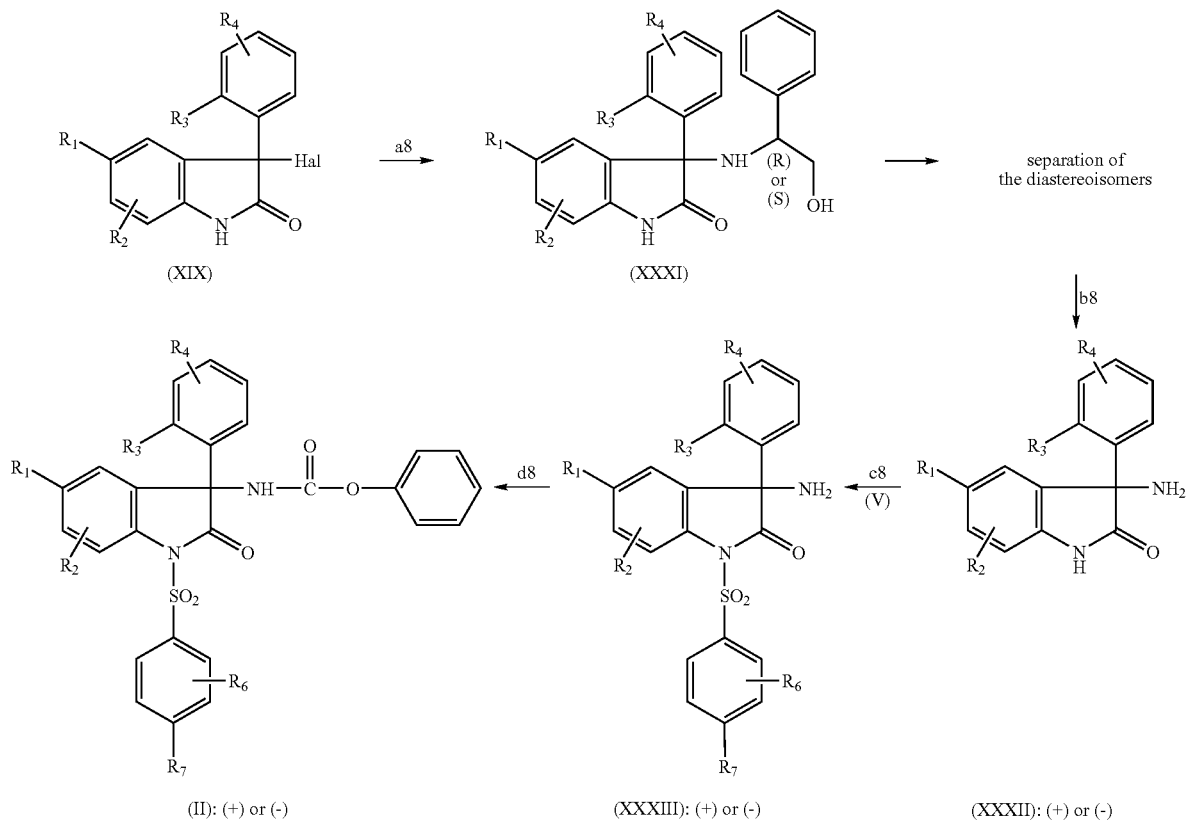

In step a8 of Scheme 8, a compound of formula (XIX) is reacted with (S)-(+)-α-phenylglycinol or (R)-(–)-α-phenylglycinol to give a mixture of diastereoisomers of a compound of formula (XXXI) that may be separated by chromatography or crystallization.

In step b8, an optically pure compound of formula (XXXII) is obtained by oxidation with lead tetraacetate and hydrolysis in acidic medium of one of the diastereoisomers of compound (XXXI).

In step c8, the reaction of compound (XXXII) thus obtained with a sulphonyl halide of formula (V) followed by the reaction of compound (XXXIII) thus obtained with phenyl chloroformate (step d8) according to the methods described in WO 95/18105 gives the expected optically pure compound (II).

During any one of the steps for preparing the compounds of formula (I) or the intermediate compounds of formula (II), (III) or (IV), it may be necessary and/or desirable to protect the reactive or sensitive functional groups, such as the amine, hydroxyl or carboxyl groups, present on any one of the molecules under consideration. This protection may be carried out using conventional protecting groups, such as those described in Protective Groups in Organic Chemistry, J. F. W. McOmie, Ed. Plenum Press, 1973, in Protective Groups in Organic Synthesis, T. W. Greene and P. G. M. Wutts, Ed. John Wiley and Sons, 1991 or in Protecting Groups, Kocienski P. J., 1994, Georg Thieme Verlag. The removal of the protecting groups may be carried out in a suitable subsequent step using the methods known to those skilled in the art and which do not affect the rest of the molecule under consideration.

The N-protecting groups that may be used are the standard N-protecting groups that are well known to those skilled in the art, such as, for example, the tert-butoxycarbonyl, fluorenylmethoxycarbonyl, benzyl, benzhydrylidene or benzyloxycarbonyl group.

The compounds of formula (IV) are novel and form part of the invention.

Thus, according to another of its aspects, a subject of the invention is compounds of formula:

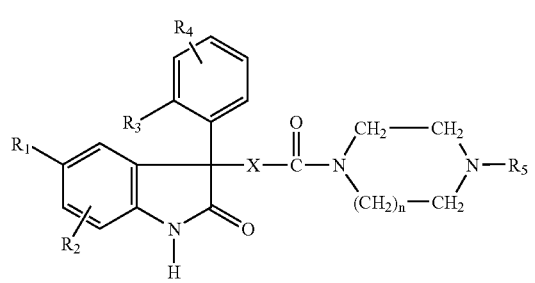

(IV)

in which:

n is 1 or 2;

X represents a group —CH$_2$—; —O—CH$_2$—;

$R_1$ represents a halogen atom; a $(C_1-C_4)$alkyl; a $(C_1-C_4)$alkoxy;

$R_2$ represents a hydrogen atom; a halogen atom; a $(C_1-C_4)$alkyl; a $(C_1-C_4)$alkoxy; a trifluoromethyl radical;

$R_3$ represents a halogen atom; a $(C_1-C_3)$alkyl; a $(C_1-C_3)$alkoxy; a trifluoromethyl radical; a trifluoromethoxy radical;

$R_4$ represents a hydrogen atom; a halogen atom; a $(C_1-C_3)$alkyl; a $(C_1-C_3)$alkoxy;

$R_5$ represents a radical chosen from:

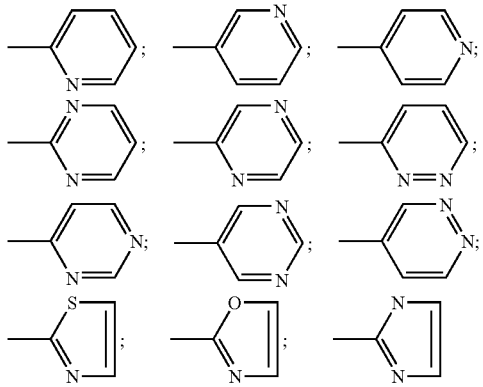

and also the salts thereof with mineral or organic acids, in the form of optically pure isomers or in the form of a mixture.

The compounds of formula (I) above also comprise those in which one or more hydrogen atoms or carbon atoms have been replaced with their radioactive isotope, for example tritium or carbon-14. Such labelled compounds are useful in research, metabolism or pharmacokinetics studies and in biochemical tests as receptor ligands.

The following PREPARATIONS and EXAMPLES illustrate the invention without, however, limiting it.

Use is made, in the Preparations and in the Examples, of the following abbreviations:
ether: diethyl ether
iso ether: diisopropyl ether
DMF: N,N-dimethylformamide
THF: tetrahydrofuran
DCM: dichloromethane
EtOAc: ethyl acetate
TMEDA: N,N,N',N'-tetramethylethylenediamine
DIPEA: diisopropylethylamine
TFA: trifluoroacetic acid
HMDS: hexamethyldisilazane
BOP: benzotriazol-1-yloxytris(dimethylamino)phosphonium hexafluorophosphate
PyBOP: benzotriazol-1-yloxytripyrrolidinophosphonium hexafluorophosphate
DCC: 1,3-dicyclohexylcarbodiimide
HOBT: 1-hydroxybenzotriazole hydrate
Hydrochloric ether: saturated solution of hydrogen chloride in diethyl ether
M.p.: melting point
RT: room temperature
B.p.: boiling point
HPLC: high performance liquid chromatography.

The proton magnetic resonance spectra ($^1$H NMR) are recorded at 200 MHz in $d_6$-DMSO using the $d_6$-DMSO peak as reference. The chemical shifts δ are expressed in parts per million (ppm). The signals observed are expressed thus: s: singlet; bs: broad singlet; d: doublet; dd: doubled doublet; t: triplet; dt: doubled triplet; q: quartet; up: unresolved peak; mt: multiplet.

The NMR spectra confirm the structures of the compounds.

PREPARATIONS

Preparations of the compounds of formula (II)

Preparation 1.1

2-[5-Chloro-3-(2-methoxyphenyl)-2-oxo-2,3-dihydro-1H-indol-3-yl]acetic acid (II): $R_1$=Cl; $R_2$=H; $R_3$=OCH$_3$; $R_4$=H; X=—CH$_2$—; Y=OH; W=H.

A) 5-Chloro-3-hydroxy-3-(2-methoxyphenyl)-1,3-dihydro-2H-indol-2-one.

This compound is prepared according to the procedure described in WO 95/18105. A solution of 2-methoxyphenylmagnesium bromide is prepared from 16 g of magnesium in 35 ml of ether and a solution of 124 g of 1-bromo-2-methoxybenzene in 175 ml of ether. This solution is added dropwise, under an argon atmosphere, to a mixture of 30 g of 5-chloro-1H-indole-2,3-dione in 250 ml of THF, cooled beforehand in an icebath, and the mixture is then left stirring and the temperature is allowed to return to RT. After stirring for 1 hour at RT, the reaction mixture is poured slowly into saturated NH$_4$Cl solution and the THF is evaporated off under vacuum. The precipitate formed is filtered off by suction and washed with iso ether. 42 g of the expected product are obtained, and are used without further purification in the following step.

B) 5-Chloro-3-(2-methoxyphenyl)-1,3-dihydro-2H-indol-2-one.

A mixture of 5.8 g of the compound obtained in the preceding step, 25 ml of TFA and 10 ml of triethylsilane is refluxed for 24 hours. The reaction mixture is concentrated under vacuum at 100° C., the residue is taken up in 30 ml of iso ether and is left to stand at 20° C. for 15 hours. The precipitate formed is filtered off by suction and washed with iso ether and then with heptane. 4.3 g of the expected product are obtained.

C) Ethyl 2-[5-Chloro-3-(2-methoxyphenyl)-2-oxo-2,3-dihydro-1H-indol-3-yl]acetate A mixture of 2.85 g of the compound obtained in the preceding step, 2.05 g of ethyl bromoacetate, 2.05 g of KI and 3.1 g of K$_2$CO$_3$ in 15 ml of acetone is refluxed for 20 hours. The mineral salts are filtered off and the filtrate is concentrated under vacuum. The residue is extracted with EtOAc, the organic phase is washed with water and dried over Na$_2$SO$_4$ and the solvent is evaporated off under vacuum. The residue is triturated in iso ether and the precipitate formed is filtered off by suction. The precipitate is chromatographed on silica gel, eluting with DCM and then with EtOAc. 1.55 g of the expected product are obtained after recrystallization from iso ether, m.p.=184–187° C.

D) 2-[5-Chloro-3-(2-methoxyphenyl)-2-oxo-2,3-dihydro-1H-indol-3-yl]acetic acid

A solution of 0.5 g of NaOH pellets in 10 ml of water is added, at RT, to a mixture of 1.5 g of the compound obtained in the preceding step in 30 ml of MeOH, and the mixture is stirred for 20 hours at 20° C. The reaction mixture is concentrated under vacuum, the residue is taken up in 20 ml of water, the aqueous phase is washed with EtOAc and acidified to pH 1 by addition of concentrated HCl, and the precipitate formed is filtered off by suction. 1.15 g of the expected product are obtained, m.p.=135–139° C.

Preparation 1.2

2-[5-Chloro-3-(2-ethoxyphenyl)-2-oxo-2,3-dihydro-1H-indol-3-yl]acetic acid (II): $R_1$=Cl; $R_2$=H; $R_3$=OCH$_2$CH$_3$; $R_4$=H, X=—CH$_2$—; Y=OH; W=H A) 1-Bromo-2-ethoxybenzene A mixture of 17.5 g of 2-bromophenol, 66 ml of diethyl sulphate and 170 ml of 10% NaOH solution is refluxed for 2 hours. After cooling the reaction mixture to RT, it is extracted with EtOAc and the organic phase is washed with 2N NaOH solution, dried over Na$_2$SO$_4$ and the solvent is evaporated off under vacuum. 19.6 g of the expected product are obtained.

B) 5-Chloro-3-(2-ethoxyphenyl)-3-hydroxy-1,3-dihydro-2H-indol-2-one

A solution of 2-ethoxyphenylmagnesium bromide is prepared from 2.2 g of magnesium in 10 ml of ether and from a solution of 16.5 g of the compound obtained in the preceding step in 40 ml of ether. This solution is added, dropwise and under a nitrogen atmosphere, to a mixture of 5 g of 5-chloro-1H-indole-2,3-dione in 20 ml of THF, while keeping the temperature of the reaction medium below 35° C. After stirring for 2 hours at RT, the reaction mixture is poured into 200 ml of 2N HCl, extracted with EtOAc, the organic phase is dried over Na$_2$SO$_4$ and the solvents are evaporated off under vacuum. The residue is taken up in hot iso ether and left to crystallize. The crystalline product formed is filtered off by suction, washed with iso ether and dried. 5.7 g of the expected product are obtained, m.p.=251° C.

C) 5-Chloro-3-(2-ethoxyphenyl)-1,3-dihydro-2H-indol-2-one

This compound is prepared according to the procedure described in step B of Preparation 1.1, starting with 4 g of the compound obtained in the preceding step, 15 ml of TFA and 5.6 ml of triethylsilane. 3.6 g of the expected product are obtained.

D) Ethyl 2-[5-chloro-3-(2-ethoxyphenyl)-2-oxo-2,3-dihydro-1H-indol-3-yl]acetate

This compound is prepared according to the procedure described in step C of Preparation 1.1, starting with 3.5 g of the compound obtained in the preceding step, 2.2 g of ethyl bromoacetate, 2.2 g of KI and 3.5 g of K$_2$CO$_3$ in 20 ml of acetone. 1.7 g of the expected product are obtained after precipitation from iso ether, m.p.=181° C.

E) 2-[5-Chloro-3-(2-ethoxyphenyl)-2-oxo-2,3-dihydro-1H-indol-3-yl]acetic acid

A mixture of 1.65 g of the compound obtained in the preceding step and 2 ml of 30% NaOH solution in 50 ml of water and 20 ml of THF is stirred at RT for 24 hours. The mixture is concentrated under vacuum, the residue is taken up in 100 ml of water, the aqueous phase is washed with EtOAc and acidified to pH 1 by addition of concentrated HCl, and extracted with EtOAc, the organic phase is washed with water and dried over Na$_2$SO$_4$ and the solvent is evaporated off under vacuum. 1.2 g of the expected product are obtained after crystallization from iso ether, m.p.=212° C.

Preparation 1.3

2-[5-Chloro-3-(2-isopropoxyphenyl)-2-oxo-2,3-dihydro-1H-indol-3-yl]acetic acid, dextrorotatory isomer (II): $R_1$=Cl; $R_2$=H; $R_3$=OCH(CH$_3$)$_2$; $R_4$=H; X=—CH$_2$—; Y=OH; W=H A) 1-Bromo-2-isopropoxybenzene A sodium ethoxide solution is prepared from 280 ml of EtOH and 7.3 g of sodium, 50 g of 2-bromophenol are added and the mixture is stirred at RT for 30 minutes. 43 g of isopropyl bromide are then added and the mixture is refluxed for 15 hours. The reaction mixture is concentrated under vacuum, the residue is taken up in 1N NaOH solution and extracted with ether, the organic phase is dried over Na$_2$SO$_4$ and the solvent is evaporated off under vacuum. The resulting oil is distilled under reduced pressure to give 49.3 g of the expected product in the form of a colourless liquid, b.p.=113–115° C. at 3366 Pa.

B) 5-Chloro-3-hydroxy-3-(2-isopropoxyphenyl)-1,3-dihydro-2H-indol-2-one

A 2-isopropoxyphenylmagnesium bromide solution is prepared from 6.3 g of magnesium in 20 ml of ether and 49.3 g of the compound obtained in the preceding step. This solution is added over 3 minutes to a mixture of 13.3 g of 5-chloro-1H-indole-2,3-dione in 30 ml of THF, followed by refluxing for 90 minutes. After cooling to RT, the reaction mixture is poured into an ice/concentrated HCl mixture and extracted with EtOAc, the organic phase is washed with 1N NaOH solution and with water, and dried over Na$_2$SO$_4$, and the solvent is evaporated off under vacuum. The residue is taken up in hot iso ether and the precipitate formed is filtered off by suction, after trituration. 17.4 g of the expected product are obtained.

C) 5-Chloro-3-(2-isopropoxyphenyl)-1,3-dihydro-2H-indol-2-one

A mixture of 3.5 g of the compound obtained in the preceding step, 15 ml of TFA and 5.5 ml of triethylsilane is refluxed for 8 hours. The mixture is concentrated under vacuum and the residue is chromatographed on silica gel, eluting with iso ether and then with DCM. 2.2 g of the expected product are obtained after crystallization from heptane, m.p.=154° C.

D) Ethyl 2-[5-chloro-3-(2-isopropoxyphenyl)-2-oxo-2,3-dihydro-1H-indol-3-yl]acetate This compound is prepared according to the procedure described in step C of Preparation 1.1, starting with 2.55 g of the compound obtained in the preceding step, 1.67 g of ethyl bromoacetate, 1.66 g of KI and 2.52 g of K$_2$CO$_3$ in 12 ml of acetone. The product obtained is chromatographed on alumina, eluting with DCM and then with acetone. 1.6 g of the expected product are obtained after crystallization from iso ether, m.p.=193° C.

E) 2-[5-Chloro-3-(2-isopropoxyphenyl)-2-oxo-2,3-dihydro-1H-indol-3-yl]acetic acid A solution of 1 g of NaOH pellets in 10 ml of water is added, at 40° C., to a solution of 1.6 g of the compound obtained in the preceding step in 10 ml of EtOH, and the mixture is stirred for 20 hours at 20° C. The resulting mixture is concentrated under vacuum, the residue is taken up in 30 ml of water and heated to 40° C., and the insoluble material is filtered off. The filtrate is acidified to pH 1 by addition of concentrated HCl, and the precipitate formed is filtered off by suction and dried. 1.15 g of the expected product are obtained, m.p.=146–148° C.

F) (3R)-4,4-dimethyl-2-oxotetrahydro-3-furanyl 2-[5-chloro-3-(2-isopropoxyphenyl)-2-oxo-2,3-dihydro-1H-indol-3-yl]acetate, the more polar isomer A mixture of 2 g of the compound obtained in the preceding step and 10 ml of thionyl chloride is stirred at 20° C, for 20 hours. The mixture is concentrated under vacuum, the residue is taken up in DCM and the solvent is concentrated under vacuum at RT to give 2 g of the acid chloride. The acid chloride is dissolved in 20 ml of DCM, this solution is added to a mixture of 0.8 g of (R)-pantolactone and 1 g of N-methylpyrrolidine in 10 ml of DCM precooled to 10° C., and the resulting mixture is stirred at RT for 2 hours. The reaction mixture is concentrated under vacuum, the residue is taken up in water and extracted with EtOAc, the organic phase is washed with water and dried over $Na_2SO_4$, and the solvent is evaporated off under vacuum. The residue is chromatographed on silica H gel, eluting with DCM. The diastereoisomers are separated and the more polar compound is collected. 0.6 g of the expected product is obtained.

G) 2-[5-Chloro-3-(2-isopropoxyphenyl)-2-oxo-2,3-dihydro-1H-indol-3-yl]acetic acid, dextrorotatory isomer A solution of 0.8 g of lithium hydroxide monohydrate in 10 ml of water is added to a mixture of 0.8 g of the compound obtained in the preceding step in 30 ml of MeOH, and the mixture is stirred at 20° C. for 20 hours. The reaction mixture is concentrated under vacuum, the residue is extracted with water and the aqueous phase is washed with ether, acidified to pH 1 by addition of concentrated HCl and extracted with DCM, the organic phase is dried over $Na_2SO_4$ and the solvent is evaporated off under vacuum. 0.5 g of the expected product is obtained.

$$\alpha_D^{20} = +84° \ (c = 0.25; \text{chloroform})$$

Preparation 1.4

2-[3-(2-chlorophenyl)-5-methyl-2-oxo-2,3-dihydro-1H-indol-3-yl]acetic acid (II): $R_1=CH_3$; $R_2=H$; $R_3=Cl$; $R_4=H$; $X=$—$CH_2$—; $Y=OH$; $W=H$.

A) 3-(2-Chlorophenyl)-5-methyl-1,3-dihydro-2H-indol-2-one

This compound is prepared according to the procedure described in WO 95/18105 in steps A and B of Preparation 65.

B) Methyl 2-[3-(2-chlorophenyl)-5-methyl-2-oxo-2,3-dihydro-1H-indol-3-yl]acetate A mixture of 5 g of the compound obtained in the preceding step in 10 ml of DMF is cooled to a temperature below 10° C., 0.87 g of 60% sodium hydride in oil is added portionwise and the mixture is stirred for 30 minutes. 3.15 ml of methyl bromoacetate are then added, the mixture is stirred at RT for 4 hours, a further 1 ml of methyl bromoacetate is then added and the mixture is stirred at RT for 16 hours. The reaction mixture is poured into water and extracted with EtOAc, the organic phase is washed with water and dried over $Na_2SO_4$, and the solvent is evaporated off under vacuum. The residue is chromatographed on silica gel, eluting with DCM and then with DCM/EtOAc mixture (95/5; v/v). 0.57 g of the expected product is obtained.

C) 2-[3-(2-Chlorophenyl)-5-methyl-2-oxo-2,3-dihydro-1H-indol-3-yl]acetic acid

A solution of 0.16 g of NaOH pellets in 40 ml of water is added to a mixture of 0.57 g of the compound obtained in the preceding step in 10 ml of dioxane, and the resulting mixture is stirred at RT for 24 hours. 50 ml of water are added to the reaction mixture, the aqueous phase is washed with EtOAc, acidified to pH 1 by addition of 1N HCl and extracted with EtOAc, the organic phase is dried over $Na_2SO_4$ and the solvent is evaporated off under vacuum. The residue is chromatographed on silica gel, eluting with a DCM/EtOAc mixture (95/5; v/v). 0.27 g of the expected product is obtained.

Preparation 1.5

2-[5,6-Dichloro-3-(2-methoxyphenyl)-2-oxo-2,3-dihydro-1H-indol-3-yl]acetic acid (II): $R_1=Cl$; $R_2=6$-$Cl$; $R_3=OCH_3$; $R_4=H$; $X=$—$CH_2$—; $Y=OH$; $W=H$ A) 5,6-Dichloro-1H-indole-2,3-dione This compound is prepared according to the procedure described in J. Am. Chem. Soc., 1946, 68, 2697–2703 or according to the procedure described in J. Org. Chem., 1952, 17, 149–156.

B) 5,6-Dichloro-3-hydroxy-3-(2-methoxyphenyl)-1,3-dihydro-2H-indol-2-one 7.5 g of 1-bromo-2-methoxybenzene are added dropwise to a suspension of 1.1 g of magnesium in 20 ml of ether containing a few crystals of iodine, the reflux being maintained once it has started. At the end of the addition, the mixture is heated at reflux for 2 hours. A suspension of 4.3 g of 5,6-dichloro-1H-indole-2,3-dione in 20 ml of THF is then added and the resulting mixture is refluxed for 30 minutes. After cooling to RT, the reaction mixture is poured into a water/ice/concentrated HCl mixture and extracted with EtOAc, the organic phase is dried over $Na_2SO_4$ and the solvent is evaporated off under vacuum. The residue is triturated in hot iso ether and the precipitate formed is filtered off by suction and washed with ether. 5.2 g of the expected product are obtained, m.p.=245–246° C.

C) 5,6-Dichloro-3-(2-methoxyphenyl)-1,3-dihydro-2H-indol-2-one

A mixture of 5.1 g of the compound obtained in the preceding step, 25 ml of TFA and 10 ml of triethylsilane is refluxed for 15 hours. The mixture is concentrated under vacuum, the residue is triturated in heptane and the precipitate formed is filtered off by suction. 4.8 g of the expected product are obtained after crystallization from iso ether, m.p.=195–197° C.

D) Ethyl 2-[5,6-dichloro-3-(2-methoxyphenyl)-2-oxo-2,3-dihydro-1H-indol-3-yl]acetate A mixture of 4.8 g of the compound obtained in the preceding step, 2.7 g of ethyl bromoacetate, 2.7 g of KI and 4.4 g of $K_2CO_3$ in 25 ml of acetone is refluxed for 16 hours. The mineral salts are filtered off and the filtrate is concentrated under vacuum. The residue is chromatographed on silica gel, eluting with DCM and then with EtOAc. 2.6 g of the expected product are obtained after crystallization from iso ether, m.p.=214–219° C.

E) 2-[5,6-Dichloro-3-(2-methoxyphenyl)-2-oxo-2,3-dihydro-1H-indol-3-yl]acetic acid 3 ml of 2N NaOH solution are added to a mixture of 2.5 g of the compound obtained in the preceding step in 50 ml of MeOH, and the mixture is stirred for 48 hours at 20° C. The resulting mixture is concentrated under vacuum, the residue is taken up in 30 ml of water, the insoluble material is filtered off, the filtrate is acidified to pH 1 by addition of concentrated HCl and is extracted with EtOAc, the organic phase is washed with water and dried over $Na_2SO_4$, and the solvent is evaporated off under vacuum. 2 g of the expected product are obtained after crystallization from iso ether, m.p.=222–224° C.

Preparation 1.6

2-[5-Chloro-3-(2-methoxyphenyl)-6-methyl-2-oxo-2,3-dihydro-1H-indol-3-yl]acetic acid (II): $R_1$=Cl; $R_2$=6-$CH_3$; $R_3$=$OCH_3$; $R_4$=H; X=—$CH_2$—; Y=OH; W=H A) Ethyl 2-(2-methoxyphenyl)-2-oxoacetate A solution of 27 g of 1-bromo-2-methoxybenzene in 270 ml of ether is cooled to −70° C., under an argon atmosphere, 90 ml of a 1.6M solution of n-butyllithium in pentane are added dropwise and the mixture is then stirred for 45 minutes. 78 ml of diethyl oxalate are added quickly and the mixture is stirred while allowing the temperature to return to RT. After stirring for 1 hour at RT, saturated $NH_4Cl$ solution is added to the reaction mixture, the phases are separated by settling, the aqueous phase is extracted with ether, the combined organic phases are washed with water and with saturated NaCl solution and dried over $Na_2SO_4$, and the solvents are evaporated off under vacuum. The excess diethyl oxalate is removed by distillation under vacuum (b.p.=87° C. at 2000 Pa). The resulting product is chromatographed on silica gel, eluting with a DCM/hexane mixture (50/50; v/v) and then with DCM. The product obtained is purified by distillation under vacuum. 13 g of the expected product are obtained, b.p.=110° C. at 3 Pa.

B) 5-Chloro-3-hydroxy-3-(2-methoxyphenyl)-6-methyl-1,3-dihydro-2H-indol-2-one a) tert-Butyl 4-chloro-3-methylphenylcarbamate A mixture of 10 g of 4-chloro-3-methylaniline and 15.26 g of di-tert-butyl dicarbonate in 50 ml of dioxane is stirred at RT for 24 hours. The reaction mixture is concentrated under vacuum and the residue is chromatographed on silica gel, eluting with a DCM/hexane mixture gradient from (50/50; v/v) to (70/30; v/v). 5.6 g of the expected product are obtained, and are used without further purification.

b) A solution of 5 g of tert-butyl 4-chloro-3-methylphenylcarbamate in 45 ml of ether is cooled to −70° C., under an argon atmosphere, 30 ml of 1.5M solution of tert-butyllithium in pentane are added dropwise, the mixture is stirred for 1 hour while allowing the temperature to rise to −10° C., and is stirred for 1 hour 45 minutes at −10° C. The reaction mixture is cooled to −70° C., a solution of 5 g of the compound obtained in step A in 25 ml of THF is added dropwise, the mixture is stirred for 1 hour and allowed to warm to −30° C., and is then stirred overnight while allowing the temperature to return to RT. Saturated $NH_4Cl$ solution is added to the reaction mixture, the THF is evaporated off, the resulting aqueous phase is extracted three times with EtOAc, the organic phase is washed with water, with saturated NaCl solution and dried over $Na_2SO_4$, the solvent is partially evaporated off and the crystalline product is filtered off by suction. 2.6 g of the expected product are obtained, m.p.=254–256° C.

C) 5-Chloro-3-(2-methoxyphenyl)-6-methyl-1,3-dihydro-2H-indol-2-one

A mixture 3 g of the compound obtained in the preceding step, 15 ml of TFA and 6 ml of triethylsilane is refluxed for 15 hours. The mixture is concentrated under vacuum and the residue is triturated in pentane to give 2.85 g of the expected product, m.p.=193° C.

D) Ethyl 2-[5-chloro-3-(2-methoxyphenyl)-6-methyl-2-oxo-2,3-dihydro-1H-indol-3-yl]acetate A mixture of 2.8 g of the compound obtained in the preceding step, 1.7 g of ethyl bromoacetate, 1.7 g of KI and 2.7 g of $K_2CO_3$ in 15 ml of acetone is refluxed for 16 hours. The mineral salts are filtered off and the filtrate is concentrated under vacuum. 2.35 g of the expected product are obtained after crystallization from iso ether, m.p.=170° C.

E) 2-[5-Chloro-3-(2-methoxyphenyl)-6-methyl-2-oxo-2,3-dihydro-1H-indol-3-yl]acetic acid A mixture of 2.3 g of the compound obtained in the preceding step and 3.5 g of a 12N solution of NaOH in 100 ml of MeOH and 5 ml of water is stirred at 20° C. for 20 hours. The mixture is concentrated under vacuum, the residue is taken up in 30 ml of water, acidified to pH 1 by addition of concentrated HCl and extracted with EtOAc, the organic phase is washed with water and dried over $Na_2SO_4$, and the solvent is evaporated off under vacuum. 1.3 g of the expected product are obtained after crystallization from iso ether, m.p.=214–216° C.

Preparation 1.7

2-[5-Chloro-3-(2-isopropoxyphenyl)-6-methyl-2-oxo-2,3-dihydro-1H-indol-3-yl]acetic acid (II): $R_1$=Cl; $R_2$=6-$CH_3$; $R_3$=$OCH(CH_3)_2$; $R_4$=H; X=—$CH_2$—; Y=OH; W=H A) Ethyl 2-[2-[(tert-butoxycarbonyl)amino]-5-chloro-4-methylphenyl]-2-oxoacetate A solution of 5.9 g of tert-butyl 4-chloro-3-methylphenylcarbamate in 60 ml of ether is cooled to −50° C., under a nitrogen atmosphere, 42 ml of a solution of tert-butyllithium in pentane are added dropwise, and the mixture is stirred for 2 hours while allowing the temperature to rise to −20° C. The reaction mixture is cooled to −70° C., a solution of 4.5 g of diethyl oxalate in 30 ml of THF is added dropwise and the resulting mixture is stirred for 1 hour while allowing the temperature to return to 20° C. The reaction mixture is poured into saturated $NH_4Cl$ solution, the phases are separated by settling, the aqueous phase is extracted with EtOAc, the combined organic phases are washed with 1N HCl and dried over $Na_2SO_4$, and the solvent is evaporated off under vacuum. The residue is chromatographed on silica gel, eluting with an iso ether/pentane mixture (50/50; v/v). 8 g of the expected product are obtained in the form of an oil which crystallizes, m.p.=111° C.

B) 5-Chloro-6-methyl-1H-indole-2,3-dione

A mixture of 8 g of the compound obtained in the preceding step and 60 ml of 3N HCl in 80 ml of THF is refluxed for 2 hours. The reaction mixture is concentrated under vacuum, the residue is taken up in EtOH and the solvent is concentrated again under vacuum. The residue is taken up in EtOH and the precipitate formed is filtered off by suction and washed with iso ether. 1.9 g of the expected product are obtained.

C) 5-Chloro-3-hydroxy-3-(2-isopropoxyphenyl)-6-methyl-1,3-dihydro-2H-indol-2-one 3.2 g of 1-bromo-2-isopropoxybenzene are added dropwise to a suspension of 0.36 g of magnesium in 10 ml of ether, the reflux being maintained once it has started. At the end of the addition, the mixture is heated at reflux for 2 hours. A solution of 1.8 g of the compound obtained in the preceding step in 30 ml of THF is then added in a single portion and the mixture is refluxed for 30 minutes. After cooling to RT, the reaction mixture is poured into an ice/concentrated HCl mixture and extracted with EtOAc, the organic phase is dried over $Na_2SO_4$ and the solvent is evaporated off under vacuum. The residue is triturated in hot iso ether and the precipitate formed is filtered off by suction and washed with hot EtOAc. 1.8 g of the expected product are obtained, and are used without further purification.

D) 5-Chloro-3-(2-isopropoxyphenyl)-6-methyl-1,3-dihydro-2H-indol-2-one

A mixture of 2.3 g of the compound obtained in the preceding step, 15 ml of TFA and 3.8 ml of triethylsilane is refluxed for 10 hours. The resulting mixture is concentrated under vacuum (13 Pa), the residue is triturated in pentane and the precipitate formed is filtered off by suction. The precipitate is chromatographed on silica gel, eluting with DCM. 0.85 g of the expected product is obtained, m.p.=145–146° C./

E) Ethyl 2-[5-chloro-3-(2-isopropoxyphenyl)-6-methyl-2-oxo-2,3-dihydro-1H-indol-3-yl]acetate A mixture of 0.8 g of the compound obtained in the preceding step, 0.53 g of ethyl bromoacetate, 0.53 g of KI and 0.8 g of $K_2CO_3$ in 6 ml of acetone is refluxed for 15 hours. The mineral salts are filtered off, the filtrate is concentrated under vacuum, the residue is extracted with DCM, the organic phase is washed with water and the insoluble material is filtered off. The filtrate is chromatographed on silica gel, eluting with DCM and then with a DCM/EtOAc mixture (70/30; v/v). 0.55 g of the expected product is obtained, m.p.=152–154° C.

F) 2-[5-Chloro-3-(2-isopropoxyphenyl)-6-methyl-2-oxo-2,3-dihydro-1H-indol-3-yl]acetic acid A mixture of 0.53 g of the compound obtained in the preceding step and 0.25 g of NaOH pellets in 20 ml of MeOH and 5 ml of water is stirred at 25° C. for 20 hours. The mixture is concentrated under vacuum, the residue is dissolved in 20 ml of water and acidified to pH 1 by addition of concentrated HCl, and the precipitate formed is filtered off by suction. 0.45 g of the expected product is obtained after crystallization from an iso ether/pentane mixture (50/50; v/v), m.p.=148–150° C.

Preparation 1.8

5-Chloro-1-[(2,4-dimethoxyphenyl)sulphonyl]-3-(2-methoxyphenyl)-2-oxo-2,3-dihydro-1H-indol-3-yl phenyl carbonate (II): $R_1$=Cl; $R_2$=H; $R_3$=OCH$_3$; $R_4$=H, X=—O—;

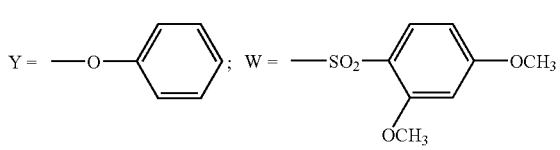

A) 5-Chloro-3-(2-methoxyphenyl)-3-[(trimethylsilyl)oxy]-1,3-dihydro-2H-indol-2-one A mixture of 2.9 g of the compound obtained in step A of Preparation 1.1 and 0.16 g of anhydrous zinc chloride in 40 ml of acetonitrile is heated to reflux, 1.7 g of HMDS are added and the mixture is refluxed for 1 hour. The resulting mixture is concentrated under vacuum, the residue is extracted with EtOAc, the organic phase is washed with water and dried over $Na_2SO_4$, and the solvent is evaporated off under vacuum. 2.4 g of the expected product are obtained after crystallization from iso ether, m.p.=185–187° C.

B) 5-Chloro-1-[(2,4-dimethoxyphenyl)sulphonyl]-3-(2-methoxyphenyl)-3-[(trimethylsilyl)oxy]-1,3-dihydro-2H-indol-2-one 0.17 g of 60% sodium hydride in oil is added to a mixture of 2.4 g of the compound obtained in the preceding step in 30 ml of THF, and the mixture is stirred for 20 minutes at RT. 1.7 g of 2,4-dimethoxybenzenesulphonyl chloride are then added and the mixture is stirred for 1 hour at RT. The resulting mixture is concentrated under vacuum, the residue is extracted with EtOAc, the organic phase is washed with water and dried over $Na_2SO_4$, and the solvent is evaporated off under vacuum. 2.65 g of the expected product are obtained after crystallization from iso ether, m.p.=157–158° C.

C) 5-Chloro-1-[(2,4-dimethoxyphenyl)sulphonyl]-3-hydroxy-3-(2-methoxyphenyl)-1,3-dihydro-2H-indol-2-one A mixture of 2.4 g of the compound obtained in the preceding step and 10 ml of TFA in 20 ml of DCM is stirred for 4 hours at 20° C. The mixture is concentrated under vacuum, the residue is extracted with EtOAc, the organic phase is washed with 10% $Na_2CO_3$ solution and dried over $Na_2SO_4$, and the solvent is evaporated off under vacuum. 1.75 g of the expected product are obtained after crystallization from iso ether, m.p.=153–160° C.

D) 5-Chloro-1-[(2,4-dimethoxyphenyl)sulphonyl]-3-(2-methoxyphenyl)-2-oxo-2,3-dihydro-1H-indol-3-yl phenyl carbonate A mixture of 1.6 g of the compound obtained in the preceding step and 1 g of phenyl chloroformate in 20 ml of pyridine is stirred for 3 days at 20° C. The mixture is concentrated under vacuum, the residue is extracted with EtOAc, the organic phase is washed with 10% AcOH solution and dried over $Na_2SO_4$, and the solvent is evaporated off under vacuum. The residue is chromatographed on silica gel, eluting with iso ether. 1.05 g of the expected product are obtained after crystallization from iso ether, m.p.=212–213° C.

Preparation 1.9

5-Chloro-1-[(2,4-dimethoxyphenyl)sulphonyl]-3-(2-isopropoxyphenyl)-2-oxo-2,3-dihydro-1H-indol-3-yl phenyl carbonate (II): $R_1$=Cl; $R_2$=H; $R_3$=OCH(CH$_3$)$_2$; $R_4$=H, X=—O—;

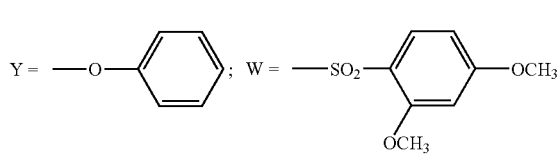

A) 5-Chloro-1-[(2,4-dimethoxyphenyl)sulphonyl]-1H-indole-2,3-dione 0.5 g of 60% sodium hydride in oil is added to a mixture of 3.6 g of 5-chloro-1H-indole-2,3-dione in 20 ml of DMF, and the mixture is stirred for 30 minutes at 20° C. 4.8 g of 2,4-dimethoxybenzenesulphonyl chloride are then added and the mixture is stirred at 20° C. for 1 hour. The resulting mixture is concentrated under vacuum (1.3 Pa), the residue is extracted with EtOAc, the organic phase is washed with water and dried over $Na_2SO_4$, and the solvent is evaporated off under vacuum. The residue is triturated in iso ether and the precipitate formed is filtered off by suction. 2.9 g of the expected product are obtained after crystallization from hot EtOAc, m.p.=194.5° C.

B) 5-Chloro-1-[(2,4-dimethoxyphenyl)sulphonyl]-3-hydroxy-3-(2-isopropoxyphenyl)-1,3-dihydro-2H-indol-2-one A solution of 2-isopropoxyphenylmagnesium bromide is prepared from 0.5 g of magnesium in 20 ml of THF and 4 g of 1-bromo-2-isopropoxybenzene. This solution is added dropwise and at RT to a mixture of 4.8 g of the compound obtained in the preceding step in 50 ml of THF, followed by refluxing for 1 hour. After cooling to RT, the reaction mixture is poured into an ice/6N HCl mixture and extracted with EtOAc, the organic phase is washed with water and dried over $Na_2SO_4$, and the solvent is evaporated off under vacuum. The residue is chromatographed on silica gel, eluting with a DCM/MeOH mixture (99/1; v/v). 3.8 g of the expected product are obtained.

C) 5-Chloro-1-[(2,4-dimethoxyphenyl)sulphonyl]-3-(2-isopropoxyphenyl)-2-oxo-2,3-dihydro-1H-indol-3-yl phenyl carbonate A mixture of 1 g of the compound obtained in the preceding step and 1.4 g of phenyl chloroformate in 10 ml of pyridine is stirred at RT for 48 hours. The mixture is concentrated under vacuum, the residue is extracted with EtOAc, the organic phase is washed with water, with 1N HCl solution, with water and dried over $Na_2SO_4$, and the solvent is evaporated off under vacuum. 0.86 g of the expected product is obtained after crystallization from iso ether, m.p.=197° C.

Preparation 1.10

Phenyl 5-chloro-3-[(2-isopropoxyphenyl)-2-oxo-3-[(phenoxycarbonyl)oxy]-1-indolinecarboxylate (XXVII): $R_1$=Cl, $R_2$=H; $R_3$=OCH($CH_3$)$_2$; $R_4$=H A mixture of 6.34 g of the compound obtained in step B of Preparation 1.3 in 60 ml of pyridine is heated to 70° C., 7 g of phenyl chloroformate are added dropwise and the mixture is then stirred at 70° C. for 3 hours and at RT overnight. The reaction mixture is poured into water and extracted with DCM, the organic phase is washed with water and dried over $Na_2SO_4$, and the solvent is evaporated off under vacuum. The residue is chromatographed on silica gel, eluting with DCM. The product obtained is triturated in iso ether and the precipitate formed is filtered off by suction. 8 g of the expected product are obtained.

Preparation 1.11

5-Chloro-3-(2-chlorophenyl)-1-((2,4-dimethoxyphenyl)sulphonyl]-2-oxo-2,3-dihydro-1H-indol-3-yl phenyl carbonate (II): $R_1$=Cl; $R_2$=H; $R_3$=Cl; $R_4$=H, X=—O—;

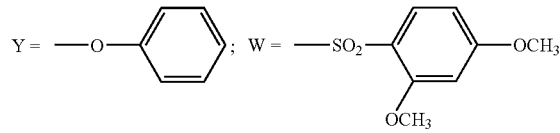

A) 5-Chloro-3-(2-chlorophenyl)-1-[(2,4-dimethoxyphenyl)sulphonyl]-3-hydroxy-1,3-dihydro-2H-indol-2-one A solution of 2-chlorophenylmagnesium bromide is prepared from 0.4 g of magnesium, 0.01 g of iodine, 20 ml of ether and 2.9 g of 1-bromo-2-chlorobenzene. A mixture of 2.8 g of the compound obtained in step A of Preparation 1.9 in 30 ml of THF is added to this solution at reflux, over 1 minute, and the resulting mixture is maintained at reflux for 20 minutes. After cooling to RT, the reaction mixture is poured into an ice/concentrated HCl mixture and extracted with EtOAc, the organic phase is washed with water and dried over $Na_2SO_4$, and the solvent is evaporated off under vacuum. The residue is chromatographed on silica gel, eluting with iso ether and then with DCM. 1.55 g of the expected product are obtained in the form of a foam, which is used without further purification.

B) 5-Chloro-3-(2-chlorophenyl)-1-[(2,4-dimethoxyphenyl)sulphonyl]-2-oxo-2,3-dihydro-1H-indol-3-yl phenyl carbonate A mixture of 0.65 g of the compound obtained in the preceding step and 0.3 g of phenyl chloroformate in 5 ml of pyridine is stirred at 20° C. for 20 hours. The mixture is concentrated under vacuum, the residue is extracted with EtOAc, the organic phase is washed with 1N HCl solution, with 1N NaOH solution and with water and dried over $Na_2SO_4$, and the solvent is evaporated off under vacuum. 0.6 g of the expected product is obtained after crystallization from iso ether, m.p.=222–223° C.

Preparation 1.12

5-Chloro-1-[(2,4-dimethoxyphenyl)sulphonyl]-3-(2-fluorophenyl)-2-oxo-2,3-dihydro-1H-indol-3-yl phenyl carbonate (II): $R_1$=Cl; $R_2$=H; $R_3$=F; $R_4$=H, X=—O—;

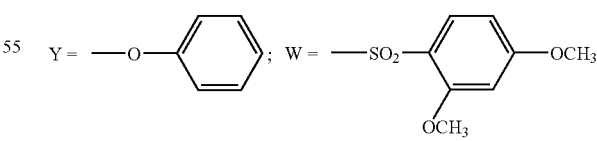

A) D,L-2-Fluoromandelic acid

This compound is prepared according to the process described in J. Org. Chem., 1968, 33, 2565–2566. This compound may also be prepared by following the procedure given below. A mixture of 17.4 g of 2-fluorobenzaldehyde and 9.6 g of potassium cyanide in 30 ml of ether is cooled to a temperature below 10° C., 15 ml of concentrated HCl are added over 30 minutes and the resulting mixture is stirred at RT for 2 hours. After separation of the phases by settling, the organic phase is dried over Na$_2$SO$_4$ and the solvent is evaporated off under vacuum. The crude product thus obtained is taken up in 20 ml of concentrated HCl and refluxed for 5 hours. After cooling to RT, the reaction mixture is extracted with ether, the organic phase is washed with water and dried over Na$_2$SO$_4$, and the solvent is evaporated off under vacuum. 17.5 g of the expected product are obtained after crystallization from iso ether.

B) N-p-Chlorophenyl-DL-2-fluoromandelamide

A mixture of 17.5 g of the compound obtained in the preceding step and 13 g of p-chloroaniline in 100 ml of 1,2-dichlorobenzene is refluxed for 3 hours, while removing the water formed with the aid of Dean-Stark apparatus. After cooling to RT, the mixture is left to crystallize. The precipitate formed is filtered off by suction and dissolved in EtOAc, the organic phase is washed twice with 4N HCl solution and dried over Na$_2$SO$_4$, and the solvent is evaporated off under vacuum. 16.2 g of the expected product are obtained after crystallization from iso ether.

C) 5-Chloro-3-(2-fluorophenyl)-1,3-dihydro-2H-indol-2-one 16.1 g of the compound obtained in the preceding step are added, at RT, to a mixture of 64 ml of concentrated (95%) H$_2$SO$_4$ and 16 ml of fuming sulphuric acid (30% oleum), and the mixture is then stirred for 8 hours. The reaction mixture is poured into a mixture of ice/water and extracted with EtOAc, the organic phase is washed twice with water and dried over Na$_2$SO$_4$, and the solvent is evaporated off under vacuum. 12.2 g of the expected product are obtained after crystallization from iso ether.

D) 3-Bromo-5-chloro-3-(2-fluorophenyl)-1,3-dihydro-2H-indol-2-one

A solution of 0.78 ml of bromine in 20 ml of chloroform is added, slowly at RT, to a solution of 4 g of the compound obtained in the preceding step in 100 ml of chloroform. The reaction mixture is concentrated under vacuum to give 4 g of the expected product, after crystallization from iso ether.

E) 5-Chloro-3-(2-fluorophenyl)-5-hydroxy-1,3-dihydro-2H-indol-2-one

A mixture of 2 g of the compound obtained in the preceding step in 5 ml of water and 20 ml of THF is refluxed for 20 hours. The mixture is concentrated under vacuum, the residue is taken up in 10% Na$_2$CO$_3$ solution and the precipitate formed is filtered off by suction. 1.45 g of the expected product are obtained after crystallization from iso ether, m.p.=265° C. (dec.).

F) 5-Chloro-3-(2-fluorophenyl)-3-[(trimethylsilyl)oxy]-1,3-dihydro-2H-indol-2-one A mixture of 1.4 g of the compound obtained in the preceding step and 0.12 g of zinc chloride in 32 ml of acetonitrile is heated to reflux, 6 ml of HMDS are added and the mixture is refluxed for 8 hours. The resulting mixture is concentrated under vacuum, the residue is extracted with EtOAc, the organic phase is washed with water and dried over Na$_2$SO$_4$, and the solvent is evaporated off under vacuum. 1.35 g of the expected product are obtained after crystallization from heptane, m.p.=125–127° C.

G) 5-Chloro-1-[(2,4-dimethoxyphenyl)sulphonyl]-3-(2-fluorophenyl)-3-[(trimethylsilyl)oxy]-1,3-dihydro-2H-indol-2-one This compound is prepared according to the procedure described in step B of Preparation 1.8, starting with 1.3 g of the compound obtained in the preceding step, 0.1 g of 60% sodium hydride in oil, 15 ml of THF and 1 g of 2,4-dimethoxybenzenesulphonyl chloride. 1.75 g of the expected product are obtained after crystallization from iso ether, m.p.=184–186° C.

H) 5-Chloro-1-[(2,4-dimethoxyphenyl)sulphonyl]-3-(2-fluorophenyl)-3-hydroxy-1,3-dihydro-2H-indol-2-one A mixture of 1.7 g of the compound obtained in the preceding step, 2 ml of 12N HCl and 2 ml of water in 30 ml of acetone is stirred for 4 hours. The mixture is concentrated under vacuum and the residue is taken up in MeOH and concentrated again under vacuum. The residue is triturated in iso ether and the precipitate formed is filtered off by suction. 1.3 g of the expected product are obtained, m.p.=144–146° C.

I) 5-Chloro-1-[(2,4-dimethoxyphenyl)sulphonyl]-3-(2-fluorophenyl)-2-oxo-2,3-dihydro-1H-indol-3-yl phenyl carbonate 0.7 g of phenyl chloroformate is added, at RT, to a mixture of 1 g of the compound obtained in the preceding step and 0.5 ml of pyridine in 20 ml of DCM, and the mixture is stirred for 48 hours. The reaction mixture is washed twice with water, the organic phase is dried over Na$_2$SO$_4$, and the solvent is evaporated off under vacuum. The residue is chromatographed on silica gel, eluting with a DCM/MeOH mixture (99.5/0.5; v/v). 0.93 g of the expected product is obtained.

Preparation 1.13

5-Chloro-1-[(2,4-dimethoxyphenyl)sulphonyl]-3-(2-trifluoromethylphenyl)-2-oxo-2,3-dihydro-1H-indol-3-yl phenyl carbonate (II): R$_1$=Cl; R$_2$=H; R$_3$=CF$_3$; R$_4$=H, X=—O—;

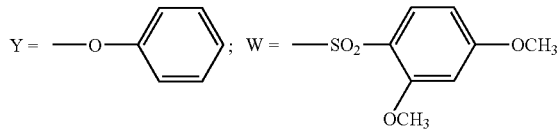

A) 5-Chloro-3-hydroxy-3-(2-trifluoromethylphenyl)-1,3-dihydro-2H-indol-2-one

A mixture of 2.3 g of magnesium and 0.01 g of iodine in 20 ml of ether is heated to reflux, a solution of 26 g of 1-bromo-2-trifluoromethylbenzene in 20 ml of ether is added dropwise and the resulting mixture is refluxed for 60 minutes. A solution of 9 g of 5-chloro-1H-indole-2,3-dione in 40 ml of THF is then added and refluxing is continued for 30 minutes. After cooling to RT, the reaction mixture is poured into an ice/concentrated HCl mixture and extracted with ether, the organic phase is washed with 1N NaOH solution and with water, and dried over Na$_2$SO$_4$, and the solvent is evaporated off under vacuum. 5.3 g of the expected product are obtained after crystallization from heptane, m.p.=205–208° C.

B) 5-Chloro-3-(2-trifluoromethylphenyl)-1,3-dihydro-2H-indol-2-one

A mixture of 3 g of the compound obtained in the preceding step and 0.1 g of zinc chloride in 20 ml of acetonitrile is heated to reflux, 6 ml of HMDS are added and the resulting mixture is refluxed for 1 hour. The mixture is concentrated under vacuum, the residue is extracted with ether, the organic phase is washed with water and dried over Na$_2$SO$_4$, and the solvent is evaporated off under vacuum. 3.9 g of the expected product are obtained in the form of an oil that crystallizes, m.p. =175–176° C.

C) 5-Chloro-1-[(2,4-dimethoxyphenyl)sulphonyl]-3-(2-trifluoromethylphenyl)-3-[(trimethylsilyl)oxy]-1,3-dihydro-2H-indol-2-one This compound is prepared according to the procedure described in step B of Preparation 1.8, starting with 3.8 g of the compound obtained in the preceding step, 0.45 g of 60% sodium hydride in oil, 30 ml of THF and 2.5 g of 2,4-dimethoxybenzenesulphonyl chloride. 5 g of the expected product are obtained after crystallization from heptane, m.p.=144–145° C.

D) 5-Chloro-1-[(2,4-dimethoxyphenyl)sulphonyl]-3-hydroxy-3-(2-trifluoromethylphenyl)-1,3-dihydro-2H-indol-2-one A mixture of 4.9 g of the compound obtained in the preceding step, 3 ml of 12N HCl and 5 ml of water in 50 ml of THF is stirred at 20° C. for 15 hours. The resulting mixture is concentrated under vacuum at a temperature below 40° C., the residue is taken up in 30 ml of 10% $NaHCO_3$ solution and extracted with EtOAc, the extracts are dried over $Na_2SO_4$ and the solvent is evaporated off under vacuum. 3.8 g of the expected product are obtained after crystallization from an iso ether/heptane mixture (80/20; v/v), m.p.=143° C.

E) 5-Chloro-1-[(2,4-dimethoxyphenyl)sulphonyl]-3-(2-trifluoromethylphenyl)-2-oxo-2,3-dihydro-1H-indol-3-yl phenyl carbonate 2 g of phenyl chloroformate are added dropwise at 20° C. to a mixture of 1.7 g of the compound obtained in the preceding step in 20 ml of pyridine, and the mixture is stirred at 20° C. for 7 hours. The resulting mixture is concentrated under vacuum, the residue is taken up in 30 ml of 10% AcOH solution and extracted with ether, the organic phase is washed with 10% $NaHCO_3$ solution and with water, and dried over $Na_2SO_4$, and the solvent is evaporated off under vacuum. 1.8 g of the expected product are obtained after crystallization from heptane, m.p.=191° C.

Preparation 1.14

5-Chloro-1-[(2,4-dimethoxyphenyl)sulphonyl]-3-(2-trifluoromethoxyphenyl)-2-oxo-2,3-dihydro-1H-indol-3-yl phenyl carbonate (II): $R_1$=Cl; $R_2$=H; $R_3$=$OCF_3$; $R_4$=H, X=—O—;

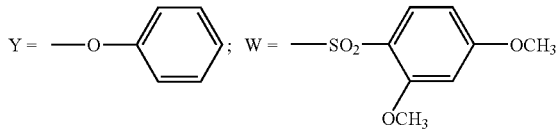

A) 5-Chloro-3-hydroxy-3-(2-trifluoromethoxyphenyl)-1,3-dihydro-2H-indol-2-one

A solution of 25 g of 1-bromo-2-trifluoromethoxybenzene in 130 ml of ether is added dropwise to a mixture of 2.8 g of magnesium in 20 ml of ether, the reflux being maintained once it has started. At the end of the addition, the mixture is heated at reflux for one hour. A mixture of 7.5 g of 5-chloro-1H-indole-2,3-dione in 100 ml of THF is then added, at a temperature below 40° C., followed by refluxing for one hour. After cooling to RT, the reaction mixture is poured into an ice/concentrated HCl mixture and extracted with EtOAc, the organic phase is washed with water, with 1N NaOH solution and dried over $Na_2SO_4$, and the solvent is evaporated off under vacuum. 6.5 g of the expected product are obtained after crystallization from a DCM/iso ether mixture (20/80; v/v), m.p.=214° C.

B) 5-Chloro-3-(2-trifluoromethoxyphenyl)-3-[(trimethylsilyl)oxy]-1,3-dihydro-2H-indol-2-one A mixture of 2 g of the compound obtained in the preceding step, 0.05 g of zinc chloride and 1.4 g of HMDS in 100 ml of acetonitrile is refluxed for 2 hours. The mixture is concentrated under vacuum, the residue is extracted with EtOAc, the organic phase is washed with water and dried over $Na_2SO_4$, and the solvent is evaporated off under vacuum. 2.5 g of the expected product are obtained, and are used without further purification.

C) 5-Chloro-1-[(2,4-dimethoxyphenyl)sulphonyl]-3-(2-trifluoromethoxyphenyl)-3-[(trimethylsilyl)oxy]-1,3-dihydro-2H-indol-2-one This compound is prepared according to the procedure described in step B of Preparation 1.8, starting with 2.5 g of the compound obtained in the preceding step, 0.3 g of 60% sodium hydride in oil, 50 ml of THF and 1.7 g of 2,4-dimethoxybenzenesulphonyl chloride. 2.7 g of the expected product are obtained after crystallization from iso ether, m.p.=181° C.

D) 5-Chloro-1-[(2,4-dimethoxyphenyl)sulphonyl]-3-hydroxy-3-(2-trifluoromethoxyphenyl)-1,3-dihydro-2H-indol-2-one A mixture of 2.7 g of the compound obtained in the preceding step and 1 ml of concentrated HCl in 50 ml of acetone is stirred for 1 hour at a temperature below 40° C. The resulting mixture is concentrated under vacuum, the residue is extracted with EtOAc, the organic phase is washed with water and dried over $Na_2SO_4$, and the solvent is evaporated off under vacuum. 1.66 g of the expected product are obtained after crystallization from iso ether, m.p.=81° C.

E) 5-Chloro-1-[(2,4-dimethoxyphenyl)sulphonyl]-3-(2-trifluoromethoxyphenyl)-2-oxo-2,3-dihydro-1H-indol-3-yl phenyl carbonate 1.15 g of phenyl chloroformate are added, at RT, to a mixture of 1.6 g of the compound obtained in the preceding step and 0.8 ml of pyridine in 20 ml of DCM, and the mixture is stirred at RT for 1 hour. The reaction mixture is washed with water and dried over $Na_2SO_4$, and the solvent is evaporated off under vacuum. 1.34 g of the expected product are obtained after crystallization from iso ether, m.p.=203–204° C.

Preparation 1.15

5-Chloro-1-[(2,4-dimethoxyphenyl)sulphonyl]-3-(2-methoxyphenyl)-6-methyl-2-oxo-2,3-dihydro-1H-indol-3-yl phenyl carbonate (II): $R_1$=Cl; $R_2$=6-$CH_3$; $R_3$=$OCH_3$; $R_4$=H, X=—O—;

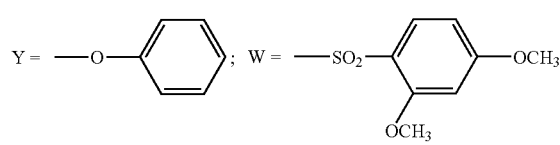

A) 5-Chloro-3-(2-methoxyphenyl)-6-methyl-3-[(trimethylsilyl)oxy]-1,3-dihydro-2H-indol-2-one A mixture of 0.65 g of the compound obtained in step B of Preparation 1.6 and 0.05 g of zinc chloride in 10 ml of acetonitrile is heated to reflux, 2.1 ml of HMDS are added and refluxing is maintained for 1 hour. The resulting mixture is concentrated under vacuum, the residue is extracted with EtOAc, the organic phase is washed with water and dried over $Na_2SO_4$, and the solvent is evaporated off under vacuum. 0.7 g of the expected product is obtained after crystallization from heptane, m.p.=227° C.

B) 5-Chloro-1-[(2,4-dimethoxyphenyl)sulphonyl]-3-(2-methoxyphenyl)-6-methyl-3-[(trimethylsilyl)oxy]-1,3-dihydro-2H-indol-2-one This compound is prepared according to the procedure described in step B of Preparation 1.8, starting with 0.85 g of the compound obtained in the preceding step, 0.06 g of 60% sodium hydride in oil, 20 ml of THF and 0.6 g of 2,4-dimethoxybenzenesulphonyl chloride. 0.95 g of the expected product is obtained after crystallization from iso ether, m.p.=190–191° C.

C) 5-Chloro-1-[(2,4-dimethoxyphenyl)sulphonyl]-3-hydroxy-3-(2-methoxyphenyl)-6-methyl-1,3-dihydro-2H-indol-2-one 0.5 ml of 12N HCl solution is added to a solution of 0.85 g of the compound obtained in the preceding step in 20 ml of acetone, and the mixture is stirred at 20° C. for 4 hours. The resulting mixture is concentrated under vacuum, the residue is taken up in 50 ml of DCM and the solvent is concentrated again under vacuum. 0.75 g of the expected product is obtained after crystallization from iso ether, m.p.=207–208° C.

D) 5-Chloro-1-[(2,4-dimethoxyphenyl)sulphonyl]-3-(2-methoxyphenyl)-6-methyl-2-oxo-2,3-dihydro-1H-indol-3-yl phenyl carbonate 1 g of phenyl chloroformate is added to a solution of 0.7 g of the compound obtained in the preceding step in 10 ml of pyridine, and the mixture is stirred at 20° C. for 48 hours. The resulting mixture is concentrated under vacuum, the residue is extracted with EtOAc, the organic phase is washed with 1N HCl solution, with water, with 1N NaOH solution and with water, and dried over $Na_2SO_4$, and the solvent is evaporated off under vacuum. 0.75 g of the expected product is obtained after crystallization from iso ether, m.p.=196° C. (dec.).

Preparation 1.16

5-Chloro-3-(2-chlorophenyl)-1-[(2,4-dimethoxyphenyl)sulphonyl]-6-methoxy-2-oxo-2,3-dihydro-1H-indol-3-yl phenyl carbonate (II): $R_1$=Cl; $R_2$=6-$OCH_3$; $R_3$=Cl; $R_4$=H, X=—O—;

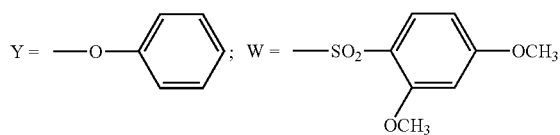

A) 4-Chloro-3-methoxyaniline

A mixture of 36 g of 2-chloro-5-nitroanisole and Raney nickel® in 150 ml of MeOH and 200 ml of THF is hydrogenated in Parr apparatus for 4 hours, at 35° C. and under a pressure of 1.3 bar. The catalyst is filtered off on Celite® and the filtrate is concentrated under vacuum. 28 g of the expected product are obtained, and are used without further purification.

B) N-(4-Chloro-3-methoxyphenyl)-D,L-2-chloromandelamide

A mixture of 28 g of the compound obtained in the preceding step and 33.13 g of D,L-2-chloromandelic acid in 128 ml of 1,2-dichlorobenzene is heated at 230° C. for 4 hours, while removing the water formed using Dean-Stark apparatus. The reaction mixture is partially concentrated under vacuum and left to crystallize. The crystalline product formed is filtered off by suction and washed with iso ether. 40 g of the expected product are obtained.

C) 5-Chloro-3-(2-chlorophenyl)-6-methoxy-1,3-dihydro-2H-indol-2-one 40 g of the compound obtained in the preceding step are added rapidly to 550 g of polyphosphoric acid and the mixture is then heated at 60° C. for 8 hours and left stirring overnight while allowing the temperature to return to RT. Iced water is added to the reaction mixture and the precipitate formed is filtered off by suction and washed with water. The precipitate is taken up in EtOAc and the white product obtained after trituration is filtered off by suction and washed with iso ether. 17.2 g of the expected product are obtained, m.p.=243–247° C.

D) 5-Chloro-3-(2-chlorophenyl)-3-hydroxy-6-methoxy-1,3-dihydro-2H-indol-2-one 2.56 g of 60% sodium hydride in oil are added at RT, under an argon atmosphere, to a solution of 17.2 g of the compound obtained in the preceding step in 220 ml of THF. After the evolution of gas has ceased, 6.85 g of dimethyl disulphide are added, air is bubbled into the reaction mixture and the mixture is stirred at RT for 72 hours. Water is added to the reaction mixture, the THF is evaporated off under vacuum, the remaining aqueous phase is extracted with EtOAc, the organic phase is washed with water, with saturated NaCl solution and dried over $Na_2SO_4$, and the solvent is evaporated off under vacuum. The product obtained is dissolved in DCM, the solvent is partially concentrated, the mixture is left to crystallize and the crystalline product formed is filtered off by suction. 6 g of the expected product are obtained, m.p.=237–240° C.

E) 5-Chloro-3-(2-chlorophenyl)-6-methoxy-3-[(trimethylsilyl)oxy]-1,3-dihydro-2H-indol-2-one A mixture of 1 g of the compound obtained in the preceding step and 0.07 g of zinc chloride in 10 ml of acetonitrile is heated to reflux, 3 ml of HMDS are added and refluxing is maintained for 1 hour. The resulting mixture is concentrated under vacuum, the residue is extracted with EtOAc, the organic phase is washed with water and dried over $Na_2SO_4$, and the solvent is evaporated off under vacuum. 1.25 g of the expected product are obtained after crystallization from heptane, m.p.=211–212° C.

F) 5-Chloro-3-(2-chlorophenyl)-1-[(2,4-dimethoxyphenyl)sulphonyl]-6-methoxy-3-[(trimethylsilyl)oxy]-1,3-dihydro-2H-indol-2-one This compound is prepared according to the procedure described in step B of Preparation 1.8, starting with 1.2 g of the compound obtained in the preceding step, 0.08 g of 60% sodium hydride in oil, 15 ml of THF and 0.8 g of 2,4-dimethoxybenzenesulphonyl chloride. 1.6 g of the expected product are obtained after crystallization from iso ether, m.p.=217–219° C.

G) 5-Chloro-3-(2-chlorophenyl)-1-[(2,4-dimethoxyphenyl)sulphonyl]-3-hydroxy-6-methoxy-1,3-dihydro-2H-indol-2-one A mixture of 1.55 g of the compound obtained in the preceding step and 2 ml of 12N HCl in 30 ml of acetone is stirred at 20° C. for 4 hours. The resulting mixture is concentrated under vacuum and the residue is taken up in acetone and concentrated again under vacuum. The residue is taken up in DCM and concentrated under vacuum. The residue is triturated in iso ether and the precipitate formed is filtered off by suction. 1.3 g of the expected product are obtained, m.p.=233–235° C.

H) 5-Chloro-3-(2-chlorophenyl)-1-[(2,4-dimethoxyphenyl)sulphonyl]-6-methoxy-2-oxo-2,3-dihydro-1H-indol-3-yl phenyl carbonate A mixture of 1.3 g of the compound obtained in the preceding step in 10 ml of pyridine is cooled to 10° C., 0.8 g of phenyl chloroformate is added and the mixture is stirred at 20° C. for 20 minutes. A further 0.7 g of phenyl chloroformate is added and the mixture is stirred at 20° C. for 20 hours. The resulting mixture is concentrated under vacuum, the residue is extracted with EtOAc, the organic phase is washed with 1N HCl solution and dried over Na$_2$SO$_4$, and the solvent is evaporated off under vacuum. The residue is chromatographed on silica gel, eluting with DCM. 0.7 g of the expected product is obtained after crystallization from a pentane/iso ether mixture, m.p.=162–163° C.

Preparation 1.17

5-Chloro-1-[(2,4-dimethoxyphenyl)sulphonyl]-3-(2,5-dimethoxyphenyl)-2-oxo-2,3-dihydro-1H-indol-3-yl phenyl carbonate (II): R$_1$=Cl; R$_2$=H; R$_3$=OCH$_3$; R$_4$=5-OCH$_3$; X=—O—;

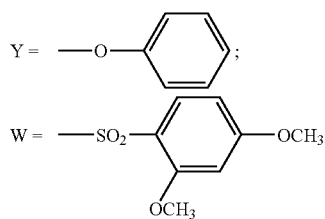

A) 5-Chloro-3-hydroxy-3-(2,5-dimethoxyphenyl)-1,3-dihydro-2H-indol-2-one

A solution of 2,5-dimethoxyphenylmagnesium bromide is prepared from 2.2 g of magnesium, 18 g of 1-bromo-2,5-dimethoxybenzene and 50 ml of ether. This solution is added dropwise to a mixture of 5 g of 5-chloro-1H-indole-2,3-dione in 50 ml of THF at a temperature below 30° C., followed by refluxing for 3 hours. After cooling to RT, the reaction mixture is poured into 1N HCl solution and extracted with EtOAc, the organic phase is washed with water and dried over Na$_2$SO$_4$, and the solvent is evaporated off under vacuum. 7.1 g of the expected product are obtained after crystallization from hot iso ether.

B) 5-Chloro-3-(2,5-dimethoxyphenyl)-3-[(trimethylsilyl)oxy]-1,3-dihydro-2H-indol-2-one A mixture of 4 g of the compound obtained in the preceding step and 0.085 g of zinc chloride in 45 ml of acetonitrile is heated to reflux, 2.8 ml of HMDS are added and refluxing is maintained for 1 hour. The resulting mixture is concentrated under vacuum, the residue is taken up in water and extracted with ether, the organic phase is washed with water and dried over Na$_2$SO$_4$, and the solvent is evaporated off under vacuum. 5 g of the expected product are obtained after crystallization from iso ether.

C) 5-Chloro-3-(2,5-dimethoxyphenyl)-1-[(2,4-dimethoxyphenyl)sulphonyl]-3-[(trimethylsilyl)oxy]-1,3-dihydro-2H-indol-2-one This compound is prepared according to the procedure described in step B of Preparation 1.8, starting with 2 g of the compound obtained in the preceding step, 0.135 g of 60% sodium hydride in oil, 40 ml of THF and 1.3 g of 2,4-dimethoxybenzenesulphonyl chloride. 2.2 g of the expected product are obtained after crystallization from iso ether.

D) 5-Chloro-3-(2,5-dimethoxyphenyl)-1-[(2,4-dimethoxyphenyl)sulphonyl]-3-hydroxy-1,3-dihydro-2H-indol-2-one A mixture of 1 g of the compound obtained in the preceding step and 0.5 ml of 12N HCl in 20 ml of acetone is stirred at RT for 4 hours. The mixture is concentrated under vacuum and the residue is taken up in DCM and concentrated again under vacuum. The residue is triturated in iso ether and the precipitate formed is filtered off by suction. 0.84 g of the expected product is obtained.

E) 5-Chloro-1-[(2,4-dimethoxyphenyl)sulphonyl]-3-(2,5-dimethoxyphenyl)-2-oxo-2,3-dihydro-1H-indol-3-yl phenyl carbonate A mixture of 0.8 g of the compound obtained in the preceding step and 0.4 ml of phenyl chloroformate in 5 ml of pyridine is stirred at RT overnight. Water is added to the reaction mixture, the resulting mixture is extracted with DCM, the organic phase is washed with 2N HCl solution and dried over Na$_2$SO$_4$, and the solvent is evaporated off under vacuum. 0.84 g of the expected product is obtained after crystallization from iso ether.

Preparation 1.18

5-Chloro-1-[(2,4-dimethoxyphenyl)sulphonyl]-3-(2-methoxyphenyl)-2-oxo-2,3-dihydro-1H-indol-3-yl phenyl carbonate (II): R$_1$=Cl; R$_2$=H; R$_3$=OCH$_3$; R$_4$=H, X=—NH—;

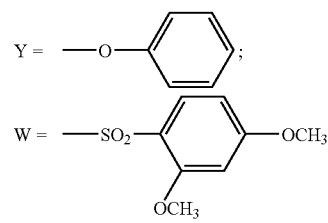

A) 3-Amino-5-chloro-3-(2-methoxyphenyl)-1,3-dihydro-2H-indol-2-one

This compound is prepared according to the procedure described in WO 95/18105, in Preparation 7.

B) 3-Amino-5-chloro-1-[(2,4-dimethoxyphenyl)sulphonyl]-3-(2-methoxyphenyl)-1,3-dihydro-1H-indol-2-one A solution of 1.64 g of the compound obtained in the preceding step in 20 ml of DMF is cooled to 4° C., 0.25 g of 60% sodium hydride in oil is added and the mixture is stirred at 4° C. for 30 minutes. 1.34 g of 2,4-dimethoxybenzenesulphonyl chloride are then added and the mixture is stirred at RT for 4 hours. 50 ml of water are added to the reaction mixture, the resulting mixture is extracted with EtOAc, the organic phase is washed with saturated NaCl solution and dried over Na$_2$SO$_4$, and the solvent is evaporated off under vacuum. The residue is chromatographed on silica gel, eluting with a DCM/EtOAc mixture (97/3; v/v). 2 g of the expected product are obtained after crystallization from a DCM/iso ether mixture.

C) 5-Chloro-1-[(2,4-dimethoxyphenyl)sulphonyl]-3-(2-methoxyphenyl)-2-oxo-2,3-dihydro-1H-indol-3-yl phenyl carbamate A solution of 2 g of the compound obtained in the preceding step and 10 ml of pyridine in 10 ml of DCM is cooled to 4° C., 0.77 ml of phenyl chloroformate is added and the mixture is stirred at RT for 1 hour. The resulting mixture is concentrated under vacuum, the residue is extracted with EtOAc, the organic phase is washed with saturated NaCl solution and dried over Na$_2$SO$_4$, and the solvent is evaporated off under vacuum. The residue is chromatographed on silica gel, eluting with a DCM/EtOAc mixture (96/4; v/v). 2.6 g of the expected product are obtained after crystallization from a DCM/iso ether mixture, m.p.=191° C.

Preparation 1.19

5-Chloro-1-[(2,4-dimethoxyphenyl)sulphonyl]-3-(2-methoxyphenyl)-2-oxo-2,3-dihydro-1H-indol-3-yl phenyl carbamate, single isomer (II): R$_1$=Cl; R$_2$=H; R$_3$=OCH$_3$; R$_4$=H, X=—NH—;

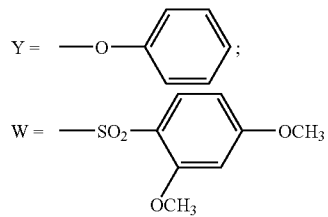

A) 3,5-Dichloro-3-(2-methoxyphenyl)-1,3-dihydro-2H-indol-2-one

A mixture of 9 g of the compound obtained in step A of Preparation 1.1 and 3.74 ml of pyridine in 100 ml of DCM is cooled to 0° C., a solution of 3.45 ml of thionyl chloride in 3 ml of DCM is added dropwise over 3 minutes, and the mixture is stirred for 30 minutes. Water is added to the reaction mixture and the DCM is evaporated off under vacuum. The precipitate formed is filtered off by suction, washed four times with water and then with cold iso ether and dried. 8.8 g of the expected product are obtained.

B) 5-Chloro-3-[[(1S)-2-hydroxy-1-phenylethyl]-amino]-3-(2-methoxyphenyl)-1,3-dihydro-2H-indol-2-one, isomer A and B A mixture of 7 g of the compound obtained in the preceding step and 7.65 g of (S)-(+)-α-phenyl-glycinol in 100 ml of chloroform is stirred at RT for 2 hours. 2.9 g of DIPEA are then added and the mixture is stirred at RT for 48 hours. The precipitate formed is filtered off by suction and isomer A is collected. The filtration liquors are washed with 5% K$_2$CO$_3$ solution, the organic phase is dried over Na$_2$SO$_4$ and the solvent is evaporated off under vacuum. The residue is chromatographed on silica gel, eluting with a DCM/EtOAc mixture (70/30; v/v). The two diastereoisomers are separated:

the less polar, isomer A: 4.55 g are obtained (precipitated and chromatographed); 20

$$\alpha_D^{20} = +193° \ (c = 0.16; \text{chloroform})$$

the more polar, isomer B.

C) 3-Amino-5-chloro-3-(2-methoxyphenyl)-1,3-dihydro-2H-indol-2-one, dextrorotatory isomer A mixture of 4.55 g of the compound obtained in the preceding step (isomer A) and 5.5 g of lead tetraacetate in 75 ml of DCM and 35 ml of MeOH is stirred at RT for 1 hour 30 minutes. The mixture is concentrated under vacuum, the residue is taken up in saturated NaHCO$_3$ solution and extracted with EtOAc, the organic phase is washed with water and with saturated NaCl solution and dried over Na$_2$SO$_4$, and the solvent is evaporated off under vacuum. The oil obtained is taken up in 100 ml of 3N HCl solution, 10 ml of MeOH are added and the mixture is stirred at RT for 2 hours. The organic solvents are concentrated under vacuum, the aqueous phase is washed twice with ether, basified by addition of KOH pellets and extracted with EtOAc, the organic phase is washed with water and with saturated NaCl solution and dried over Na$_2$SO$_4$, and the solvent is evaporated off under vacuum. 1.178 g of the expected product are obtained after crystallization from a DCM/iso ether/THF mixture, m.p.=202° C.

$$\alpha_D^{20} = +83.3° \ (c = 0.16; \text{chloroform})$$

D) 3-Amino-5-chloro-1-[(2,4-dimethoxyphenyl)sulphonyl]-3-(2-methoxyphenyl)-1,3-dihydro-2H-indol-2-one, dextrorotatory isomer A solution of 1.178 g of the compound obtained in the preceding step in 10 ml of DMF is cooled to 0° C., 0.188 g of 60% sodium hydride in oil is added, under an argon atmosphere, and the mixture is stirred until the evolution-of gas has ceased. 1.02 g of 2,4-dimethoxybenzenesulphonyl chloride are then added and the mixture is stirred at RT for 3 hours. The reaction mixture is poured into 5% K$_2$CO$_3$ solution and extracted with EtOAc, the organic phase is washed with water, with 5% K$_2$CO$_3$ solution and with saturated NaCl solution and dried over Na$_2$SO$_4$, and the solvent is evaporated off under vacuum. The residue is chromatographed on silica gel, eluting with a DCM/EtOAc mixture (95/5; v/v). 1.254 g of the expected product are obtained after crystallization from a DCM/ether/iso ether mixture, m.p.=172–173° C.

$$\alpha_D^{20} = +113° \ (c = 0.18; \text{chloroform})$$

E) 5-Chloro-1-[(2,4-dimethoxyphenyl)sulphonyl]-3-(2-methoxyphenyl)-2-oxo-2,3-dihydro-1H-indol-3-yl phenyl carbamate, single isomer A solution of 1.1 g of the compound obtained in the preceding step in 10 ml of DCM is cooled in an ice bath, 1.8 ml of pyridine are added, followed by dropwise addition of 0.37 ml of phenyl chloroformate, and the mixture is left under cold conditions overnight. The reaction mixture is diluted with DCM, the organic phase is washed three times with water, dried over Na$_2$SO$_4$, and the solvent is evaporated off under vacuum. The residue is chromatographed on silica gel, eluting with a DCM/EtOAc mixture (98/2; v/v). 1.136 g of the expected product are obtained.

Preparation 1.20

5-Chloro-1-[(2,4-dimethoxyphenyl)sulphonyl]-3-(2-isopropoxyphenyl)-2-oxo-2,3-dihydro-1H-indol-3-yl phenyl carbamate, single isomer (II): $R_1$=Cl; $R_2$=H; $R_3$=OCH(CH$_3$)$_2$; $R_4$=H, X=—NH—;

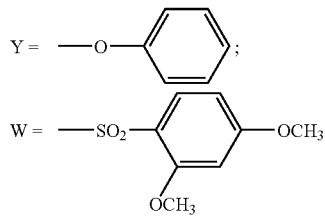

A) 3,5-Dichloro-3-(2-isopropoxyphenyl)-1,3-dihydro-2H-indol-2-one

A mixture of 12 g of the compound obtained in step B of Preparation 1.3 and 8.35 ml of pyridine in 165 ml of DCM is cooled to 0° C., 7.62 ml of thionyl chloride are added dropwise and the mixture is stirred for 15 minutes. The resulting mixture is concentrated under vacuum, the residue is extracted with EtOAc, the organic phase is washed with water and dried over Na$_2$SO$_4$, and the solvent is evaporated off under vacuum. The residue is chromatographed on silica gel, eluting with a DCM/EtOAc mixture (90/10; v;v). 15.22 g of the expected product are obtained.

B) 5-Chloro-3-[[(1S)-2-hydroxy-1-phenylethyl]-amino]-3-(2-isopropoxyphenyl)-1,3-dihydro-2H-indol-2-one, isomer A and isomer B A mixture of 8.17 g of the compound obtained in the preceding step and 3.66 g of (S)-(+)-α-phenyl-glycinol in 265 ml of chloroform is stirred at RT for 1 hour. 4.66 ml of DIPEA are then added, the mixture is stirred at RT for 3 hours and then heated at 50° C. for 18 hours. The resulting mixture is concentrated under vacuum, the residue is extracted with EtOAc, the organic phase is washed with 5% K$_2$CO$_3$ solution and with water and dried over Na$_2$SO$_4$, and the solvent is evaporated off under vacuum. The residue is chromatographed on silica gel, eluting with a DCM/EtOAc mixture (90/10; v/v) and the following is separated out:

the less polar isomer, isomer A: 4.98 g are obtained after crystallization from iso ether, m.p.=212.7° C.

$\alpha_D^{20} = +212.4°$ ($c = 0.2$; chloroform).

The chromatography is continued, eluting with a DCM/EtOAc mixture (70/30; v/v) and the following is separated out:

the more polar isomer, isomer B: 3.49 g are obtained after crystallization from iso ether, m.p.=241.3° C.

$\alpha_D^{20} = -6.6°$ ($c = 0.2$; chloroform).

C) 3-Amino-5-chloro-3-(2-isopropoxyphenyl)-1,3-dihydro-2H-indol-2-one, dextrorotatory isomer A solution of 3.9 g of the compound obtained in the preceding step (isomer A) in 75 ml of DCM and 37 ml of MeOH is cooled to 0° C., 4.35 g of lead tetraacetate are added and the mixture is stirred for 2 hours. Three drops of 5% NaHCO$_3$ solution are added, the mixture is concentrated under vacuum, the residue is extracted with EtOAc, the organic phase is washed with water and with saturated NaCl solution and dried over Na$_2$SO$_4$, and the solvent is evaporated off under vacuum. The product obtained is taken up in 120 ml of concentrated HCl and washed with ether, the aqueous phase is basified by addition of K$_2$CO$_3$, extracted with EtOAc and left to crystallize. The crystals formed are filtered off by suction and dried. The filtration liquors are concentrated under vacuum, the residue is chromatographed on silica gel, eluting with a DCM/EtOAc mixture (65/35; v/v) and the product obtained is crystallized from iso ether. 2.03 g of the expected product are obtained in total, m.p.=193° C.

$\alpha_D^{20} = +44°$ ($c = 0.18$; chloroform).

D) 3-Amino-5-chloro-1-[(2,4-dimethoxyphenyl)sulphonyl]-3-(2-isopropoxyphenyl)-1,3-dihydro-2H-indol-2-one, dextrorotatory isomer This compound is prepared according to the procedure described in step D of Preparation 1.19, starting with 1.86 g of the compound obtained in the preceding step, 0.282 g of 60% sodium hydride in oil, 20 ml of DMF and 1.395 g of 2,4-dimethoxybenzene-sulphonyl chloride. 2.68 g of the expected product are obtained after crystallization from hexane.

$\alpha_D^{20} = +79.5°$ ($c = 0.2$; chloroform).

E) 5-Chloro-1-[(2,4-dimethoxyphenyl)sulphonyl]-3-(2-isopropoxyphenyl)-2-oxo-2,3-dihydro-1H-indol-3-yl phenyl carbamate, single isomer A mixture of 2.68 g of the compound obtained in the preceding step and 4.5 ml of pyridine in 25 ml of DCM is cooled to 0° C., 1.06 g of phenyl chloroformate are added over 30 seconds and the mixture is left under cold conditions for 18 hours. The reaction mixture is chromatographed directly on silica gel prepared in a DCM/hexane mixture (80/20; v/v) and eluted with a DCM/EtOAc mixture (95/5; v/v). 2.88 g of the expected product are obtained, and are used without further purification.

Preparation 1.21

5-Chloro-1-[(2,4-dimethoxyphenyl)sulphonyl]-3-(2-isopropoxyphenyl)-2-oxo-2,3-dihydro-1H-indol-3-yl phenyl carbamate, single isomer (II): $R_1$=Cl; $R_2$=H, ; $R_3$=OCH(CH$_3$)$_2$; $R_4$=H, X=—NH—;

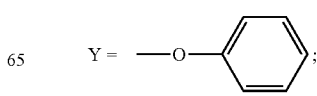

W = 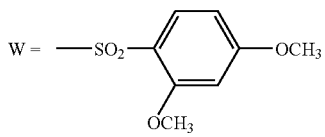

A) 3-Amino-5-chloro-3-(2-isopropoxyphenyl)-1,3-dihydro-2H-indol-2-one, laevorotatory isomer A solution of 3.4 g of the compound obtained in step B of Preparation 1.20 (isomer B) in 65 ml of DCM and 32.4 ml of MeOH is cooled to 0° C., 3.8 g of lead tetraacetate are added and the mixture is stirred for 40 minutes. Three drops of 5% NaHCO$_3$ solution are added, the mixture is concentrated under vacuum, the residue is extracted with EtOAc, the organic phase is washed with water and with saturated NaCl solution and dried over Na$_2$SO$_4$, and the solvent is evaporated off under vacuum. The product obtained is taken up in 120 ml of 0.5N HCl and washed with ether, the aqueous phase is basified by addition of K$_2$CO$_3$ and the precipitate formed is filtered off by suction. 1.9 g of the expected product are obtained after crystallization from iso ether, m.p. 192° C.

$\alpha_D^{20} = -42°$ ($c = 0.2$; chloroform).

B) 3-Amino-5-chloro-1-[(2,4-dimethoxyphenyl)sulphonyl]-3-(2-isopropoxyphenyl)-1,3-dihydro-2H-indol-2-one, laevorotatory isomer This compound is prepared according to the procedure described in step D of Preparation 1.19, starting with 1.67 g of the compound obtained in the preceding step, 0.253 g of 60% sodium hydride in oil, 20 ml of DMF and 1.249 g of 2,4-dimethoxybenzene-sulphonyl chloride. 2.453 g of the expected product are obtained after crystallization from hexane.

$\alpha_D^{20} = -79.8°$ ($c = 0.2$; chloroform).

C) 5-Chloro-1-[(2,4-dimethoxyphenyl)sulphonyl]-3-(2-isopropoxyphenyl)-2-oxo-2,3-dihydro-1H-indol-3-yl phenyl carbamate, single isomer A mixture of 2.103 g of the compound obtained in the preceding step and 3.5 ml of pyridine in 20 ml of DCM is cooled to 0° C., 0.665 ml of phenyl chloroformate is added and the mixture is left under cold conditions for 36 hours. The resulting mixture is concentrated under vacuum, the residue is taken up in 5% K$_2$CO$_3$ solution and extracted with EtOAc, the organic phase is washed with water and with saturated NaCl solution and dried over Na$_2$SO$_4$, and the solvent is evaporated off under vacuum. The residue is chromatographed on silica gel, eluting with a DCM/hexane mixture (80/20; v/v). 1.88 g of the expected product are obtained, and are used without further purification.

Preparation 1.22

5-Chloro-1-[(2,4-dimethoxyphenyl)sulphonyl]-3-(2,5-dimethoxyphenyl)-2-oxo-2,3-dihydro-1H-indol-3-yl phenyl carbamate (II): R$_1$=Cl; R$_2$=H; R$_3$=OCH$_3$; R$_4$=5-OCH$_3$, X=—NH—;

Y = 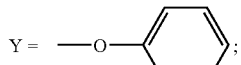

W = 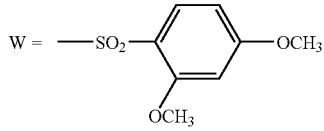

A) 3,5-Dichloro-3-(2,5-dimethoxyphenyl)-1,3-dihydro-2H-indol-2-one

A mixture of 3 g of the compound obtained in step A of Preparation 1.17 and 1.2 ml of pyridine in 50 ml of DCM is cooled to a temperature below 20° C., 0.8 ml of thionyl chloride is added and the mixture is stirred for 1 hour. The reaction mixture is washed with water, the organic phase is dried over Na$_2$SO$_4$ and the solvent is evaporated off under vacuum. The residue is chromatographed on silica gel, eluting with DCM. 1.9 g of the expected product are obtained, and are used without further purification.

B) 3-Amino-5-chloro-3-(2,5-dimethoxyphenyl)-1,3-dihydro-2H-indol-2-one

A mixture of 1.25 g of the compound obtained in the preceding step in 7 ml of THF is cooled to 0° C., ammonia gas is bubbled through for 4 times 10 minutes over 6 hours and the mixture is stirred at RT for 24 hours. The resulting mixture is concentrated under vacuum, the residue is taken up in DCM and the solvent is evaporated off under vacuum. The residue is chromatographed on silica gel, eluting with DCM and then with a DCM/EtOAc mixture (60/40; v/v). 0.808 g of the expected product is obtained, and is used without further purification.

C) 3-Amino-5-chloro-1-[(2,4-dimethoxyphenyl)sulphonyl]-3-(2,5-dimethoxyphenyl)-1,3-dihydro-2H-indol-2-one This compound is prepared according to the procedure described in step D of Preparation 1.19, starting with 0.749 g of the compound obtained in the preceding step, 0.113 g of 60% sodium hydride in oil, 7 ml of DMF and 0.612 g of 2,4-dimethoxybenzene-sulphonyl chloride. 0.9 g of the expected product is obtained after crystallization from a DCM/iso ether mixture, m.p.=191° C.

D) 5-Chloro-1-[(2,4-dimethoxyphenyl)sulphonyl]-3-(2,5-dimethoxyphenyl)-2-oxo-2,3-dihydro-1H-indol-3-yl phenyl carbamate A mixture of 0.52 g of the compound obtained in the preceding step and 1 ml of pyridine in 5 ml of DCM is cooled to 0° C., 0.16 ml of phenyl chloroformate is added and the mixture is stirred for 16 hours. Water is added to the reaction mixture, the DCM is evaporated off under vacuum, the residue is extracted with EtOAc, the organic phase is washed with 5% K$_2$CO$_3$ solution, with water and with saturated NaCl solution and dried over Na$_2$SO$_4$, and the solvent is evaporated off under vacuum. The residue is chromatographed on silica gel, eluting with DCM. 0.46 g of the expected product is obtained, and is used without further purification.

Preparation 1.23

5-Chloro-3-(2-chlorophenyl)-1-[(2,4-dimethoxyphenyl)sulphonyl]-2-oxo-2,3-dihydro-1H-indol-3-yl phenyl carbamate (II): $R_1$=Cl; $R_2$=H; $R_3$=Cl; $R_4$=H; X=—NH—;

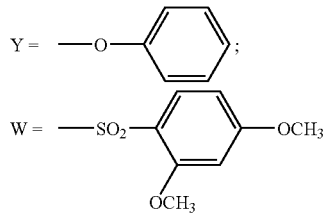

A) 3-Amino-5-chloro-3-(2-chlorophenyl)-1-[(2,4-dimethoxyphenyl)sulphonyl]-1,3-dihydro-2H-indol-2-one This compound is prepared according to the procedure described in WO 95/18105 in Example 3.

B) 5-Chloro-3-(2-chlorophenyl)-1-[(2,4-dimethoxyphenyl)sulphonyl]-2-oxo-2,3-dihydro-1H-indol-3-yl phenyl carbamate A solution of 3 g of the compound obtained in the preceding step in 25 ml of pyridine is cooled to 0° C., a solution of 1.25 g of phenyl chloroformate in 2 ml of DCM is added dropwise and the mixture is stirred at 0° C. for 3 hours and then at RT overnight. The mixture is cooled again to 0° C., 0.96 g of phenyl chloroformate is added and the mixture is left under cold conditions for 18 hours. The resulting mixture is concentrated under vacuum, the residue is taken up in 5% $K_2CO_3$ solution and extracted with EtOAc, the organic phase is dried over $Na_2SO_4$ and the solvent is evaporated off under vacuum. The residue is chromatographed on silica gel, eluting with a DCM/EtOAc mixture (95/5; v/v). 2.88 g of the expected product are obtained.

Preparation 1.24

5-Chloro-1-[(2,4-dimethoxyphenyl)sulphonyl]-3-(2-methoxyphenyl)-6-methyl-2-oxo-2,3-dihydro-1H-indol-3-yl phenyl carbamate (II): $R_1$=Cl; $R_2$=6-$CH_3$; $R_3$=$OCH_3$; $R_4$=H, X=—NH—;

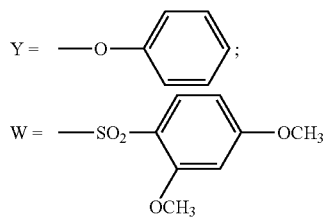

A) 3,5-Dichloro-3-(2-methoxyphenyl)-6-methyl-1,3-dihydro-2H-indol-2-one

A mixture of 2.0 g of the compound obtained in step B of Preparation 1.6 in 45 ml of DCM is cooled to 0° C., 0.77 ml of pyridine is added, followed by addition of 1.17 g of thionyl chloride, and the mixture is stirred for 2 hours after allowing the temperature to return to RT. Water and DCM are added to the reaction mixture and, after separation of the phases by settling, the organic phase is washed four times with water and dried over $Na_2SO_4$, and the solvent is evaporated off under vacuum. The expected product is obtained, and is used without further purification.

B) 3-Amino-5-chloro-3-(2-methoxyphenyl)-6-methyl-1,3-dihydro-2H-indol-2-one

Ammonia gas is bubbled for 30 minutes at RT into a mixture of 3.4 g of the compound obtained in the preceding step in 25 ml of DCM, and the resulting mixture is stirred for 18 hours. The mixture is concentrated under vacuum, the residue is extracted with EtOAc, the organic phase is washed with saturated NaCl solution and dried over $Na_2SO_4$, and the solvent is evaporated off under vacuum. The residue is chromatographed on silica gel, eluting with a DCM/MeOH mixture (95/5; v/v). 2 g of the expected product are obtained.

C) 3-Amino-5-chloro-1-[(2,4-dimethoxyphenyl)sulphonyl]-3-(2-methoxyphenyl)-6-methyl-1,3-dihydro-2H-indol-2-one This compound is obtained according to the procedure described in step B of Preparation 1.18, starting with 2 g of the compound obtained in the preceding step, 0.29 g of 60% sodium hydride in oil, 15 ml of DMF and 1.54 g of 2,4-dimethoxybenzene-sulphonyl chloride. 3.2 g of the expected product are obtained.

D) 5-Chloro-1-[(2,4-dimethoxyphenyl)sulphonyl]-3-(2-methoxyphenyl)-6-methyl-2-oxo-2,3-dihydro-1H-indol-3-yl phenyl carbamate A solution of 3.2 g of the compound obtained in the preceding step and 10 ml of pyridine in 30 ml of DCM is cooled to 4° C., 1.2 ml of phenyl chloroformate are added dropwise and the mixture is stirred at RT for 2 hours. The resulting mixture is concentrated under vacuum, the residue is extracted with EtOAc, the organic phase is washed with 5% $KHSO_4$ solution, with 5% $Na_2CO_3$ solution, with water and with saturated NaCl solution and dried over $Na_2SO_4$, and the solvent is evaporated off under vacuum. 2.3 g of the expected product are obtained after crystallization from a DCM/iso ether mixture.

Preparation 1.25

5-Chloro-1-[(2,4-dimethoxyphenyl)sulphonyl]-3-(2-methoxyphenyl)-6-trifluoromethyl-2-oxo-2,3-dihydro-1H-indol-3-yl phenyl carbamate, single isomer (II): $R_1$=Cl; $R_2$=6-$CF_3$; $R_3$=$OCH_3$; $R_4$=H; X=—NH—;

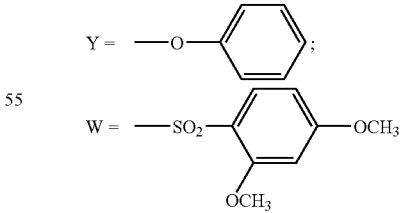

A) 5-Chloro-3-hydroxy-3-(2-methoxyphenyl)-6-trifluoromethyl-1,3-dihydro-2H-indol-2-one a) tert-Butyl 4-chloro-3-trifluoromethyl-phenyl carbamate This compound is prepared according to the procedure described in step B a) of Preparation 1.6, starting with 4-chloro-3-trifluoromethylaniline and di-tert-butyl dicarbonate in dioxane. The expected product is obtained in the form of an oil that solidifies, m.p.=90° C.

b) A solution of 4 g of tert-butyl 4-chloro-3-trifluoromethylphenyl carbamate in 30 ml of ether is cooled to −70° C., under an argon atmosphere, 22 ml of a 1.5M solution of tert-butyllithium in pentane are added dropwise and the mixture is stirred for 1 hour while allowing the temperature to rise to −10° C., and is stirred for 2 hours 30 minutes at −10° C. The reaction mixture is cooled to −70° C., a solution of 3.05 g of the compound obtained in step A of Preparation 1.6 in 15 ml of THF is added dropwise and the mixture is stirred for 1 hour while allowing the temperature to rise to −30° C., and then for 16 hours while allowing the temperature to return to RT. Saturated NH$_4$Cl solution is added to the reaction mixture, the ether and THF are evaporated off, the resulting aqueous phase is extracted with EtOAc, the organic phase is washed with water and with saturated NaCl solution and dried over Na$_2$SO$_4$, and the solvent is evaporated off under vacuum. The residue is chromatographed on silica gel, eluting with DCM and then with a DCM/EtOAc mixture (90/10; v/v). 1.48 g of the expected product are obtained after crystallization from an iso ether/hexane mixture, m.p.=230–231° C.

B) 3,5-Dichloro-3-(2-methoxyphenyl)-6-trifluoromethyl-1,3-dihydro-2H-indol-2-one A suspension of 1.3 g of the compound obtained in step A in 8 ml of DCM is cooled to 0° C., 0.43 ml of pyridine is added, followed by addition of 0.4 ml of thionyl chloride, and the mixture is stirred for 15 minutes. The reaction mixture is washed three times with water, the organic phase is dried over Na$_2$SO$_4$ and the solvent is evaporated off under vacuum. 1.2 g of the expected product are obtained, and are used without further purification.

C) 5-Chloro-3-[[(1S)-2-hydroxy-1-phenylethyl]amino]-3-(2-methoxyphenyl)-6-trifluoromethyl-1,3-dihydro-2H-indol-2-one, isomer A and isomer B A mixture of 1.29 g of the compound obtained in the preceding step and 0.47 g of (S)-(+)-α-phenyl-glycinol in 35 ml of chloroform is stirred at RT for 4 hours. 0.6 ml of DIPEA is then added, the solvent is concentrated by half and the mixture is stirred at RT for 22 hours. The reaction mixture is concentrated under vacuum and the residue is chromatographed on silica gel, eluting with a DCM/EtOAc mixture (85/15; v/v). One diastereoisomer is separated out: the less polar, isomer A: 0.712 g is obtained after crystallization from a DCM/iso ether mixture, m.p.=205° C.

$$\alpha_D^{20} = +164° \ (c = 0.16; \text{chloroform}).$$

The chromatography is continued, eluting with a DCM/EtOAc mixture (70/30; v/v) and the other diastereoisomer is separated out:
the more polar, isomer B: 0.45 g is obtained, m.p.=242° C.

$$\alpha_D^{20} = -55° \ (c = 0.15 \text{ chloroform}).$$

D) 3-Amino-5-chloro-3-(2-methoxyphenyl)-6-trifluoromethyl-1,3-dihydro-2H-indol-2-one, single isomer A solution of 0.7 g of the compound obtained in the preceding step (isomer A) in 15 ml of DCM and 7 ml of MeOH is cooled to 0° C., 0.907 g of lead tetraacetate is added and the mixture is stirred for 40 minutes. A few drops of 5% NaHCO$_3$ solution are added and the mixture is concentrated under vacuum. The residue is taken up in water and extracted 3 times with EtOAc, the organic phase is washed with water and with saturated NaCl solution and dried over Na$_2$SO$_4$, and the solvent is evaporated off under vacuum. The product obtained is taken up in 30 ml of water, 30 ml of 5N HCl solution are added dropwise, followed by addition of THF until dissolution is complete, and the mixture is stirred for 1 hour. The reaction mixture is diluted with 50 ml of water, the aqueous phase is washed with 150 ml of ether and basified to pH 12 by addition of K$_2$CO$_3$ and then concentrated NaOH solution, and is extracted with EtOAc, the organic phase is dried over Na$_2$SO$_4$ and the solvent is evaporated off under vacuum. The residue is chromatographed on silica gel, eluting with a DCM/MeOH mixture (92/8; v/v). 0.19 g of the expected product is obtained.

E) 3-Amino-5-chloro-1-[(2,4-dimethoxyphenyl)sulphonyl]-3-(2-methoxyphenyl)-6-trifluoromethyl-1,3-dihydro-2H-indol-2-one, single isomer This compound is prepared according to the procedure described in step B of Preparation 1.18, starting with 0.19 g of the compound obtained in the preceding step, 0.023 g of 60% sodium hydride in oil, 2 ml of DMF and 0.138 g of 2,4-dimethoxybenzene-sulphonyl chloride. 0.22 g of the expected product is obtained.

F) 5-Chloro-1-[(2,4-dimethoxyphenyl)sulphonyl]-3-(2-methoxyphenyl)-6-trifluoromethyl-2-oxo-2,3-dihydro-1H-indol-3-yl phenyl carbamate, single isomer This compound is prepared according to the precedure described in step C of Preparation 1.18, starting with 0.215 g of the compound obtained in the preceding step, 0.31 ml of pyridine, 5 ml of DCM and 0.079 g of phenyl chloroformate. 0.208 g of the expected product is obtained.

Preparation 1.26

6-Chloro-3-(2-chlorophenyl)-1-[(2,4-dimethoxyphenyl)sulphonyl]-5-methyl-2-oxo-2,3-dihydro-1H-indol-3-yl phenyl carbamate (II): R$_1$=CH$_3$; R$_2$=6-Cl; R$_3$=Cl; R$_4$=H; X=—NH—;

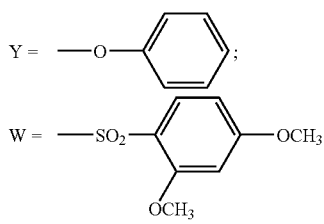

A) N-(3-Chloro-4-methylphenyl)-DL-2-chloromandelamide

A mixture of 52.72 g of DL-2-chloromandelic acid and 40 g of 3-chloro-4-methylaniline in 400 ml of 1,2-dichlorobenzene is refluxed for 6 hours, while removing the water formed using Dean-Stark apparatus. After cooling to RT, the mixture is left to crystallize and the precipitate formed is filtered off by suction. The expected product is obtained after recrystallization from a DCM/iso ether mixture, m.p.=164° C.

B) 6-Chloro-3-(2-chlorophenyl)-5-methyl-1,3-dihydroindol-2-one 102 ml of concentrated (95%) $H_2SO_4$ are cooled to 5° C. and 23 ml of fuming sulphuric acid (30% oleum) are added dropwise. 25 g of the compound obtained in the preceding step are then added portionwise, at a temperature below 5° C., and the mixture is stirred at RT for 48 hours. The reaction mixture is poured into an ice/water mixture, the precipitate formed is filtered off by suction and washed with water to pH 7. The precipitate is dissolved in EtOAc, the organic phase is washed with saturated NaCl solution and dried over $Na_2SO_4$, the solvent is partially evaporated off under vacuum and the precipitate formed is filtered off by suction. The expected product is obtained, m.p.=186° C.

C) 3-Bromo-6-chloro-3-(2-chlorophenyl)-5-methyl-1,3-dihydro-2H-indol-2-one

A solution of 2.6 ml of bromine in 10 ml of DCM is added slowly, at RT, to a suspension of 16.36 g of the compound obtained in the preceding step in 200 ml of DCM. A further addition of a solution of 0.26 ml of bromine in 5 ml of DCM is made and the reaction mixture is then concentrated under vacuum. The residue is taken up twice in DCM and the solvent is evaporated off each time under vacuum. The residue is dissolved in EtOAc, the organic phase is washed with saturated NaCl solution and dried over $MgSO_4$, and the solvent is evaporated off under vacuum. The expected product is obtained.

D) 3-Amino-6-chloro-3-(2-chlorophenyl)-5-methyl-1,3-dihydro-2H-indol-2-one 30 ml of concentrated aqueous ammonia solution are added to a solution of 4.25 g of the compound obtained in the preceding step in 30 ml of THF, and the mixture is stirred at RT for 24 hours. A further 10 ml of concentrated aqueous ammonia solution are added and the mixture is stirred at RT overnight. The resulting mixture is concentrated under vacuum, the residue is extracted with DCM, the organic phase is washed with water and dried over $Na_2SO_4$, and the solvent is evaporated off under vacuum. 3.02 g of the expected product are obtained after crystallization from DCM, m.p.=233° C.

E) 3-Amino-6-chloro-3-(2-chlorophenyl)-1-[(2,4-dimethoxyphenyl)sulphonyl]-5-methyl-1,3-dihydro-2H-indol-2-one This compound is prepared according to the procedure described in step B of Preparation 1.18, starting with 0.54 g of the compound obtained in the preceding step, 0.077 g of 60% sodium hydride in oil, 5 ml of DMF and 0.435 g of 2,4-dimethoxybenzene-sulphonyl chloride. 0.592 g of the expected product is obtained after crystallization from a DCM/iso ether mixture.

F) 6-Chloro-3-(2-chlorophenyl)-1-[(2,4-dimethoxyphenyl)sulphonyl]-5-methyl-2-oxo-2,3-dihydro-1H-indol-3-yl phenyl carbamate This compound is prepared according to the procedure described in step C of Preparation 1.18, starting with 0.592 g of the compound obtained in the preceding step, 1 ml of pyridine, 6 ml of DCM and 0.19 ml of phenyl chloroformate. 0.690 g of the expected product is obtained, and is used without further purification.

Preparation 1.27

2-[[5-Chloro-3-(2-isopropoxyphenyl)-2-oxo-2,3-dihydro-1H-indol-3-yl]oxy]acetic acid II: $R_1$=Cl, $R_2$=H, $R_3$=—OCH($CH_3$)$_2$; $R_4$=H; X=—O—$CH_2$—; Y=OH; W=H A) Methyl 2-[[5-chloro-3-(2-isopropoxyphenyl)-2-oxo-2,3-dihydro-1H-indol-3-yl]oxy]acetate 0.29 g of 60% sodium hydride in oil is added to a solution of 1.05 g of methyl glycolate in 20 ml of THF, and the mixture is stirred at RT for 10 minutes. A solution of 1.88 g of the compound obtained in step A of Preparation 1.20 are then added dropwise and the mixture is stirred at RT for 10 minutes. The resulting mixture is concentrated under vacuum, the residue is extracted with EtOAc, the organic phase is washed with water and with 1N HCl solution and dried over $Na_2SO_4$, and the solvent is evaporated off under vacuum. The residue is chromatographed on silica gel, eluting with DCM and then with EtOAc. 0.8 g of the expected product is obtained after crystallization from iso ether, m.p.=-210–2130C.

B) 2-[[5-Chloro-3-(2-isopropoxyphenyl)-2-oxo-2,3-dihydro-1H-indol-3-yl]oxy]acetic acid A solution of 0.24 g of NaOH pellets in 5 ml of water is added, at 20° C., to a solution of 0.8 g of the compound obtained in the preceding step in 40 ml of MeOH, and the mixture is stirred at RT for 15 hours. The resulting mixture is concentrated under vacuum, the residue is dissolved in 25 ml of water and acidified by dropwise addition of 1 ml of 12N HCl, and the precipitate formed is filtered off by suction. 0.8 g of the expected product is obtained, m.p.=225–228° C.

Preparation 1.28

2-[5-Chloro-1-[(2,4-dimethoxyphenyl)sulphonyl]-3-(2-methoxyphenyl)-2-oxo-2,3-dihydro-1H-indol-3-yl]amino]acetic acid (II): $R_1$=Cl; $R_2$=H; $R_3$=—OCH$_3$; $R_4$=H; X=—NH—$CH_2$—; Y=OH;

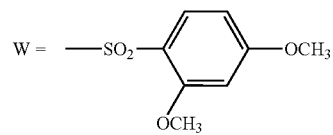

A) tert-Butyl 2-[[5-chloro-3-(2-methoxyphenyl)-2-oxo-2,3-dihydro-1H-indol-3-yl]ammonia]-acetate A solution of 2.4 g of glycine tert-butyl ester hydrochloride in 50 ml of chloroform and 50 ml of THF is cooled in an ice bath, 2.3 g of triethylamine are added, followed by addition of 3.5 g of the compound obtained in step A of Preparation 1.19, and the mixture is stirred at RT overnight. The resulting mixture is concentrated under vacuum, the residue is taken up in water and extracted with DCM, the organic phase is dried over $Na_2SO_4$ and the solvent is evaporated off under vacuum. The residue is triturated in iso ether and the precipitate formed is filtered off by suction. 2.2 g of the expected product are obtained.

B) tert-Butyl 2-[[5-chloro-1-[(2,4-dimethoxyphenyl)sulphonyl]-3-(2-methoxyphenyl)-2-oxo-2,3-dihydro-1H-indol-3-yl]amino]acetate 0.225 g of 60% sodium hydride in oil is added to a mixture of 2.1 g of the compound obtained in the preceding step in 10 ml of DMF, and the mixture is stirred at RT for 30 minutes. 1.2 g of 2,4-dimethoxybenzenesulphonyl chloride are then added and the mixture is stirred at RT for 18 hours. The reaction mixture is poured into water and extracted with EtOAc, the organic phase is dried over $Na_2SO_4$ and the solvent is evaporated off under vacuum. The residue is chromatographed on silica gel, eluting with DCM. 2.5 g of the expected product are obtained after crystallization from iso ether.

C) 2-[[5-Chloro-1-[(2,4-dimethoxyphenyl)sulphonyl]-3-(2-methoxyphenyl)-2-oxo-2,3-dihydro-1H-indol-3-yl]amino] acetic acid A mixture of 2.5 g of the compound obtained in the preceding step and 10 ml of TFA is stirred for 3 hours. The mixture is concentrated under vacuum, the residue is taken up in hexane and the precipitate formed is filtered off by suction. 2 g of the expected product are obtained.

Preparation 1.29

3-[[5-Chloro-1-[(2,4-dimethoxyphenyl)sulphonyl]-3-(2-methoxyphenyl)-2-oxo-2,3-dihydro-1H-indol-3-yl]amino]propionic acid (II): $R_1$=Cl; $R_2$=H; $R_3$=—$OCH_3$; $R_4$=H; X=—NH—$CH_2$—$CH_2$—; Y=OH;

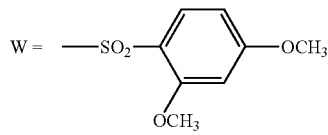

A) tert-Butyl 3-[[5-chloro-3-(2-methoxyphenyl)-2-oxo-2,3-dihydro-1H-indol-3-yl]amino]-propionate 2.15 g of triethylamine are added to a mixture of 3 g of the compound obtained in step A of Preparation 1.19 and 2.1 g of β-alanine tert-butyl ester hydrochloride in 50 ml of DCM and 50 ml of THF, and the mixture is stirred at RT for 18 hours. The resulting mixture is concentrated under vacuum, the residue is extracted with EtOAc, the organic phase is washed with water and dried over $Na_2SO_4$, and the solvent is evaporated off under vacuum. The residue is chromatographed on silica gel, eluting with a DCM/EtOAc mixture (80/20; v/v). 3.2 g of the expected product are obtained after crystallization from a DCM/iso ether mixture, m.p.=170° C.

B) tert-Butyl 3-[[5-chloro-1-[(2,4-dimethoxyphenyl)sulphonyl]-3-(2-methoxyphenyl)-2-oxo-2,3-dihydro-1H-indol-3-yl]amino]propionate This compound is prepared according to the procedure described in step B of Preparation 1.28, starting with 2.16 g of the compound obtained in the preceding step, 0.225 g of 60% sodium hydride in oil, 15 ml of DMF and 1.21 g of 2,4-dimethoxybenzene-sulphonyl chloride. 2.4 g of the expected product are obtained after crystallization from a heptane/EtOAc mixture, m.p.=175° C.

C) 3-[[5-Chloro-1-[(2,4-dimethoxyphenyl)sulphonyl]-3-(2-methoxyphenyl)-2-oxo-2,3-dihydro-1H-indol-3-yl]amino] propionic acid A mixture of 2.4 g of the compound obtained in the preceding step and 15 ml of TFA in 5 ml of DCM is stirred for 18 hours. The mixture is concentrated under vacuum, the residue is taken up in ether and the precipitate formed is filtered off by suction. 2.2 g of the expected product are obtained, m.p.>250° C.

Preparation 1.30

2-[5-Chloro-3-(2-fluorophenyl)-2-oxo-2,3-dihydro-1H-indol-3-yl]acetic acid, dextrorotatory isomer (II): $R_1$=Cl; $R_2$=H; $R_3$=—F; $R_4$=H; X=—$CH_2$—; Y=OH; W=H A) Ethyl 2-[5-chloro-3-(2-fluorophenyl)-2-oxo-2,3-dihydro-1H-indol-3-yl]acetate A mixture of 2.6 g of the compound obtained in step C of Preparation 1.12, 1.84 g of ethyl bromoacetate, 1.66 g of KI and 2 g of $K_2CO_3$ in 10 ml of acetone is refluxed for 20 hours. The mineral salts are filtered off and the filtrate is concentrated under vacuum. The residue is chromatographed on silica gel, eluting with DCM and then with EtOAc. 2.1 g of the expected product are obtained after precipitation from iso ether.

B) 2-[5-Chloro-3-(2-fluorophenyl)-2-oxo-2,3-dihydro-1H-indol-3-yl]acetic acid

A mixture of 2 g of the compound obtained in the preceding step and 2 ml of 30% NaOH solution in 1 ml of water and 50 ml of EtOH is stirred at RT for 20 hours. The mixture is concentrated under vacuum, the residue is taken up in 40 ml of water and acidifed to pH 1 by-addition of concentrated HCl, and the precipitate formed is filtered off by suction and washed with water. 1.9 g of the expected product are obtained.

C) 2-[5-Chloro-3-(2-fluorophenyl)-2-oxo-2,3-dihydro-1H-indol-3-yl]acetic acid, dextrorotatory isomer A mixture of 0.97 g of the compound obtained in the preceding step and 0.89 g of (+)-cinchonine $$\left(\alpha_D^{20} = +225° \text{ C.}; c = 0.5; \text{EtOH}\right)$$

in 31.5 ml of MeOH is heated to 40° C., and then heated to reflux. The precipitate formed is filtered off by suction while hot and washed with hot MeOH and then with ether to give 0.485 g of the salt with (+)-cinchonine. 0.485 g of the salt thus obtained is taken up in a water/EtOAc mixture, acidified to pH 0 by addition of 3N HCl, stirred and extracted with EtOAc, the organic phase is washed with water and dried over $Na_2SO_4$, and the solvent is evaporated off under vacuum. 0.22 g of the expected product is obtained in the form of the dextrorotatory isomer.

$$\alpha_D^{20} = +61.3° \ (c = 0.15; \text{chloroform}).$$

Preparation 1.31

2-[5,6-Dichloro-3-(2-fluorophenyl)-2-oxo-2,3-dihydro-1H-indol-3-yl] acetic acid (II): $R_1$=Cl; $R_2$=6-Cl; $R_3$=F; $R_4$=H; X=—$CH_2$—; Y=OH, W=H.

A) N-(3,4-dichlorophenyl)-DL-2-fluoromandelamide

A mixture of 7.5 g of the compound obtained in step A of Preparation 1.12 and 7.5 g of 3,4-dichloroaniline in 40 ml of 1,2-dichlorobenzene is refluxed for 3 hours, while removing the water formed with the aid of Dean-Stark apparatus. The mixture is concentrated under vacuum, the residue is taken up in iso ether and the precipitate formed is filtered off by suction. 9 g of the expected product are obtained.

B) 5,6-Dichloro-3-(2-fluorophenyl)-1,3-dihydro-2H-indol-2-one 8.9 g of the compound obtained in the preceding step are added, at RT, to a mixture of 36 ml of concentrated (95%) $H_2SO_4$ and 9 ml of fuming sulphuric acid (30% oleum), and the mixture is then stirred for 8 hours. The reaction mixture is poured into an ice/water mixture and the precipitate formed is filtered off by suction and washed with water. The precipitate is chromatographed on silica gel, eluting with DCM and then with iso ether. The two isomers are separated: the less polar, compound of step B gives 3.7 g, m.p.=204–205° C.;

the more polar, 4,5-dichloro-3-(2-fluorophenyl)-1,3-dihydro-2H-indol-2-one gives 1.5 g, m.p.=244–247° C.

B) Ethyl 2-[5,6-dichloro-3-(2-fluorophenyl)-2-oxo-2,3-dihydro-1H-indol-3-yl]acetate A mixture of 3 g of the compound obtained in the preceding step, 1.7 g of ethyl bromoacetate, 1.8 g of KI and 1.4 g of $K_2CO_3$ in 20 ml of acetone is refluxed for 10 hours. The mixture is concentrated under vacuum, the residue is taken up in water and extracted with EtOAc, the organic phase is dried over $Na_2SO_4$ and the solvent is evaporated off under vacuum. The residue is chromatographed on silica gel, eluting with iso ether. 2.1 g of the expected product are obtained after trituration in pentane and then in iso ether, m.p.=152–158° C.

C) 2-[5,6-Dichloro-3-(2-fluorophenyl)-2-oxo-2,3-dihydro-1H-indol-3-yl]acetic acid A mixture of 2 g of the compound obtained in the preceding step and 3 ml of 30% NaOH solution in 5 ml of water and 40 ml of EtOH is stirred at RT for 20 hours. The mixture is concentrated under vacuum, the residue is taken up in water, the aqueous phase is washed with ether, acidified to pH 1 by addition of concentrated HCl and extracted with EtOAc, the organic phase is dried over $Na_2SO_4$ and the solvent is evaporated off under vacuum. 1.5 g of the expected product are obtained after trituration in iso ether, m.p.=245° C.

Preparation 1.32

2-[5-Chloro-3-(2,3-dimethoxyphenyl)-2-oxo-2,3-dihydro-1H-indol-3-yl]acetic acid (II): $R_1$=Cl; $R_2$=H; $R_3$=OCH$_3$; $R_4$=3-OCH$_3$; X=—$CH_2$—; Y=OH; W=H A) Ethyl 2-(2,3-Dimethoxyphenyl)-2-oxoacetate A mixture of 27.6 g of 1,2-dimethoxybenzene in 160 ml of ether is cooled to −40° C., 250 ml of a 1.6M solution of n-butyllithium in hexane are added dropwise and the mixture is then stirred for 24 hours while allowing the temperature to return to RT. The reaction mixture is cooled to −20° C., 136 ml of diethyl oxalate are added quickly and the mixture is stirred while allowing the temperature to return to RT. After stirring for 30 minutes at RT, the reaction mixture is poured into saturated $NH_4Cl$ solution, the phases are separated by settling, the aqueous phase is extracted with ether, the combined organic phases are washed twice with water and dried over $Na_2SO_4$, and the solvents are evaporated off under vacuum. The excess diethyl oxalate is removed by distillation under vacuum (b.p.=90° C. at 2400 Pa). The resulting crude product is chromatographed on silica gel, eluting with a heptane/iso ether mixture (90/10; v/v). 25 g of the expected product are obtained, and are used without further purification in the following step.

B) 5-Chloro-3-hydroxy-3-(2,3-dimethoxyphenyl)-1,3-dihydro-2H-indol-2-one a) tert-Butyl 4-chlorophenylcarbamate A mixture of 12.7 g of 4-chloroaniline and 22 g of di-tert-butyl dicarbonate in 60 ml of dioxane is stirred at RT for 24 hours. The reaction mixture is concentrated under vacuum, the residue is taken up in pentane and the precipitate formed is filtered off by suction and dried. 22.5 g of the expected product are obtained.

b) A mixture of 11.4 g of tert-butyl 4-chlorophenylcarbamate in 100 ml of ether is cooled to −40° C., under an atmosphere of dry nitrogen, 80 ml of a 1.5M solution of tert-butyllithium in pentane are added dropwise and the mixture is stirred at −20° C. for 3 hours. The reaction mixture is cooled to −40° C., a solution of 14 g of the compound obtained in step A in 50 ml of THF is added over 1 hour, and the mixture is stirred at RT for 4 days. The reaction mixture is poured into saturated $NH_4Cl$ solution and the precipitate formed is filtered off by suction and dried. 10.2 g of the expected product are obtained, and are used without further purification in the following step.

C) 5-Chloro-3-(2,3-dimethoxyphenyl)-1,3-dihydro-2H-indol-2-one

A mixture of 8.5 g of the compound obtained in the preceding step, 40 ml of TFA and 11.5 ml of triethylsilane is refluxed for 5 hours. The mixture is concentrated under vacuum, the residue is taken up in water and extracted with EtOAc, the precipitate formed is filtered off by suction and washed with EtOAc and then with iso ether, to give 5.1 g of the expected product. The filtration liquors are separated out by settling, the organic phase is dried over $Na_2SO_4$ and the solvent is evaporated off under vacuum. A further 1.4 g of the expected product are obtained after crystallization from EtOAc, m.p.=193° C.

D) Ethyl 2-[5-chloro-3-(2,3-dimethoxyphenyl)-2-oxo-2,3-dihydro-1H-indol-3-yl]acetate A mixture of 6.2 g of the compound obtained in the preceding step, 3.6 g of ethyl bromoacetate, 3.5 g of KI and 6.2 g of $K_2CO_3$ in 20 ml of DMF is heated at 60° C. for 8 hours. The mixture is concentrated under vacuum, the residue is taken up in water and extracted with EtOAc, the organic phase is washed with water, dried over $Na_2SO_4$ and evaporated under vacuum. The residue is chromatographed on silica gel, eluting with a DCM/MeOH mixture (99/1; v/v). 3 g of the expected product are obtained, m.p.=155° C.

E) 2-[5-Chloro-3-(2,3-dimethoxyphenyl)-2-oxo-2,3-dihydro-1H-indol-3-yl]acetic acid A mixture of 3 g of the compound obtained in the preceding step and 0.5 g of NaOH pellets in 40 ml of water and 10 ml of dioxane is stirred at RT for 24 hours. 150 ml of water are added, the aqueous phase is washed with EtOAc and acidified to pH 1 by addition of concentrated HCl, and the precipitate formed is filtered off by suction, washed with water and dried. 2.5 g of the expected product are obtained, m.p.=235° C.

Preparation 1.33

2-[5-Chloro-3-(2-ethoxyphenyl)-6-methyl-2-oxo-2,3-dihydro-1H-indol-3-yl]acetic acid (II): $R_1$=Cl; $R_2$=6-$CH_3$; $R_3$=$OCH_2CH_3$; $R_4$=H, X=—$CH_2$—; Y=OH; W=H.

A) 5-Chloro-3-(2-ethoxyphenyl)-3-hydroxy-6-methyl-1,3-dihydro-2H-indol-2-one

This compound is prepared according to the procedure described in step C of Preparation 1.7, starting with the compound obtained in step A of Preparation 1.2 and the compound obtained in step B of Preparation 1.7. 1.05 g of the expected product are obtained, m.p.=253° C.

B) 5-Chloro-3-(2-ethoxyphenyl)-6-methyl-1,3-dihydro-2H-indol-2-one

A mixture of 1.05 g of the compound obtained in the preceding step, 5.5 ml of TFA and 2.2 ml of triethylsilane is refluxed for 5 hours. The mixture is concentrated under vacuum and the residue is chromatographed on silica gel, eluting with DCM and then with a DCM/MeOH mixture (99.5/0.5; v/v). 0.5 g of the expected product is obtained, m.p.=228° C.

C) Ethyl 2-[5-chloro-3-(2-ethoxyphenyl)-6-methyl-2-oxo-2,3-dihydro-1H-indol-3-yl]-acetate This compound is prepared according to the procedure described in step C of Preparation 1.1, starting with 0.5 g of the compound obtained in the preceding step, 0.29 g of ethyl bromoacetate, 0.29 g of KI and 0.46 g of $K_2CO_3$ in 5 ml of acetone. 0.25 g of the expected product is obtained.

D) 2-[5-Chloro-3-(2-ethoxyphenyl)-6-methyl-2-oxo-2,3-dihydro-1H-indol-3-yl]acetic acid This compound is prepared according to the procedure described in step E of Preparation 1.2, starting with 0.25 g of the compound obtained in the preceding step, 0.3 ml of 30% NaOH solution in 2.8 ml of water and 7 ml of THF. 0.2 g of the expected product is obtained.

Preparation 1.34

5-Chloro-1-[(2,4-dimethoxyphenyl)sulphonyl]-3-(2-ethoxyphenyl)-2-oxo-2,3-dihydro-1H-indol-3-yl phenyl carbonate (II): $R_1$=Cl; $R_2$=H; $R_3$=$OCH_2CH_3$; $R_4$=H; X=—O—;

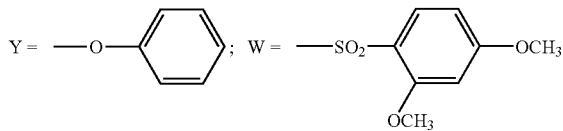

A) 5-Chloro-3-(2-ethoxyphenyl)-3-[(trimethylsilyl)oxy]-1,3-dihydro-2H-indol-2-one This compound is prepared according to the procedure described in step A) of Preparation 1.8, starting with 2 g of the compound of step B of Preparation 1.2, 0.1 g of zinc chloride, 6.6 ml of HMDS and 30 ml of acetonitrile. 1.5 g of the expected product are obtained after trituration in heptane.

B) 5-Chloro-1-[(2,4-dimethoxyphenyl)sulphonyl]-3-(2-ethoxyphenyl)-3-[(trimethylsilyl)oxy]-1,3-dihydro-2H-indol-2-one This compound is prepared according to the procedure described in step B of Preparation 1.8, starting with 1.45 g of the compound obtained in the preceding step, 20 ml of THF, 0.05 g of 60% sodium hydride in oil and 1 g of 2,4-dimethoxybenzenesulphonyl chloride. 1.6 g of the expected product are obtained after trituration in iso ether.

C) 5-Chloro-1-[(2,4-dimethoxyphenyl)sulphonyl]-3-(2-ethoxyphenyl)-3-hydroxy-1,3-dihydro-2H-indol-2-one A mixture of 1.55 g of the compound obtained in the preceding step and 3 ml of 12N HCl in 100 ml of acetone is stirred at RT for 3 hours. The mixture is concentrated under vacuum and the residue is chromatographed on silica gel, eluting with DCM. 1.4 g of the expected product are obtained after trituration in iso ether.

D) 5-Chloro-1-[(2,4-dimethoxyphenyl)sulphonyl]-3-(2-ethoxyphenyl)-2-oxo-2,3-dihydro-1H-indol-3-yl phenyl carbonate.

A mixture of 1.35 g of the compound obtained in the preceding step in 20 ml of pyridine is cooled to 10° C., 2 g of phenyl chloroformate are added and the mixture is stirred for 20 hours, while allowing the temperature to return to RT. The resulting mixture is concentrated under vacuum, the residue is taken up in 1N HCl solution and extracted with iso ether, and the precipitate formed is filtered off by suction and washed with iso ether. 1.8 g of the expected product are obtained, m.p.=210–211° C. (dec.).

Preparations of the compounds of formula (III).

Preparation 2.1

1-(2-Pyrazinyl)piperazine (III): n=1;

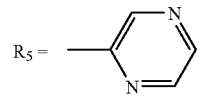

A mixture of 3 g of piperazine, 1.04 ml of 2-chloropyrazine and 1.85 g of $K_2CO_3$ in 100 ml of EtOH is refluxed for 48 hours. The reaction mixture is concentrated under vacuum, the residue is taken up in water and basified to pH 10 by addition of 10% NaOH, and extracted with chloroform, the organic phase is washed with water and dried over $Na_2SO_4$, and the solvent is evaporated off under vacuum. 1.8 g of the expected product are obtained after crystallization from hexane.

Preparation 2.2

1-(3-Pyridyl)piperazine (III): n=1;

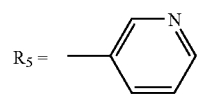

This compound is prepared according to the procedure described in Tetrahedron Letters, 1998, 39, 617–620.

Preparation 2.3

1-(2-Pyridyl)homopiperazine (III): n =2;

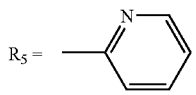

A mixture of 2-bromopyridine and 12 g of homopiperazine is heated at 100° C. for 6 hours. 50 ml of water are added to the reaction mixture and the resulting mixture is extracted with EtOAc, the organic phase is washed with saturated NaCl solution and dried over $Na_2SO_4$, and the solvent is evaporated off under vacuum. 1.28 g of the expected product are obtained.

Preparation 2.4

1-(4-Pyridyl)homopiperazine (III): n–2;

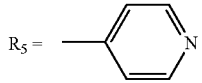

A mixture of 2 g of 4-bromopyridine and 10 g of homopiperazine is heated at 100° C. for 4 hours. 100 ml of water are added to the reaction mixture and the resulting mixture is basified to pH 10 by addition of 10% NaOH solution and extracted three times with 100 ml of chloroform, the organic phase is dried over $Na_2SO_4$ and the solvent is evaporated off under vacuum. 0.9 g of the expected product is obtained.

Preparation 2.5

1-(3-Pyridazinyl)piperazine trihydrochloride (III), 3HCl: n=1;

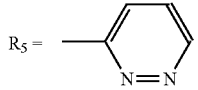

A) tert-Butyl 4-(6-chloro-3-pyridazinyl)-1-piperazinecarboxylate

A mixture of 13.52 g of tert-butyl 1-piperazinecarboxylate, 10.81 g of 3,6-dichloropyridazine and 20 ml of triethylamine in 100 ml of n-butanol is refluxed for 5 hours. The mixture is concentrated under vacuum and the residue is chromatographed on silica gel, eluting with a DCM/EtOAc mixture (90/10; v/v). 14 g of the expected product are obtained, and are used without further purification.

B) tert-Butyl 4-(3-pyridazinyl)-1-piperazinecarboxylate

A mixture of 10.5 g of the compound obtained in the preceding step and 2.5 g of 10% palladium-on-charcoal in 30 ml of DMF and 250 ml of EtOH is hydrogenated overnight at RT and atmospheric pressure. The catalyst is filtered off and the filtrate is concentrated under vacuum. The residue is chromatographed on silica gel, eluting with a DCM/MeOH mixture of from (97/3; v/v) to (90/10; v/v). 9.1 g of the expected product are obtained, and are used without further purification.

C) 1-(3-Pyridazinyl)piperazine trihydrochloride

A mixture of 3.8 g of the compound obtained in the preceding step, 50 ml of 2N HCl solution in ether and 20 ml of MeOH is stirred at RT overnight. The mixture is concentrated under vacuum, the residue is taken up in ether and the precipitate formed is filtered off by suction. 3 g of the expected product are obtained.

Preparation 2.6

1-(1,3-Thiazol-2-yl)piperazine dihydrochloride (III), 2HCl: n=1;

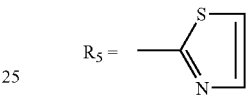

A) tert-Butyl 4-(1,3-thiazol-2-yl)-1-piperazinecarboxylate

A mixture of 5 g of tert-butyl 1-piperazinecarboxylate, 4.4 g of 2-bromo-1,3-thiazole and 7.4 g of $K_2CO_3$ in 50 ml of EtOH is refluxed for 4 days. Water is added to the reaction mixture, the EtOH is evaporated off under vacuum, the resulting aqueous phase is extracted with EtOAc, the organic phase is washed with saturated $K_2CO_3$ solution and with saturated NaCl solution and dried over $Na_2SO_4$, and the solvent is evaporated off under vacuum. The residue is chromatographed on silica gel, eluting with a DCM/MeOH mixture (98/2; v/v). 5 g of the expected product are obtained after precipitation from a cold DCM/hexane mixture and filtration by suction, m.p.=114–116° C.

B) 1-(1,3-Thiazol-2-yl)piperazine dihydrochloride

A mixture of 2.8 g of the compound obtained in the preceding step and 50 ml of 2N HCl solution in ether, to which is added beforehand a minimum amount of DCM and then MeOH until the reaction mixture has dissolved, is stirred at RT for 7 hours. The resulting mixture is concentrated under vacuum to give 2.35 g of the expected product.

EXAMPLE 1

5-Chloro-1-[(2,4-dimethoxyphenyl)sulphonyl]-3-(2-methoxyphenyl)-3-[2-oxo-2-[4-(4-pyridyl)-1-piperazinyl]ethyl]-1,3-dihydro-2H-indol-2-one (I): $R_1$=Cl; $R_2$H; $R_3$=$OCH_3$; $R_4$=H; X=—$CH_2$—; n=1;

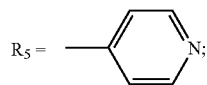

$R_6$=2-$OCH_3$; $R_7$=$OCH_3$

A) 5-Chloro-3-(2-methoxyphenyl)-3-[2-oxo-2-[4-(4-pyridyl)-1-piperazinyl]ethyl]-1,3-dihydro-2H-indol-2-one.

1.7 g of BOP, 2.5 ml of DIPEA and then 0.6 g of 1-(4-pyridyl)piperazine are added, at 20° C., to a mixture of 1.1 g of the compound obtained in Preparation 1.1 in 20 ml of DCM, and the mixture is stirred at 20° C. for 2 hours. 30 ml of 2N NaOH are then added, and the mixture is stirred for 15 minutes. The reaction mixture is extracted with EtOAc, the organic phase is washed with water and dried over Na$_2$SO$_4$ and the solvents are evaporated off under vacuum. The residue is triturated in iso ether and the precipitate formed is filtered off by suction. The precipitate is chromatographed on silica gel, eluting with DCM and then with acetone. 1.4 g of the expected product are obtained after crystallization from iso ether, m.p.=111° C.

B) 5-Chloro-1-[(2,4-dimethoxyphenyl)sulphonyl]-3-(2-methoxyphenyl)-3-[2-oxo-2-[4-(4-pyridyl)-1-piperazinyl]ethyl]-1,3-dihydro-2H-indol-2-one.

0.08 g of 60% sodium hydride in oil is added, at 20° C., to a mixture of 0.7 g of the compound obtained in the preceding step in 15 ml of THF, and the mixture is stirred for 20 minutes. 0.44 g of 2,4-dimethoxybenzenesulphonyl chloride is then added and the mixture is stirred for 1 hour 30 minutes. The reaction mixture is concentrated under vacuum, the residue is extracted with EtOAc, the organic phase is washed with water and dried over Na$_2$SO$_4$, and the solvent is evaporated off under vacuum. The residue is chromatographed on silica gel, eluting with DCM and then with EtOAc and with acetone. 0.7 g of the expected product is obtained after crystallization from iso ether, m.p.=136–141° C. (dec.).

EXAMPLE 2

5-Chloro-3-(2-ethoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one (I): $R_1$=Cl; $R_2$=H; $R_3$=OCH$_2$CH$_3$; $R_4$=H; X=—CH$_2$—; n=1;

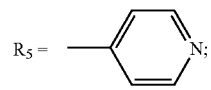

$R_6$=2-OCH$_3$; $R_7$=OCH$_3$

A) 5-Chloro-3-(2-ethoxyphenyl)-3-[2-oxo-2-[4-(4-pyridyl)-1-piperazinyl]ethyl]-1,3-dihydro-2H-indol-2-one A mixture of 1.1 g of the compound obtained in Preparation 1.2, 1.52 g of BOP, 2 ml of DIPEA and 0.6 g of 1-(4-pyridyl)piperazine in 20 ml of DCM is stirred at RT for 24 hours. The crystalline product formed is filtered off by suction and dried to give 0.81 g of the expected product. The filtration liquors are extracted with a concentrated HCl solution, the phases are separated by settling, ice is added to the acidic phase, the acidic phase is basified by addition of 10N NaOH and extracted with EtOAc, the organic phase is washed with water and dried over Na$_2$SO$_4$, and the solvent is evaporated off under vacuum. A further 0.09 g of the expected product is obtained, m.p.=185° C.

B) 5-Chloro-3-(2-ethoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one 0.085 g of 60% sodium hydride in oil is added to a mixture of 0.9 g of the compound obtained in the preceding step in 20 ml of a THF/DMF mixture (90/10; v/v), and the mixture is stirred at RT for 15 minutes. 0.45 g of 2,4-dimethoxybenzenesulphonyl chloride is then added and the mixture is stirred at RT for 30 minutes. The reaction mixture is poured into water and extracted with EtOAc, the organic phase is washed with water and dried over Na$_2$SO$_4$, and the solvent is evaporated off under vacuum. The residue is chromatographed on silica gel, eluting with a DCM/MeOH mixture (96/4; v/v). 0.42 g of the expected product is obtained after crystallization from iso ether, m.p.=225° C.

EXAMPLE 3

5-Chloro-3-(2-isopropoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one, laevorotatory isomer (I): $R_1$=Cl; $R_2$=H; $R_3$=OCH(OCH$_3$)$_2$; $R_4$=H; X=—CH$_2$—; n=1;

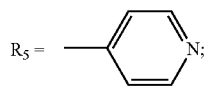

$R_6$=2-OCH$_3$; $R_7$=OCH$_3$

A) 5-Chloro-3-(2-isopropoxyphenyl)-3-[2-oxo-2-[4-(4-pyridyl)-1-piperazinyl]ethyl]-1,3-dihydro-2H-indol-2-one, dextrorotatory isomer.

A mixture of 0.43 g of the compound obtained in Preparation 1.3, 0.6 g of BOP, 0.75 g of DIPEA and 0.2 g of 1-(4-pyridyl)piperazine in 15 ml of DCM is stirred at 20° C. for 2 hours. 25 ml of 2N NaOH are then added and the mixture is stirred at 20° C. for 20 minutes. The reaction mixture is extracted with EtOAc, the organic phase is washed with water and dried over Na$_2$SO$_4$, and the solvent is evaporated off under vacuum. The residue is chromatographed on silica gel, eluting with DCM and then with acetone. 0.33 g of the expected product is obtained.

$$\alpha_D^{20} = +37° \ (c = 0.25; \text{chloroform})$$

B) 5-Chloro-3-(2-isopropoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one, laevorotatory isomer.

0.025 g of 60% sodium hydride in oil is added to a mixture of 0.3 g of the compound obtained in the preceding step in 10 ml of THF, and the mixture is stirred at 20° C. for 15 minutes. 0.19 g of 2,4-dimethoxybenzenesulphonyl chloride is then added and the mixture is stirred at 20° C. for 2 hours. The reaction mixture is concentrated under vacuum, the residue is taken up in water and extracted with EtOAc, the organic phase is dried over Na$_2$SO$_4$ and the solvent is evaporated off under vacuum. The residue is chromatographed on silica gel, eluting with DCM and then with acetone. 0.1 g of the expected product is obtained.

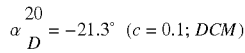

$^1$H NMR: DMSO-$d_6$: δ (ppm): 0.6: d: 3H; 1.2: d: 3H; 3.0 to 4.0: m+2s: 16H; 4.6: mt: 1H; 6.4 to 7.2: mt: 9H; 7.4: bd: 1H; 7.7: dd: 2H; 8.1: d: 2H.

EXAMPLE 4

3-(2-Chlorophenyl)-1-[(2,4-dimethoxyphenyl)sulphonyl]-5-methyl-3-[2-oxo-2-[4-(2-pyridyl)-1-piperazinyl]ethyl]-1,3-dihydro-2H-indol-2-one (I): $R_1$=CH$_3$; $R_2$=H; $R_3$=Cl; $R_4$=H; X=—CH$_2$—; n=1;

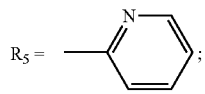

$R_6$=2-OCH$_3$; $R_7$=OCH$_3$

A) 3-(2-Chlorophenyl)-5-methyl-3-[2-oxo-2-[4-(2-pyridyl)-1-piperazinyl]ethyl]-1,3-dihydro-2H-indol-2-one A mixture of 0.26 g of the compound obtained in Preparation 1.4 and 0.2 ml of thionyl chloride in 10 ml of toluene is refluxed for 2 hours and the reaction mixture is then concentrated under vacuum. The acid chloride thus obtained is dissolved in 10 ml of DCM, this solution is added to a mixture of 0.3 g of 1-(2-pyridyl)piperazine in 20 ml of DCM and the mixture is stirred at RT for 2 hours. The reaction mixture is concentrated under vacuum, the residue is extracted with EtOAc, the organic phase is washed with water and dried over Na$_2$SO$_4$, and the solvent is evaporated off under vacuum. The residue is chromatographed on silica gel, eluting with a DCM/MeOH mixture (98/2; v/v). 0.32 g of the expected product is obtained.

B) 3-(2-Chlorophenyl)-1-[(2,4-dimethoxyphenyl)sulphonyl]-5-methyl-3-[2-oxo-2-[4-(2-pyridyl)-1-piperazinyl]ethyl]-1,3-dihydro-2H-indol-2-one 0.0335 g of 60% sodium hydride in oil is added, at RT, to a mixture of 0.3 g of the compound obtained in the preceding step in 10 ml of THF, and the mixture is stirred for 30 minutes. 0.2 g of 2,4-dimethoxybenzenesulphonyl chloride is then added and the mixture is stirred at RT for 1 hour. 50 ml of water are added to the reaction mixture and the resulting mixture is extracted with EtOAc, the organic phase is dried over Na$_2$SO$_4$ and the solvent is evaporated off under vacuum. The residue is chromatographed on silica gel, eluting with a DCM/MeOH mixture (98/2; v/v). 0.32 g of the expected product is obtained after crystallization from iso ether, m.p.=239° C.

EXAMPLE 5

5-Chloro-1-[(2,4-dimethoxyphenyl)sulphonyl]-3-(2-methoxyphenyl)-2-oxo-2,3-dihydro-1H-indol-3-yl 4-(2-pyridyl)-1-piperazinecarboxylate (I): $R_1$=Cl; $R_2$=H; $R_3$=OCH$_3$; $R_4$=H; X=—O—; n=1;

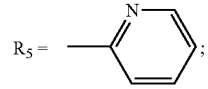

$R_6$=2-OCH$_3$; $R_7$=OCH$_3$

A mixture of 0.5 g of the compound obtained in Preparation 1.8 and 0.3 g of 1-(2-pyridyl)piperazine in 10 ml of DCM is stirred at 20° C. for 20 hours. The reaction mixture is chromatographed on silica gel, eluting with DCM and then with EtOAc. 0.2 g of the expected product is obtained after crystallization from iso ether, m.p.=210–215° C.

EXAMPLE 6

5-Chloro-1-[(2,4-dimethoxyphenyl)sulphonyl]-3-(2-methoxyphenyl)-2-oxo-2,3-dihydro-1H-indol-3-yl 4-(4-pyridyl)-1-piperazinecarboxylate.

(I): $R_1$=Cl; $R_2$=H; $R_3$=OCH$_3$; $R_4$=H; X=—O—; n=1;

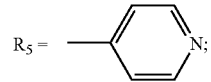

$R_6$=2-OCH$_3$; $R_7$=OCH$_3$.

A mixture of 0.32 g of the compound obtained in Preparation 1.8 and 0.32 g of 1-(4-pyridyl)-piperazine in 15 ml of DCM is stirred at 20° C. for 20 hours. The mixture is concentrated under vacuum, the residue is extracted with EtOAc, the organic phase is washed with 2N NaOH solution and dried over Na$_2$SO$_4$, and the solvent is evaporated off under vacuum. The residue is chromatographed on silica gel, eluting with DCM, then with EtOAc and finally with acetone. 0.25 g of the expected product is obtained after crystallization from iso ether, m.p.=194–198° C.

EXAMPLE 7

5-Chloro-1-((2,4-dimethoxyphenyl)sulphonyl]-3-(2-isopropoxyphenyl)-2-oxo-2,3-dihydro-1H-indol-3-yl 4-(4-pyridyl)-1-piperazinecarboxylate (I): $R_1$=Cl; $R_2$=H; $R_3$=OCH(CH$_3$)$_2$; $R_4$=H; X=—O—; n=1;

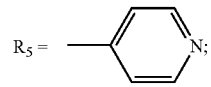

$R_6$=2-OCH$_3$; $R_7$=OCH$_3$

A mixture of 0.66 g of the compound obtained in Preparation 1.9 and 0.45 g of 1-(4-pyridyl)-piperazine in 20 ml of DCM is stirred at RT for 24 hours. The reaction mixture is washed with water, the organic phase is dried over Na$_2$SO$_4$ and the solvent is evaporated off under vacuum. The residue is chromatographed on silica gel, eluting with a DCM/MeOH mixture (99/1; v/v). 0.41 g of the expected product is obtained after crystallization from EtOAc, m.p.=253° C.

EXAMPLE 8

5-Chloro-1-[[(2,4-dimethoxyphenyl)sulphonyl)-3-(2-isopropoxyphenyl)-2-oxo-2,3-dihydro-1H-indol-3-yl 4-(4-pyridyl)-1-piperazinecarboxylate 1,5-fumarate.

(I): 1.5 C$_2$H$_2$O$_4$: R$_1$=Cl; R$_2$=H; R$_3$=OCH(CH$_3$)$_2$; R$_4$=H; X=—O—, n=1;

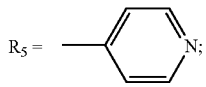

R$_6$=2-OCH$_3$; R$_7$=OCH$_3$

A mixture of 0.3 g of the compound obtained in Example 7 and 0.056 g of fumaric acid in 15 ml of acetonitrile is refluxed for 3 hours. The precipitate formed is filtered off with suction while hot, washed with ether and dried. 0.24 g of the expected product is obtained, m.p.=235° C.

EXAMPLE 9

5-Chloro-1-[(2,4-dimethoxyphenyl)sulphonyl]-3-(2-isopropoxyphenyl)-2-oxo-2,3-dihydro-1H-indol-3-yl 4-(4-pyridyl)-1-piperazinecarboxylate, laevorotatory isomer (I): R$_1$=Cl; R$_2$=H; R$_3$=OCH(CH$_3$)$_2$; R$_4$=H; X=—O—, n=1;

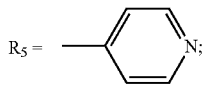

R$_6$=2-OCH$_3$; R$_7$=OCH$_3$.

A) Phenyl 5-chloro-3-(2-isopropoxyphenyl)-2-oxo-3-[[[4-(4-pyridyl)-1-piperazinyl]carbonyl]-oxy]-1-indolinecarboxylate A mixture of 6 g of the compound obtained in Preparation 1.10 and 1.8 g of 1-(4-pyridyl)piperazine in 60 ml of DCM is stirred at RT for 24 hours. The solvent is partially concentrated under vacuum and the resulting solution is chromatographed directly on silica gel, eluting with an EtOAc/MeOH mixture (95/5; v/v). 4.0 g of the expected product are obtained.

B) 5-Chloro-1-[[[(1S)-1-(hydroxymethyl)-3-methylbutyl]amino]carbonyl]-3-(2-isopropoxyphenyl)-2-oxo-2,3-dihydro-1H-indol-3-yl 4-(4-pyridyl)-1-piperazinecarboxylate, Less Polar Isomer and More Polar Isomer A mixture of 3.8 g of the compound obtained in the preceding step and 2.16 g of L-leucinol in 50 ml of chloroform is stirred for 48 hours. The mixture is concentrated under vacuum, the residue is taken up in DCM and the suspension thus obtained is chromatographed on alumina, eluting with a DCM/MeOH mixture (99/1; v/v). The product is rechromatographed on silica gel, eluting with a DCM/MeOH mixture (98.5/1.5; v/v). The diastereoisomers are separated:

less polar isomer: 0.53 g is obtained.

$$\alpha_D^{25} = -19.3° \; (c = 0.34; \text{chloroform})$$

the more polar isomer, which is crystallized from a DCM/iso ether mixture, to give 0.548 g, m.p.=199–202° C.

$$\alpha_D^{25} = -8.8° \; (c = 0.11; \text{chloroform})$$

C) 5-Chloro-3-(2-isopropoxyphenyl)-2-oxo-2,3-dihydro-1H-indol-3-yl 4-(4-pyridyl)-1-piperazinecarboxylate, laevorotatory isomer A mixture of 0.5 g of the compound obtained in the preceding step (the more polar isomer) and 0.042 g of sodium methoxide in 5 ml of MeOH and 5 ml of THF is stirred at RT for 18 hours. Water is added to the reaction mixture and the solvents are concentrated under vacuum, the resulting aqueous phase is extracted 4 times with DCM, the extracts are dried over Na$_2$SO$_4$ and the solvent is evaporated off under vacuum. The residue is chromatographed on silica gel, eluting with a DCM/MeOH mixture (92/8; v/v). 0.225 g of the expected product is obtained after crystallization from a DCM/iso ether mixture, m.p.=195–205° C.

$$\alpha_D^{25} = -18.8° \; (c = 0.266; \text{chloroform}).$$

D) 5-Chloro-1-[(2,4-dimethoxyphenyl)sulphonyl]-3-(2-isopropoxyphenyl)-2-oxo-2,3-dihydro-1H-indol-3-yl 4-(4-pyridyl)-1-piperazinecarboxylate, laevorotatory isomer 0.02 g of 60% sodium hydride in oil is added, under an argon atmosphere, to a mixture of 0.213 g of the compound obtained in the preceding step in 3 ml of DMF, and, after the evolution of gas has ceased, 0.119 g of 2,4-dimethoxybenzesulphonyl chloride is then added and the mixture is stirred at RT for 3 hours. The reaction mixture is poured into 5% K$_2$CO$_3$ solution and extracted with EtOAc, the organic phase is dried over Na$_2$SO$_4$ and the solvent is evaporated off under vacuum. The residue is chromatographed on silica gel, eluting with a DCM/MeOH mixture of from (95/5; v/v) to (93/7; v/v). 0.161 g of the expected product is obtained after crystallization from a DCM/hexane/iso ether mixture, m.p.=160–164° C.

$$\alpha_D^{20} = -71.8° \; (c = 0.18; \text{chloroform})$$

EXAMPLE 10

5-Chloro-1-[(2,4-dimethoxyphenyl)sulphonyl]-3-(2-isopropoxyphenyl)-2-oxo-2,3-dihydro-1H-indol-3-yl 4-(4-pyridyl)-1-piperazinecarboxylate, dextrorotatory isomer.

(I): $R_1$=Cl; $R_2$=H; $R_3$=OCH(CH$_3$)$_2$; $R_4$=H; X=—O—; n=1;

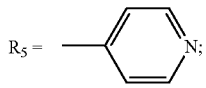

$R_6$=2-OCH$_3$; $R_7$=OCH$_3$.

A) 5-Chloro-3-(2-isopropoxyphenyl)-2-oxo-2,3-dihydro-1H-indol-3-yl 4-(4-pyridyl)-1-piperazinecarboxylate, dextrorotatory isomer This compound is prepared according to the procedure described in step C of Example 9, starting with 0.529 g of the compound obtained in step B of Example 9 (less polar isomer) and 0.043 g of sodium methoxide in 5 ml of MeOH and 5 ml of THF. 0.198 g of the expected product is obtained after crystallization from a DCM/iso ether mixture, m.p.=196–198° C.

$\alpha_D^{25} = +20.7°$ ($c = 0.32$; chloroform).

B) 5-Chloro-1-[(2,4-dimethoxyphenyl)sulphonyl]-3-(2-isopropoxyphenyl)-2-oxo-2,3-dihydro-1H-indol-3-yl 4-(4-pyridyl)-1-piperazinecarboxylate, dextrorotatory isomer This compound is prepared according to the procedure described in step D of Example 9, starting with 0.328 g of the compound obtained in the preceding step, 0.03 g of 60% sodium hydride in oil, 4 ml of DMF and 0.18 g of 2,4-dimethoxybenzenesulphonyl chloride, m.p.=161–167° C.

$\alpha_D^{20}$=+72.5° (c=0.14; chloroform).

EXAMPLE 11

5-Chloro-1-[(2,4-dimethoxyphenyl)sulphonyl]-3-(2,5-dimethoxyphenyl)-2-oxo-2,3-dihydro-1H-indol-3-yl 4-(2-pyridyl)-1-piperazinecarboxylate.

(I): $R_1$=Cl; $R_2$=H; $R_3$=OCH$_3$; $R_4$=5-OCH$_3$; X=—O—; n=1;

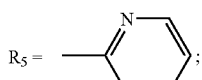

$R_6$=2-OCH$_3$; $R_7$=OCH$_3$.

A mixture of 0.4 g of the compound obtained in Preparation 1.17 and 0.4 g of 1-(2-pyridyl)-piperazine in 5 ml of DCM is stirred at 20° C. for 72 hours. The mixture is concentrated under vacuum, the residue is taken up in 30 ml of water and the precipitate formed is filtered off by suction. 0.4 g of the expected product is obtained after crystallization from MeOH, m.p.=254° C.

EXAMPLE 12

5-Chloro-1-[(2,4-dimethoxyphenyl)sulphonyl]-3-(2,5-dimethoxyphenyl)-2-oxo-2,3-dihydro-1H-indol-3-yl 4-(4-pyridyl)-1-piperazinecarboxylate.

(I): $R_1$=Cl; $R_2$=H; $R_3$=OCH$_3$; $R_4$=5-OCH$_3$; X=—O—; n=1;

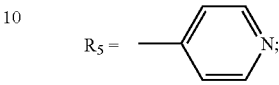

$R_6$=2-OCH$_3$; $R_7$=OCH$_3$.

A mixture of 0.4 g of the compound obtained in Preparation 1.17 and 0.4 g of 1-(4-pyridyl)-piperazine in 5 ml of DCM is stirred at 20° C. for 72 hours. The mixture is concentrated under vacuum, the residue is taken up in 20 ml of water and the precipitate formed is filtered off by suction. The precipitate is taken up in acetone and the solvent is concentrated under vacuum. The residue is chromatographed on silica gel, eluting with DCM, then with EtOAc and finally with acetone. 0.4 g of the expected product is obtained after crystallization from iso ether, m.p.=247–249° C.

EXAMPLE 13

N-[5-Chloro-1-[(2,4-dimethoxyphenyl)sulphonyl]-3-(2-methoxyphenyl)-2-oxo-2,3-dihydro-1H-indol-3-yl]-4-(4-pyridyl)piperazine-1-carboxamide, 0.25 H$_2$O.

(I): $R_1$=Cl; $R_2$=H; $R_3$=OCH$_3$; $R_4$=H; X=—NH—; n=1;

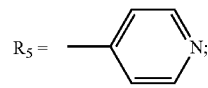

$R_6$=2-OCH$_3$; $R_7$=OCH$_3$.

A mixture of 0.5 g of the compound obtained in Preparation 1.18 and 0.268 g of 1-(4-pyridyl)-piperazine in 5 ml of chloroform is refluxed for 4 hours. The mixture is concentrated under vacuum and the residue is chromatographed on silica gel, eluting with DCM and then with a gradient of a DCM/EtOAc mixture down to (85/15; v/v). 0.281 g of the expected product is obtained after crystallization from a DCM/iso ether/hexane mixture.

EXAMPLE 14

N-[5-Chloro-1-[(2,4-dimethoxyphenyl)sulphonyl]-3-(2-methoxyphenyl)-2-oxo-2,3-dihydro-1H-indol-3-yl]-4-(4-pyridyl)piperazine-1-carboxamide, 0.75 H$_2$O, laevorotatory isomer (I): $R_1$=Cl; $R_2$=H; $R_3$=OCH$_3$; $R_4$=H; X=—NH—; n=1;

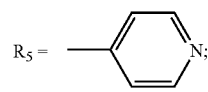

$R_6$=2-OCH$_3$; $R_7$=OCH$_3$.

A mixture of 1.136 g of the compound obtained in Preparation 1.19 and 0.608 g of 1-(4-pyridyl)piperazine in 10 ml of chloroform is stirred at RT for 48 hours and then refluxed for 1 hour. After cooling to RT, the reaction mixture is chromatographed directly on silica gel, eluting with a DCM/MeOH mixture of from (95/5; v/v) to (92/8; v/v). The product obtained is crystallized from a DCM/hexane/iso ether mixture and then the product obtained is dissolved in a minimum amount of MeOH and precipitated with addition of iso ether. 0.65 g of the expected product is obtained.

$$\alpha_D^{20} = -43° \ (c = 0.16; \text{chloroform}).$$

EXAMPLE 15

N-[5-Chloro-1-[(2,4-dimethoxyphenyl)sulphonyl]-3-(2-methoxyphenyl)-2-oxo-2,3-dihydro-1H-indol-3-yl]-4-(2-pyridyl)homopiperazine-1-carboxamide.

(I): $R_1$=Cl; $R_2$=H; $R_3$=OCH$_3$; $R_4$=H; X=—NH—; n=2;

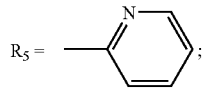

$R_6$=2-OCH$_3$; $R_7$=OCH$_3$.

A mixture of 0.4 g of the compound obtained in Preparation 1.18 and 1.3 g of the compound obtained in Preparation 2.3 in 20 ml of DCM is stirred at RT for 18 hours. The mixture is concentrated under vacuum, the residue is extracted with EtOAc, the organic phase is washed with saturated NaCl solution and dried over Na$_2$SO$_4$, and the solvent is evaporated off under vacuum. The residue is chromatographed on silica gel, eluting with a DCM/MeOH mixture (94/6; v/v). 0.22 g of the expected product is obtained after crystallization from a DCM/iso ether mixture, m.p.=152° C.

EXAMPLE 16

N-[5-Chloro-1-[(2,4-dimethoxyphenyl)sulphonyl]-3-(2-methoxyphenyl)-2-oxo-2,3-dihydro-1H-indol-3-yl]-4-(4-pyridyl)homopiperazine-1-carboxamide, 0.8 H$_2$O.

(I): $R_1$=Cl; $R_2$=H; $R_3$=OCH$_3$; $R_4$=H; X=—NH—; n=2;

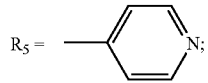

$R_6$=2-OCH$_3$; $R_7$=OCH$_3$.

A mixture of 0.5 g of the compound obtained in Preparation 1.18 and 0.375 g of the compound obtained in Preparation 2.4 in 20 ml of DCM is refluxed for 18 hours. The mixture is concentrated under vacuum, the residue is extracted with EtOAc, the organic phase is washed with 5% Na$_2$CO$_3$ solution, with water and with saturated NaCl solution and dried over Na$_2$SO$_4$, and the solvent is evaporated off under vacuum. The residue is chromatographed on silica gel, eluting with a DCM/MeOH mixture (94/6; v/v). 0.386 g of the expected product is obtained after crystallization from a DCM/iso ether mixture, m.p.=168° C.

EXAMPLE 17

N-[5-Chloro-1-[(2,4-dimethoxyphenyl)sulphonyl]-3-(2-isopropoxyphenyl)-2-oxo-2,3-dihydro-1H-indol-3-yl]-4-(3-pyridyl)piperazine-1-carboxamide, dextrorotatory isomer.

(I): $R_1$=Cl; $R_2$=H; $R_3$=OCH(CH$_3$)$_2$; $R_4$=H; X=—NH—; n=1;

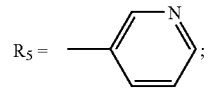

$R_6$=2-OCH$_3$; $R_7$=OCH$_3$.

A mixture of 0.639 g of the compound obtained in Preparation 1.20 and 0.325 g of the compound obtained in Preparation 2.2 in 10 ml of chloroform and 5 ml of THF is refluxed for 36 hours. The reaction mixture is chromatographed directly on silica gel, eluting with a DCM/MeOH mixture (96/4; v/v). 0.215 g of the expected product is obtained after crystallization from a DCM/iso ether mixture, m.p.=148° C.

$$\alpha_D^{20} = +25.6° \ (c = 0.15; \text{chloroform}).$$

$^1$H NMR: DMSO-d$_6$: δ (ppm): 1.0: d: 3H; 1.2: d: 3H; 3.0: mt: 4H; 3.4: mt: 4H; 3.5: s: 3H; 3.9: s: 3H; 4.7: mt: 1H; 6.6: mt: 2H; 6.9: t: 1H; 7.1: d: 1H; 7.2 to 7.4: m: 6H; 7.6: s: 1H; 7.8: dd: 1H; 7.9: d: 1H; 8.0: d: 1H; 8.3: bs: 1H.

EXAMPLE 18

N-[5-Chloro-1-[(2,4-dimethoxyphenyl)sulphonyl]-3-(2-isopropoxyphenyl)-2-oxo-2,3-dihydro-1H-indol-3-yl]-4-(3-pyridyl)piperazine-1-carboxamide, laevorotatory isomer.

(I): $R_1$=Cl; $R_2$=H; $R_3$=OCH(CH$_3$)$_2$; $R_4$=H; X=—NH—; n=1;

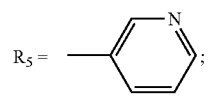

$R_6$=2-OCH$_3$; $R_7$=OCH$_3$.

This compound is prepared according to the procedure described in Example 17, starting with 0.5 g of the compound obtained in Preparation 1.21 and 0.26 g of the compound obtained in Preparation 2.2 in 10 ml of chloroform and 5 ml of THF.

$$\alpha_D^{20} = -33° \ (c = 0.15; \text{chloroform}).$$

EXAMPLE 19

N-[5-Chloro-1-[(2,4-dimethoxyphenyl)sulphonyl]-3-(2-isopropoxyphenyl)-2-oxo-2,3-dihydro-1H-indol-3-yl]-4-(4-pyridyl)piperazine-1-carboxamide, dextrorotatory isomer.

(I): $R_1$=Cl; $R_2$=H; $R_3$=OCH(CH$_3$)$_2$; $R_4$=H; X=—NH—; n=1

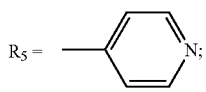

$R_6$=2-OCH$_3$; $R_7$=OCH$_3$.

A mixture of 0.5 g of the compound obtained in Preparation 1.21 and 0.26 g of 1-(4-pyridyl)-piperazine in 5 ml of chloroform is refluxed for 18 hours. The reaction mixture is chromatographed directly on silica gel, eluting with a DCM/MeOH mixture of from (95/5; v/v) to (92/8; v/v). The product obtained is crystallized by cold evaporation of a DCM/hexane/iso ether mixture. 0.46 g of the expected product is obtained.

$$\alpha_D^{20} = +7.9° \ (c = 0.175; \text{chloroform}).$$

EXAMPLE 20

N-[5-Chloro-1-[(2,4-dimethoxyphenyl)sulphonyl]-3-(2-isopropoxyphenyl)-2-oxo-2,3-dihydro-1H-indol-3-yl]-4-(4-pyridyl)piperazine-1-carboxamide, laevorotatory isomer.

(I): $R_1$=Cl; $R_2$=H; $R_3$=OCH(CH$_3$)$_2$; $R_4$=H; X=—NH—; n=1;

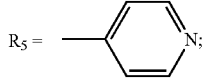

$R_6$=2-OCH$_3$; $R_7$=OCH$_3$.

A mixture of 0.9 g of the compound obtained in Preparation 1.20 and 0.463 g of 1-(4-pyridyl)-piperazine in 10 ml of chloroform is stirred at RT for 48 hours. The reaction mixture is chromatographed directly on silica gel, eluting with a DCM/MeOH mixture (95/5; v/v). The expected product is crystallized by cold evaporation of a DCM/hexane/iso ether mixture. 0.789 g of the expected product is obtained.

$$\alpha_D^{20} = -10.3° \ (c = 0.17; \text{chloroform}).$$

$^1$H NMR: DMSO-d$_6$: δ (ppm): 1.0: d: 6H; 3.2 to 3.7: m+s: 11H; 3.8: s: 3H; 4.6: mt: 1H; 6.6: s+mt: 2H; 6.8: t: 1H; 6.9: d: 1H; 7.2: d: 2H; 7.3: mt: 4H; 7.6: s: 1H; 7.7: d: 1H; 7.8: d: 1H; 8.2: d: 2H.

EXAMPLE 21

N-[5-Chloro-1-[(2,4-dimethoxyphenyl)sulphonyl]-3-(2,5-dimethoxyphenyl)-2-oxo-2,3-dihydro-1H-indol-3-yl]-4-(2-pyridyl)piperazine-1-carboxamide.

(I): $R_1$=Cl; $R_2$=H; $R_3$=OCH$_3$; $R_4$=5-OCH$_3$; X=—NH—; n=1;

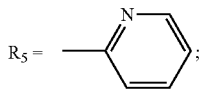

$R_6$=2-OCH$_3$; $R_7$=OCH$_3$.

This compound is prepared according to the procedure described in Example 13, starting with 0.46 g of the compound obtained in Preparation 1.22 and 0.21 ml of 1-(2-pyridyl)piperazine in 5 ml of chloroform. 0.382 g of the expected product is obtained after crystallization from a DCM/iso ether/hexane mixture.

$^1$H NMR: DMSO-d$_6$: δ (ppm): 3.4 to 3.8: m+3s: 17H; 4.0: s: 3H; 6.8: mt: 2H; 7.0: mt: 4H; 7.4: mt: 3H; 7.8: d: 1H; 7.9: d: 1H; 8.2: mt: 2H.

EXAMPLE 22

N-[5-Chloro-1-[(2,4-dimethoxyphenyl)sulphonyl]-3-(2-methoxyphenyl)-6-trifluoromethyl-2-oxo-2,3-dihydro-1H-indol-3-yl]-4-(4-pyridyl)piperazine-1-carboxamide, single enantiomer.

(I): $R_1$=Cl; $R_2$=6-CF$_3$; $R_3$=OCH$_3$; $R_4$=H; X=—NH—; n=1;

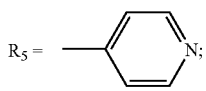

$R_6$=2-OCH$_3$; $R_7$=OCH$_3$.

This compound is prepared according to the procedure described in Example 15, starting with 0.203 g of the compound obtained in Preparation 1.25 and 0.098 g of 1-(4-pyridyl)piperazine in 3 ml of chloroform and 3 ml of THF. 0.098 g of the expected product is obtained after crystallization from a DCM/iso ether mixture, m.p.=174° C.

EXAMPLE 23

5-Chloro-1-[(2,4-dimethoxyphenyl)sulphonyl]-3-(2-isopropoxyphenyl)-3-[2-oxo-2-[4-(4-pyridyl)-1-piperazinyl]ethoxy]-1,3-dihydro-2H-indol-2-one.

(I): $R_1$=Cl; $R_2$=H; $R_3$=OCH(CH$_3$)$_2$; $R_4$=H; X=—O—CH$_2$—; n=1;

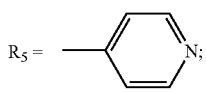

$R_6$=2-OCH$_3$; $R_7$=OCH$_3$.

A) 5-Chloro-3-(2-isopropoxyphenyl)-3-[2-oxo-2-[4-(4-pyridyl)-1-piperazinyl]ethoxy]-1,3-dihydro-2H-indol-2-one 1.2 g of BOP, 2 ml of DIPEA and then 0.48 g of 1-(4-pyridyl)piperazine are added, at 20° C., to a mixture of 1 g of the compound obtained in Preparation 1.27 in 20 ml of DCM, and the mixture is stirred at RT for 1 hour. 20 ml of 2N NaOH are then added, the mixture is extracted with EtOAc, the organic phase is washed with water and dried over $Na_2SO_4$, and the solvents are evaporated off under vacuum. The residue is chromatographed on silica gel, eluting with DCM, then with EtOAc and with acetone. 0.55 g of the expected product is obtained after crystallization from iso ether, m.p.=115–1200C.

B) 5-Chloro-1-[(2,4-dimethoxyphenyl)sulphonyl]-3-(2-isopropoxyphenyl)-3-[2-oxo-2-[4-(4-pyridyl)-1-piperazinyl]ethoxy]-1,3-dihydro-2H-indol-2-one This compound is prepared according to the procedure described in step B of Example 1, starting with 0.5 g of the compound obtained in the preceding step, 0.04 g of 60% sodium hydride in oil, 10 ml of THF and 0.3 g of 2,4-dimethoxybenzenesulphonyl chloride. 0.55 g of the expected product is obtained after crystallization from iso ether, m.p.=201–203° C.

EXAMPLE 24

5-Chloro-1-((2,4-dimethoxyphenyl)sulphonyl]-3-(2-methoxyphenyl)-3-[[2-oxo-2-[4-(2-pyridyl)-1-piperazinyl]ethyl]amino]-1,3-dihydro-2H-indol-2-one.

(I): $R_1$=Cl; $R_2$=H; $R_3$=$OCH_3$; $R_4$=H; X=—NH—$CH_2$—; n=1;

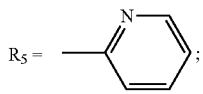

$R_6$=2-$OCH_3$; $R_7$=$OCH_3$ 0.329 g of PyBOP is added to a solution of 0.33 g of the compound obtained in Preparation 1.28, 0.11 g of 1-(2-pyridyl)piperazine and 0.121 g of triethylamine in 5 ml of DCM, and the mixture is stirred at RT for 3 hours. The resulting mixture is concentrated under vacuum, the residue is extracted with EtOAc, the organic phase is washed with water and dried over $Na_2SO_4$, and the solvent is evaporated off under vacuum. The residue is chromatographed on silica gel, eluting with a DCM/EtOAc mixture (90/10; v/v). 0.29 g of the expected product is obtained after crystallization from iso ether, m.p.=155° C.

EXAMPLE 25

5-Chloro-1-[(2,4-dimethoxyphenyl)sulphonyl]-3-(2-methoxyphenyl)-3-[[3-oxo-3-[4-(2-pyridyl)-1-piperazinyl]propyl]amino]-1,3-dihydro-2H-indol-2-one.

(I): $R_1$=Cl; $R_2$=H; $R_3$=$OCH_3$; $R_4$=H; X=—NH—$CH_2$—$CH_2$—; n=1,

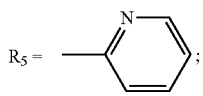

$R_6$=2-$OCH_3$; $R_7$=$OCH_3$ 0.37 g of PyBOP is added to a solution of 0.4 g of the compound obtained in Preparation 1.29, 0.127 g of 1-(2-pyridyl)piperazine and 0.143 g of triethylamine in 10 ml of DCM, and the mixture is stirred at RT for 2 hours. The reaction mixture is diluted with DCM, the organic phase is washed with water and dried over $Na_2SO_4$, and the solvent is evaporated off under vacuum. The residue is chromatographed on silica gel, eluting with a DCM/EtOAc mixture (90/10; v/v). 0.36 g of the expected product is obtained after crystallization from iso ether, m.p.=214° C.

$^1$H NMR: DMSO-$d_6$: δ (ppm): 2.0 to 2.5: 2 mt: 4H; 3.1 to 3.6: m+s: 11H; 3.7: s: 3H; 3.9: s: 3H; 6.6 to 7.0: m: 6H; 7.1: t: 1H; 7.3: t: 1H; 7.5: dd: 1H; 7.6: mt: 1H; 7.7 to 8.0: mt: 4H; 8.2: dd: 1H.

EXAMPLE 26

N-[5-Chloro-1-[(2,4-dimethoxyphenyl)sulphonyl]-3-(2-isopropoxyphenyl)-2-oxo-2,3-dihydro-1H-indol-3-yl]-4-(3-pyridazinyl)piperazine-1-carboxamide, single enantiomer (I): $R_1$=Cl; $R_2$=H; $R_3$=$OCH(CH_3)_2$; $R_4$=H; X=—NH—; n=1,

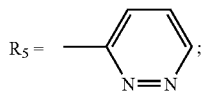

$R_6$=2-$OCH_3$; $R_7$=$OCH_3$

A solution of 0.07 g of the compound obtained in Preparation 1.20 is added to a solution of 0.054 g of 1-(3-pyridazinyl)piperazine in 2 ml of chloroform, and the mixture is then heated at 60° C. for 24 hours. The reaction mixture is chromatographed directly on silica gel, eluting with a DCM/MeOH mixture (95/5; v/v). The expected product is obtained. HPLC purity: 100%.

EXAMPLE 27

N-[5-Chloro-1-[(2,4-dimethoxyphenyl)sulphonyl]-3-(2-isopropoxyphenyl)-2-oxo-2,3-dihydro-1H-indol-3-yl]-4-(2-pyrimidinyl)piperazine-1-carboxamide, single enantiomer (I): $R_1$=Cl; $R_2$=H; $R_3$=$OCH(CH_3)_2$; $R_4$=H; X=—NH—; n=1,

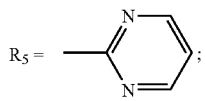

$R_6$=2-$OCH_3$; $R_7$=$OCH_3$

This compound is prepared according to the procedure described in Example 26, starting with 0.054 g of 1-(2-pyrimidinyl)piperazine in 2 ml of chloroform and 0.07 g of the compound obtained in Preparation 1.20. The expected product is obtained. HPLC purity: 99%.

Working according to the procedures described in the above examples, starting with the compounds of formula (II) in which W=H and the compounds of formula (V), the compounds of formula (IV) collated in Table I below are prepared:

TABLE I (IV)

[Structure of compound (IV): substituted indolin-2-one with R1, R2 on the indoline ring, R3 and R4 on phenyl, connected via X-C(=O)-N to a piperazine bearing R5, with (CH2)n in the ring]

| Compounds (IV) | R₁ | R₂ | R₃ | R₄ | X | n | R₅ | m.p. °C., crystallization solvent |
|---|---|---|---|---|---|---|---|---|
| IV. 1 (a) | Cl | H | OCH₃ | H | —CH₂— | 1 | pyrazin-2-yl | 87 — |
| IV. 2 (b) | Cl | 6-Cl | OCH₃ | H | —CH₂— | 1 | pyridin-4-yl | 286–288 iso ether |
| IV. 3 (c) | Cl | 6-Cl | OCH₃ | H | —CH₂— | 1 | pyridin-3-yl | 182–189 iso ether |
| IV. 4 (d) | Cl | 6-CH₃ | OCH₃ | H | —CH₂— | 1 | pyridin-4-yl | 102–110 — |
| IV. 5 (e) | Cl | 6-CH₃ | OCH₃ | H | —CH₂— | 1 | pyridin-3-yl | 248–250 EtOAc |
| IV. 6 (f) | Cl | 6-CH₃ | OCH(CH₃)₂ | H | —CH₂— | 1 | pyridin-4-yl | — — |
| IV. 7 (g) | Cl | H | F | H | —CH₂— | 1 | pyridin-4-yl | — — |
| IV. 8 (h) | Cl | 6-Cl | F | H | —CH₂— | 1 | pyridin-4-yl | 274–276 DCM |
| IV. 9 (i) | Cl | H | OCH₃ | 3-OCH₃ | —CH₂— | 1 | pyridin-4-yl | — DCM |
| IV. 10 (j) | Cl | H | OCH₂CH₃ | H | —CH₂— | 1 | pyridin-3-yl | — — |
| IV. 11 (k) | Cl | 6-CH₃ | OCH₂CH₃ | H | —CH₂— | 1 | pyridin-4-yl | — — |
| IV. 12 (l) | Cl | H | OCH(CH₃)₂ | H | —CH₂— | 1 | pyridin-4-yl | — — |

TABLE I-continued

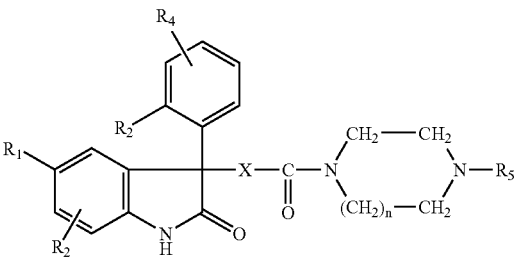

(IV)

| Compounds (IV) | R₁ | R₂ | R₃ | R₄ | X | n | R₅ | m.p. °C., crystallization solvent |
|---|---|---|---|---|---|---|---|---|
| IV. 13 (m) | Cl | H | OCH(CH₃)₂ | H | —CH₂— | 2 | 4-pyridyl | — |
| IV. 14 (n) | Cl | H | OCH(CH₃)₂ | H | —CH₂— | 1 | 2-pyrimidinyl | — |
| IV. 15 (o) | Cl | H | OCH(CH₃)₂ | H | —CH₂— | 1 | 3-pyridazinyl | 233 iso ether |
| IV. 16 (p) | Cl | H | OCH(CH₃)₂ | H | —CH₂— | 1 | 2-thiazolyl | 157 ether |
| IV. 17 (q) | Cl | 6-CH₃ | OCH(CH₃)₂ | H | —CH₂— | 1 | 4-pyridyl | — |
| IV. 18 (r) | Cl | H | F | H | —CH₂— | 1 | 4-pyridyl | — $\alpha_D^{20} = +47°$ (c = 0.15; chloroform) |
| IV. 19 (s) | Cl | H | OCH(CH₃)₂ | H | —CH₂— | 1 | 4-pyridyl | 192–196 iso ether |

(a) Compound prepared according to the procedure described in step A of Example 1, starting with the compound of Preparation 1.1 and the compound of Preparation 2.1.
(b) Compound prepared according to the procedure described in step A of Example 1, starting with the compound of Preparation 1.5 and 1-(4-pyridyl)piperazine.
(c) Compound prepared according to the procedure described in step A of Example 1, starting with the compound of Preparation 1.5 and the compound of Preparation 2.2.
(d) Compound prepared according to the procedure described in step A of Example 3, starting with the compound of Preparation 1.6 and 1-(4-pyridyl)piperazine.
(e) Compound prepared according to the procedure described in step A of Example 3, starting with the compound of Preparation 1.6 and the compound of Preparation 2.2.
(f) Compound prepared according to the procedure described in step A of Example 3, starting with the compound of Preparation 1.7 and 1-(4-pyridyl)piperazine.
(g) Compound prepared according to the procedure described in step A of Example 1, starting with the compound obtained in step B of Preparation 1.30 and 1-(4-pyridyl)piperazine.
(h) Compound prepared according to the procedure described in step A of Example 1, starting with the compound of Preparation 1.31 and 1-(4-pyridyl)piperazine.
(i) Compound prepared according to the procedure described in step A of Example 1, starting with the compound of Preparation 1.32 and 1-(4-pyridyl)piperazine.
(j) Compound prepared according to the procedure described in step A of Example 1, starting with the compounds of Preparations 1.2 and 2.2.
(k) Compound prepared according to the procedure described in step A of Example 1, starting with the compound of Preparation 1.33 and 1-(4-pyridyl)piperazine.
(l) Compound prepared according to the procedure described in step A of Example 1, starting with the compound of step E of Preparation 1.3 and the compound of Preparation 2.2.
(m) Compound prepared according to the procedure described in step A of Example 1, starting with the compound of step E of Preparation 1.3 and the compound of Preparation 2.4.

TABLE I-continued

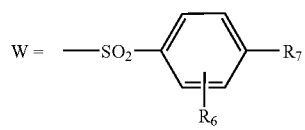

(IV)

| Compounds (IV) | $R_1$ | $R_2$ | $R_3$ | $R_4$ | X | n | $R_5$ | m.p. °C., crystallization solvent |
|---|---|---|---|---|---|---|---|---|

(n) Compound prepared according to the procedure described in step A of Example 1, starting with the compound of step E of Preparation 1.3 and 1-(2-pyrimidinyl)piperazine.
(o) Compound prepared according to the procedure described in step A of Example 1, starting with the compound of step E of Preparation 1.3 and 1-(3-pyridazinyl)piperazine.
(p) Compound prepared according to the procedure described in step A of Example 1, starting with the compound of step E of Preparation 1.3 and 1-(1,3-thiazol-2-yl)piperazine.
(q) Compound prepared according to the procedure described in step A of Example 1, starting with the compounds of Preparations 1.7 and 2.2.
(r) Compound prepared according to the procedure described in step A of Example 1, starting with the compound of Preparation 1.30 and 1-(4-pyridyl)piperazine.
(s) Compound prepared according to the procedure described in step A of Example 1, starting with the compound of step E of Preparation 1.3 and 1-(4-pyridyl)piperazine.

Working according to the procedures described in the above examples, starting with the compounds of formula (II) in which $$W = -SO_2-\underset{R_6}{\overset{R_7}{\text{—}}}$$

and the compounds of formula (III), or starting with the compounds of formula (IV) and 2,4-dimethoxybenzenesulphonyl chloride, the compounds according to the invention collated in Table II) below are prepared:

TABLE II

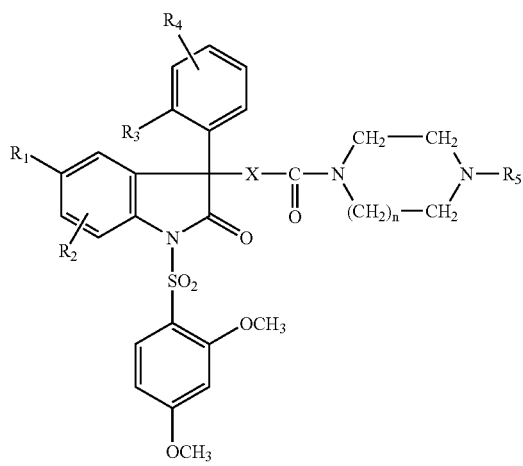

(I)

| Examples | $R_1$ | $R_2$ | $R_3$ | $R_4$ | X | n | $R_5$ | m.p. °C.; salt crystallization solvent $\alpha_D^{20}$ (chloroform) |
|---|---|---|---|---|---|---|---|---|
| 1 | Cl | H | OCH$_3$ | H | —CH$_2$— | 1 | 4-pyridyl | 136–141 (dec) iso ether — |

TABLE II-continued

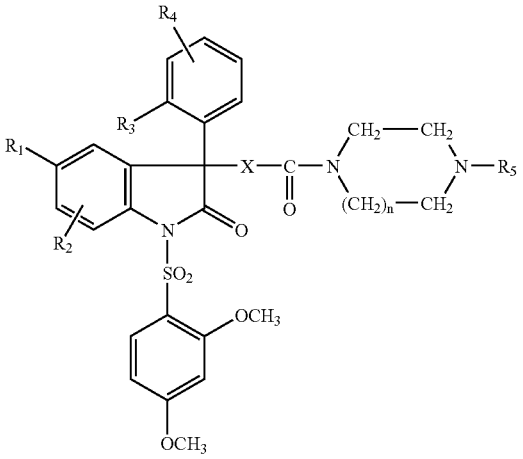

(I)

| Examples | R₁ | R₂ | R₃ | R₄ | X | n | R₅ | m.p. °C.; salt crystallization solvent $\alpha_D^{20}$ (chloroform) |
|---|---|---|---|---|---|---|---|---|
| 2 | Cl | H | OCH₂CH₃ | H | —CH₂— | 1 | 4-pyridyl | 225 iso ether — |
| 3 | Cl | H | OCH(CH₃)₂ | H | —CH₂— | 1 | 4-pyridyl | — — −21.3° (c = 0.1; DCM) |
| 4 | CH₃ | H | Cl | H | —CH₂— | 1 | 2-pyridyl | 239 iso ether — |
| 5 | Cl | H | OCH₃ | H | —O— | 1 | 2-pyridyl | 210–215 iso ether — |
| 6 | Cl | H | OCH₃ | H | —O— | 1 | 4-pyridyl | 197–198 iso ether — |
| 7 | Cl | H | OCH(CH₃)₂ | H | —O— | 1 | 4-pyridyl | 253 EtOAc — |
| 8 | Cl | H | OCH(CH₃)₂ | H | —O— | 1 | 4-pyridyl | 235; 1.5 fumarate; acetonitrile — |
| 9 | Cl | H | OCH(CH₃)₂ | H | —O— | 1 | 4-pyridyl | 160–164 DCM/hexane/iso ether −71.8° (c = 0.18) |
| 10 | Cl | H | OCH(CH₃)₂ | H | —O— | 1 | 4-pyridyl | 161–167 DCM/hexane/iso ether +72.5° (c = 0.14) |
| 11 | Cl | H | OCH₃ | 5-OCH₃ | —O— | 1 | 2-pyridyl | 254 MeOH |

TABLE II-continued

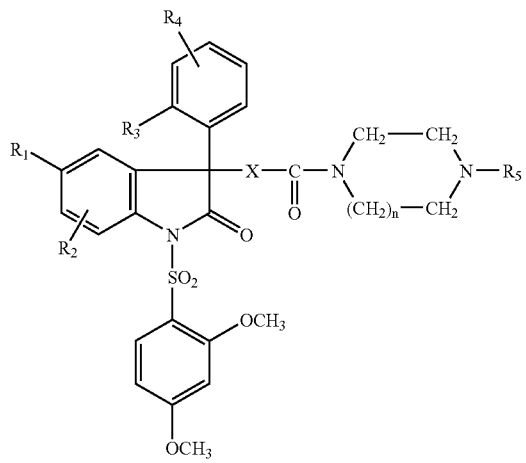

(I)

| Examples | R₁ | R₂ | R₃ | R₄ | X | n | R₅ | m.p. °C.; salt crystallization solvent $\alpha_D^{20}$ (chloroform) |
|---|---|---|---|---|---|---|---|---|
| 12 | Cl | H | OCH₃ | 5-OCH₃ | —O— | 1 | 4-pyridyl | 247–249 iso ether — |
| 13 | Cl | H | OCH₃ | H | —NH— | 1 | 4-pyridyl | — DCM/hexane/iso ether — |
| 14 | Cl | H | OCH₃ | H | —NH— | 1 | 4-pyridyl | — MeOH/iso ether −43° (c = 0.16) |
| 15 | Cl | H | OCH₃ | H | —NH— | 2 | 2-pyridyl | 152 DCM/iso ether — |
| 16 | Cl | H | OCH₃ | H | —NH— | 2 | 4-pyridyl | 168 DCM/iso ether — |
| 17 | Cl | H | OCH(CH₃)₂ | H | —NH— | 1 | 3-pyridyl | 148 DCM/iso ether +25.6° (c = 0.15) |
| 18 | Cl | H | OCH(CH₃)₂ | H | —NH— | 1 | 3-pyridyl | — DCM/iso ether −33° (c = 0.15) |
| 19 | Cl | H | OCH(CH₃)₂ | H | —NH— | 1 | 4-pyridyl | — DCM/hexane/iso ether +7.9° (c = 0.175) |
| 20 | Cl | H | OCH(CH₃)₂ | H | —NH— | 1 | 4-pyridyl | — DCM/hexane/iso ether −10.3° (c = 0.17) |
| 21 | Cl | H | OCH₃ | 5-OCH₃ | —NH— | 1 | 2-pyridyl | — DCM/hexane/iso ether — |

TABLE II-continued

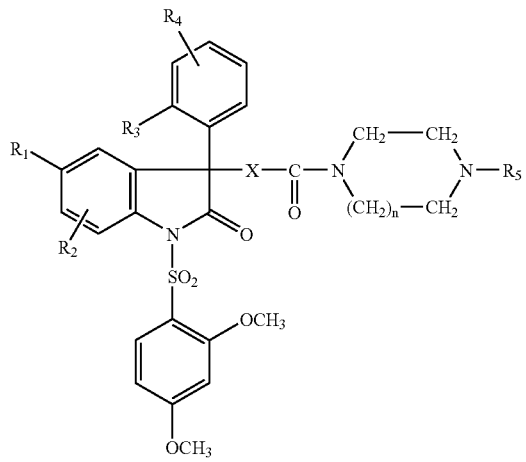

(I)

| Examples | R$_1$ | R$_2$ | R$_3$ | R$_4$ | X | n | R$_5$ | m.p. ° C.; salt crystallization solvent $\alpha_D^{20}$ (chloroform) |
|---|---|---|---|---|---|---|---|---|
| 22 | Cl | 6-CF$_3$ | OCH$_3$ | H | —NH— | 1 | 4-pyridyl | 174 DCM/iso ether — |
| 23 | Cl | H | OCH(CH$_3$)$_2$ | H | —O—CH$_2$— | 1 | 4-pyridyl | 201–203 iso ether — |
| 24 | Cl | H | OCH$_3$ | H | —NH—CH$_2$— | 1 | 2-pyridyl | 155 iso ether — |
| 25 | Cl | H | OCH$_3$ | H | —NH—CH$_2$—CH$_2$— | 1 | 2-pyridyl | 214 iso ether — |
| 26 | Cl | H | OCH(CH$_3$)$_2$ | H | —NH— | 1 | pyridazin-3-yl | — — — |
| 27 | Cl | H | OCH(CH$_3$)$_2$ | H | —NH— | 1 | pyrimidin-2-yl | — — — |
| 28 (a) | Cl | H | OCH$_3$ | H | —CH$_2$— | 1 | pyrazin-2-yl | 209–212 iso ether — |
| 29 (b) | Cl | 6-Cl | OCH$_3$ | H | —CH$_2$— | 1 | 4-pyridyl | 247–248 iso ether — |
| 30 (c) | Cl | 6-Cl | OCH$_3$ | H | —CH$_2$— | 1 | 3-pyridyl | 219–222 iso ether — |
| 31 (d) | Cl | 6-CH$_3$ | OCH$_3$ | H | —CH$_2$— | 1 | 4-pyridyl | 232–234 iso ether — |

TABLE II-continued

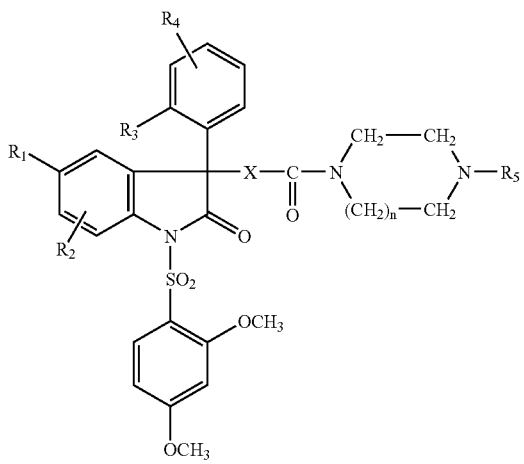

(I)

| Examples | R₁ | R₂ | R₃ | R₄ | X | n | R₅ | m.p. ° C.; salt crystallization solvent α_D²⁰ (chloroform) |
|---|---|---|---|---|---|---|---|---|
| 32 (e) | Cl | 6-CH₃ | OCH₃ | H | —CH₂— | 1 | 3-pyridyl | 215–217 iso ether — |
| 33 (f) | Cl | 6-CH₃ | OCH(CH₃)₂ | H | —CH₂— | 1 | 4-pyridyl | 261–262 iso ether — |
| 34 (g) | Cl | H | Cl | H | —O— | 1 | 2-pyridyl | 225–227 iso ether — |
| 35 (h) | Cl | H | Cl | H | —O— | 1 | 4-pyridyl | 135–140 iso ether — |
| 36 (i) | Cl | H | F | H | —O— | 1 | 4-pyridyl | 155 iso ether — |
| 37 (j) | Cl | H | CF₃ | H | —O— | 1 | 4-pyridyl | 192–194 iso ether — |
| 38 (k) | Cl | H | OCF₃ | H | —O— | 1 | 4-pyridyl | 236 iso ether — |
| 39 (l) | Cl | 6-CH₃ | OCH₃ | H | —O— | 1 | 4-pyridyl | 230 (dec) iso ether — |
| 40 (m) | Cl | 6-OCH₃ | Cl | H | —O— | 1 | 3-pyridyl | 160–170 iso ether — |
| 41 (n) | Cl | H | OCH₃ | H | —NH— | 1 | 2-pyridyl | 245 DCM/iso ether — |

TABLE II-continued (I)

| Examples | $R_1$ | $R_2$ | $R_3$ | $R_4$ | X | n | $R_5$ | m.p. °C.; salt crystallization solvent $\alpha_D^{20}$ (chloroform) |
|---|---|---|---|---|---|---|---|---|
| 42 (o) | Cl | H | Cl | H | —NH— | 1 | 2-pyridyl | — DCM/iso ether — |
| 43 (p) | Cl | H | Cl | H | —NH— | 1 | 4-pyridyl | 234 DCM/iso ether — |
| 44 (q) | Cl | H | Cl | H | —NH— | 1 | 2-pyrimidyl | 278 DCM/iso ether — |
| 45 (r) | Cl | 6-CH$_3$ | OCH$_3$ | H | —NH— | 1 | 4-pyridyl | 186 DCM/iso ether — |
| 46 (s) | CH$_3$ | 6-Cl | Cl | H | —NH— | 1 | 4-pyridyl | 225; NMR DCM/iso ether — |
| 47 (t) | Cl | H | OCH$_3$ | H | —NH—CH$_2$—CH$_2$— | 1 | 4-pyridyl | >250 ether — |
| 48 (u) | Cl | H | F | H | —CH$_2$— | 1 | 4-pyridyl | 129–135 iso ether — |
| 49 (v) | Cl | 6-Cl | F | H | —CH$_2$— | 1 | 4-pyridyl | 142–148 (dec) iso ether — |
| 50 (w) | Cl | H | OCH$_3$ | 3-OCH$_3$ | —CH$_2$— | 1 | 4-pyridyl | 175 — — |
| 51 (x) | Cl | H | OCH$_2$CH$_3$ | H | —CH$_2$— | 1 | 3-pyridyl | 226 iso ether — |

TABLE II-continued

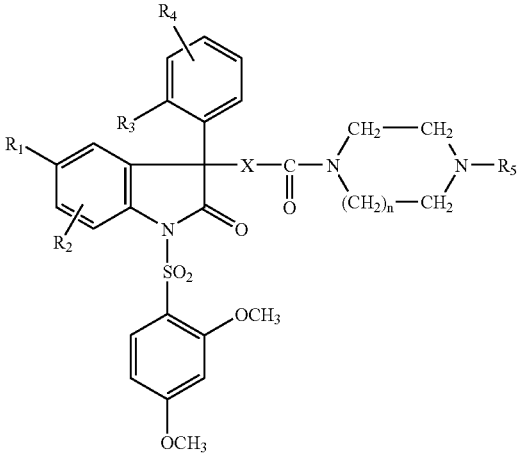

(I)

| Examples | R$_1$ | R$_2$ | R$_3$ | R$_4$ | X | n | R$_5$ | m.p. °C.; salt crystallization solvent α$_D^{20}$ (chloroform) |
|---|---|---|---|---|---|---|---|---|
| 52 (y) | Cl | 6-CH$_3$ | OCH$_2$CH$_3$ | H | —CH$_2$— | 1 | 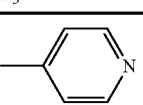 | 243 iso ether/EtOAc — |
| 53 (z) | Cl | H | OCH(CH$_3$)$_2$ | H | —CH$_2$— | 1 | 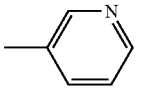 | 217 iso ether — |
| 54 (aa) | Cl | H | OCH(CH$_3$)$_2$ | H | —CH$_2$— | 2 | 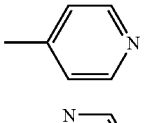 | 157 iso ether — |
| 55 (ab) | Cl | H | OCH(CH$_3$)$_2$ | H | —CH$_2$— | 1 | 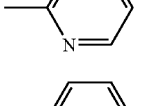 | 157–159 iso ether — |
| 56 (ac) | Cl | H | OCH(CH$_3$)$_2$ | H | —CH$_2$— | 1 | 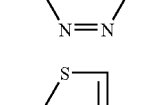 | 230 iso ether/EtOAc — |
| 57 (ad) | Cl | H | OCH(CH$_3$)$_2$ | H | —CH$_2$— | 1 | 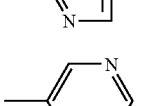 | 235 iso ether — |
| 58 (ae) | Cl | 6-CH$_3$ | OCH(CH$_3$)$_2$ | H | —CH$_2$— | 1 | 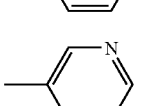 | 222 iso ether/EtOAc — |
| 59 (af) | Cl | H | OCH$_2$CH$_3$ | H | —O— | 1 | 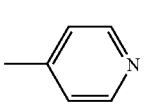 | 255–260 iso ether — |
| 60 (ag) | Cl | H | OCH$_2$CH$_3$ | H | —O— | 1 | 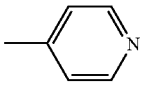 | 255–260 EtOAc — |
| 61 (ah) | Cl | H | F | H | —CH$_2$— | 1 |  | — — −79° (c = 0.13) |

TABLE II-continued

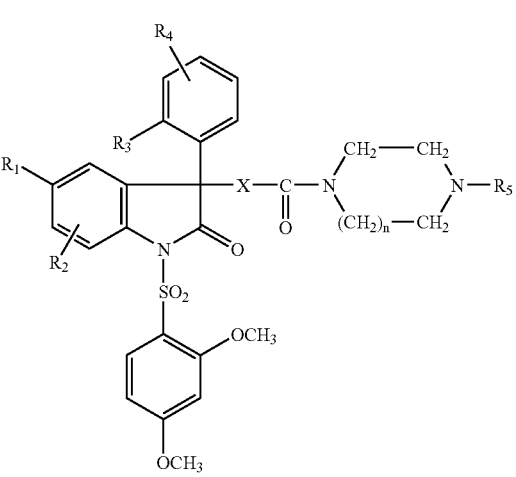

(I)

R$_6$ = 2-OCH$_3$; R$_7$ = OCH$_3$

| Examples | R$_1$ | R$_2$ | R$_3$ | R$_4$ | X | n | R$_5$ | m.p. ° C.; salt crystallization solvent α$_D^{20}$ (chloroform) |
|---|---|---|---|---|---|---|---|---|
| 62 (ai) | Cl | H | OCH(CH$_3$)$_2$ | H | —CH$_2$— | 1 | 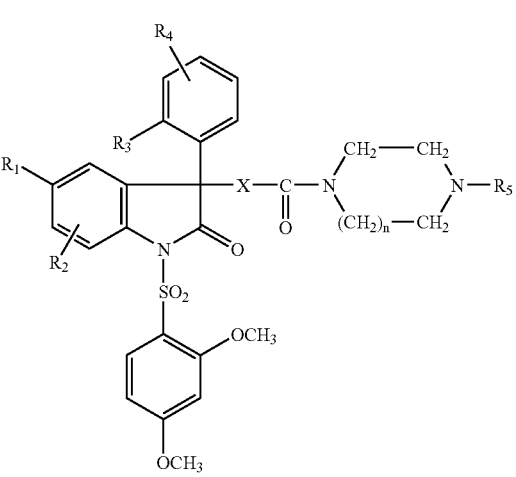 | 223 (dec) iso ether — |
| 63 (aj) | Cl | H | OCH(CH$_3$)$_2$ | H | —CH$_2$— | 1 | 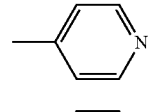 | 184; HCl propan-2-ol −13.5° (c = 0.14; MeOH) |
| 64 (ak) | Cl | H | OCH(CH$_3$)$_2$ | H | —CH$_2$— | 1 | 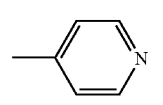 | 202; fumarate acetonitrile −11.7° (c = 0.12; MeOH) |
| 65 (al) | Cl | H | OCH(CH$_3$)$_2$ | H | —CH$_2$— | 1 | 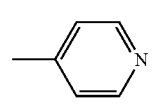 | 248; H$_3$PO$_4$ EtOH −7.7° (c = 0.13; MeOH) |

(a) Compound prepared according to the procedure described in step B of Example 1, starting with compound IV. 1.
(b) Compound prepared according to the procedure described in step B of Example 1, starting with compound IV. 2.
(c) Compound prepared according to the procedure described in step B of Example 1, starting with compound IV. 3.
(d) Compound prepared according to the procedure described in step B of Example 1, starting with compound IV. 4.
(e) Compound prepared according to the procedure described in step B of Example 1, starting with compound IV. 5.
(f) Compound prepared according to the procedure described in step B of Example 1, starting with compound IV. 6.
(g) Compound prepared according to the procedure described in Example 5, starting with the compound of Preparation 1.11 and 1-(2-pyridyl)piperazine.
(h) Compound prepared according to the procedure described in Example 5, starting with the compound of Preparation 1.11 and 1-(4-pyridyl)piperazine.
(i) Compound prepared according to the procedure described in Example 6, starting with the compound of Preparation 1.12 and 1-(4-pyridyl)piperazine.
(j) Compound prepared according to the procedure described in Example 6, starting with the compound of Preparation 1.13 and 1-(4-pyridyl)piperazine.
(k) Compound prepared according to the procedure described in Example 7, starting with the compound of Preparation 1.14 and 1-(4-pyridyl)piperazine.
(l) Compound prepared according to the procedure described in Example 5, starting with the compound of Preparation 1.15 and 1-(4-pyridyl)piperazine.
(m) Compound prepared according to the procedure described in Example 5, starting with the compound of Preparation 1.16 and 1-(4-pyridyl)piperazine.
(n) Compound prepared according to the procedure described in Example 13, starting with the compound of Preparation 1.18 and 1-(2-pyridyl)piperazine.
(o) Compound prepared according to the procedure described in Example 13, starting with the compound of Preparation 1.23 and 1-(2-pyridyl)piperazine.
(p) Compound prepared according to the procedure described in Example 13, starting with the compound of Preparation 1.23 and 1-(4-pyridyl)piperazine.

TABLE II-continued

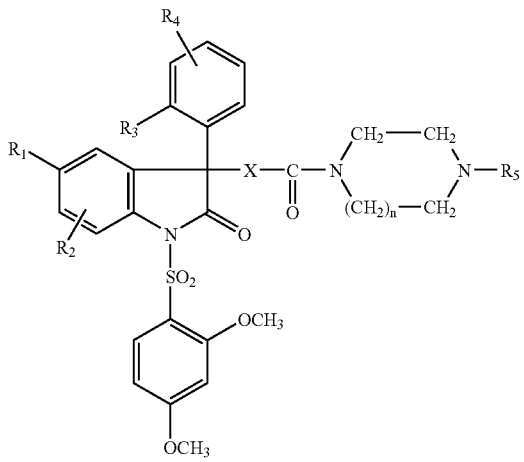

(I)

| Examples | $R_1$ | $R_2$ | $R_3$ | $R_4$ | X | n | $R_5$ | m.p. °C.; salt crystallization solvent $\alpha_D^{20}$ (chloroform) |
|---|---|---|---|---|---|---|---|---|

(q) Compound prepared according to the procedure described in Example 13, starting with the compound of Preparation 1.23 and 1-(2-pyrimidinyl)piperazine.
(r) Compound prepared according to the procedure described in Example 15, starting with the compound of Preparation 1.24 and 1-(4-pyridyl)piperazine.
(s) Compound prepared according to the procedure described in Example 13, starting with the compound of Preparation 1.26 and 1-(4-pyridyl)piperazine.
(t) Compound prepared according to the procedure described in Example 25, starting with the compound of Preparation 1.29 and 1-(4-pyridyl)piperazine.
(u) Compound prepared according to the procedure described in step B of Example 1, starting with compound IV. 7.
(v) Compound prepared according to the procedure described in step B of Example 1, starting with compound IV. 8.
(w) Compound prepared according to the procedure described in step B of Example 1, starting with compound IV. 9.
(x) Compound prepared according to the procedure described in step B of Example 1, starting with compound IV. 10.
(y) Compound prepared according to the procedure described in step B of Example 1, starting with compound IV. 11.
(z) Compound prepared according to the procedure described in step B of Example 1, starting with compound IV. 12.
(aa) Compound prepared according to the procedure described in step B of Example 1, starting with compound IV. 13.
(ab) Compound prepared according to the procedure described in step B of Example 1, starting with compound IV. 14.
(ac) Compound prepared according to the procedure described in step B of Example 1, starting with compound IV. 15.
(ad) Compound prepared according to the procedure described in step B of Example 1, starting with compound IV. 16.
(ae) Compound prepared according to the procedure described in step B of Example 1, starting with compound IV. 17.
(af) A mixture of 0.3 g of the compound obtained in Preparation 1.34, 0.3 g of the compound of Preparation 2.2 and 2 g of DIPEA in 15 ml of DMF is stirred at RT for 4 days. The mixture is concentrated under vacuum, the residue is taken up in water and extracted with EtOAc, the organic phase is washed with water and dried over $Na_2SO_4$, and the solvent is evaporated off under vacuum. The residue is chromatographed on silica gel, eluting with DCM and then with acetone. 0.27 g of the expected product is obtained after trituration in iso ether.
(ag) A mixture of 0.4 g of the compound obtained in Preparation 1.34 and 0.6 g of 1-(4-pyridyl)piperazine in 0.6 ml of THF is stirred at RT for 5 days. The mixture is concentrated under vacuum, the residue is taken up in 20 ml of water and 20 ml of EtOAc and stirred, and the precipitate formed is filtered off by suction and washed with iso ether. 0.4 g of the expected product is obtained.
(ah) Compound prepared according to the procedure described in step B of Example 1, starting with compound IV. 18.
(ai) Compound prepared according to the procedure described in step B of Example 1, starting with compound IV. 19.
(aj) A 2N solution of NCl in ether is added to a solution of 0.2 g of the compound of Example 3 in 20 ml of EtOH, and the resulting mixture is concentrated under vacuum. The residue is taken up in 2-propanol and the precipitate formed is filtered off by suction, washed with ether and dried. 0.12 g of the hydrochloride is obtained.
(ak) A mixture of 0.3 g of the compound of Example 3 and 0.059 g of fumaric acid in 20 ml of acetonitrile is refluxed for 10 minutes. After cooling, the precipitate formed is filtered off by suction to give 0.24 g of the fumarate.
(al) A mixture of 0.3 g of the compound of Example 3 and 0.051 g of 85% $H_3PO_4$ in 20 ml of EtOH is heated at 60° C. for 10 minutes. After cooling, the precipitate formed is filtered off by suction to give 0.3 g of the expected product.

EXAMPLE 46

$^1$H NMR: DMSO-d$_6$: δ (ppm): 2.3: s: 3H; 3.2 to 3.8: m+s: 1H; 3.9: s: 3H; 6.7: mt: 2H; 6.9: d: 2H; 7.2 to 7.4: m: 5H; 7.8: s: 1H; 7.9: d: 1H; 8.0: s: 1H; 8.2: d: 2H.

The compounds according to the invention underwent biochemical studies.

The affinity of the compounds of formula (I) according to the invention for arginine-vasopressin V$_{1b}$ receptors was determined in vitro using the method described by Y. De Keyser et al., FEBS Letters, 1994, 356, 215–220. This method consists in studying in vitro the displacement of tritiated arginine-vasopressin (($^3$H]-AVP) at the V$_{1b}$ receptors present on adenohypophysal membrane or cell preparations carrying rat or human V$_{1b}$ receptors. The 50% inhibitory concentrations (IC$_{50}$) for the attachment of tritiated arginine-vasopressin of the compounds according to the invention are low and vary from $10^{-6}$ to $10^{-9}$ M.

The affinity of the compounds of formula (I) according to the invention for arginine-vasopressin V$_{1a}$ receptors was determined in vitro using the method described by M. Thibonnier et al., J. Biol. Chem., 1994, 269, 3304–3310. This method consists in studying in vitro the displacement of tritiated arginine-vasopressin ([$^3$H]-AVP) at the V$_{1a}$ receptors present on membrane or cell preparations carrying rat or human V$_{1a}$ receptors. The compounds of formula (I) exhibit an affinity for arginine-vasopressin V$_{1a}$ receptors, with IC$_{50}$ values which vary from $10^{-6}$ to $10^{-9}$ M.

The affinity of the compounds of formula (I) according to the invention for vasopressin V$_2$ receptors has also been studied (method described by M. Birnbaumer et al., Nature (Lond.), 1992, 357, 333–335). The compounds studied have little or no affinity for the V$_2$ receptors, with IC$_{50}$ values which are generally greater than $10^{-6}$ M.

The affinity of the compounds according to the invention for the ocytocin receptors was determined in a test of in vitro binding using the method described by J. Elands et al. in Eur. J. Pharmacol., 1987, 147, 197–207. This method consists in studying in vitro the displacement of a radioiodine analogue of ocytocin to the ocytocin receptors in a cell membrane preparation transfected with the human uterine ocytocin receptor. The IC$_{50}$ values (concentration that inhibits 50% of the binding of the radioiodine analogue of ocytocin to its receptors) are low and vary from $10^{-6}$ to $10^{-9}$ M in this test.

The compounds of the present invention are in particular active principles of pharmaceutical compositions, the toxicity of which is compatible with their use as medicinal products.

According to another of its aspects, the present invention relates to the use of the compounds of formula (I), or one of their salts, solvates and/or hydrates which are pharmaceutically acceptable for the preparation of medicinal products intended for the treatment of any pathology where arginine-vasopressin and/or its V$_{1b}$ receptors and/or its V$_{1a}$ receptors and/or ocytocin and/or its receptors are involved.

Thus, the compounds according to the invention may be used, in man or in animals, in the treatment or prevention of various vasopressin-dependent conditions, such as cardiovascular conditions, for example hypertension, pulmonary hypertension, cardiac insufficiency, myocardial infarction or coronary vasospasm, in particular in smokers, Raynaud's disease, unstable angina and PTCA (percutaneous transluminal coronary angioplasty), cardiac ischaemia or haemostasis disturbances; conditions of the central nervous system, such as migraine, cerebral vasospasm, cerebral haemorrhage, cerebral oedema, depression, anxiety, stress, emotional disorders, obsessive-compulsive disorder, panic attacks, psychotic states or memory disorders, for example; conditions of the renal system, such as renal vasospasm, necrosis of the renal cortex; nephrogenic diabetes insipidus; conditions of the gastric system, such as gastric vasospasm, cirrhosis of the liver, ulcers or the pathology of vomiting, for example nausea, including nausea due to chemotherapy or travel sickness; or diabetic nephropathy. The compounds according to the invention can also be used in the treatment of disorders of sexual behaviour; in women, the compounds according to the invention can be used to treat dysmenorrhoea or premature labour. The compounds according to the invention can also be used in the treatment of small-cell lung cancers; hyponatremic encephalopathy; pulmonary syndrome; Ménière's disease; glaucoma; cataracts; obesity; type I and II diabetes; atherosclerosis; Cushing's syndrome; insulin resistance; or hypertriglyceridaemia; or in post-operative treatments, in particular after abdominal surgery.

The compounds according to the invention can also be used in the treatment or prevention of any pathology resulting from stress, such as fatigue and its syndromes, ACTH-dependent disorders, cardiac disorders, pain, modifications in gastric emptying, in faecal excretion (colitis, irritable bowel syndrome or Crohn's disease) or in acid secretion, hyperglycaemia, immunosuppression, inflammatory processes (rheumatoid arthritis and osteoarthritis), multiple infections, cancers, asthma, psoriasis, allergies and various neuropsychiatric disorders, such as anorexia nervosa, bulimia, mood disorders, depression, anxiety, sleep disorders, panic states, phobias, obsession, disorders of pain perception (fibromyalgia), neurodegenerative diseases (Alzheimer's disease, Parkinson's disease or Huntington's disease), drug dependence, weaning from drugs, haemorrhagic stress, muscle spasms or hypoglycaemia. The compounds according to the invention can also be used in the treatment or prevention of chronic stress conditions, such as immunodepression, fertility disorders or dysfunctionings of the hypothalamopituitary-adrenal axis.

The compounds according to the invention can also be used as psychostimulants, resulting in an increase in alertness or emotional reactivity to the surroundings and making adaptation easier.

The compounds according to the invention with affinity for the ocytocin receptors are particularly advantageous in the prevention and/or treatment of ocytocin-dependent disorders. The compounds according to the present invention are advantageous in cicatrization, in analgesia, in anxiolysis, in the prevention of pain, in the prevention of anxiety, depression, schizophrenia, autism, obsessive-compulsive syndromes, in maternal behaviour (facilitating the recognition and acceptance of the mother by the infant) and social behaviour, and memory; regulating the intake of food and drink, drug dependency, weaning from drugs, and sexual motivation; they may also be used advantageously in urogenital disorders, especially in obstetrics and gynaecology, especially as uterine relaxant or tocolytic agents or for controlling uterine contractions before the pregnancy is at full term, for controlling prenatal labour, or for controlling preparatory labour for the purpose of a birth by caesarean section, for solving the problems of sterility or fertility, birth control (veterinary use in particular), for controlling oestrus, stopping lactation, weaning, and the transfer and implantation of an embryo during in vitro fertilization; for treating endometriosis, dysmenorrhoea and also urinary stress incontinence or urgency incontinence, benign hypertrophy of the prostate and erectile dysfunctions, hypertension, hyponatraemia, cardiac insufficiency, atherosclerosis, angiogenesis, tumour proliferation, Kaposi's sarcoma and for regulating the storage of fats by the adipocyte.

Moreover, given the role of ocytocin in controlling luteinizing hormone (J. J. Evans, J. Endocrin. 1996, 151, 169–174), the compounds of the invention may be used to induce contraception.

Furthermore, the compounds according to the invention may be used for their antitumoral effects, in secreting ocytocin tumours, in particular breast cancers and prostate cancers.

The use of the compounds according to the invention for the prevention and/or treatment of the diseases mentioned above, and also for the preparation of medicinal products for treating these diseases, forms an integral part of the invention.

The above compounds of formula (I), or a pharmaceutically acceptable salt, solvate and/or hydrate thereof can be used at daily doses of 0.01 to 100 mg per kilo of body weight of the mammal to be treated, preferably at daily doses of 0.1 to 50 mg/kg. In man, the dose can preferably vary from 0.1 to 4 000 mg per day, more particularly from 0.5 to 1 000 mg, depending upon the age of the subject to be treated or the type of treatment: prophylactic or curative.

For their use as medicinal products, the compounds of formula (I) are generally administered in dosage units. The said dosage units are preferably formulated in pharmaceutical compositions in which the active principle is mixed with one or more pharmaceutical excipients.

Thus, according to another of its aspects, the present invention relates to pharmaceutical compositions including, as active principle, a compound of formula (I), or a pharmaceutically acceptable salt, solvate and/or hydrate thereof, and also one or more pharmaceutically acceptable excipients.

In the pharmaceutical compositions of the present invention for administration by the oral, sublingual, inhaled, subcutaneous, intramuscular, intravenous, transdermal, local or rectal route, the active principles can be administered in single-dose administration forms, as a mixture with conventional pharmaceutical vehicles, to animals and human beings. The appropriate single-dose administration forms comprise forms by the oral route, such as tablets, gelatin capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

The active principle of formula (I) is present in each dosage unit in the amounts suited to the daily doses envisaged. In general, each dosage unit is suitably adjusted according to the dosage and the type of administration provided, for example tablets, gelatin capsules and the like, sachets, blisters, syrups and the like, or drops, so that such a dosage unit comprises from 0.1 to 1 000 mg of active principle, preferably from 0.5 to 250 mg, which has to be administered one to four times daily.

Although these dosages are examples of average situations, there may be specific cases where higher or lower dosages are appropriate; such dosages also form part of the invention. According to the usual practice, the dosage appropriate to each patient is determined by the physician according to the method of administration and the age, the weight and the response of the said patient.

According to another of its aspects, the present invention also relates to a method for treating the pathologies indicated above, which comprises the administration, to a patient, of an effective dose of a compound according to the invention or a pharmaceutically acceptable salt thereof.

What is claimed is:
1. A compound of formula (I):

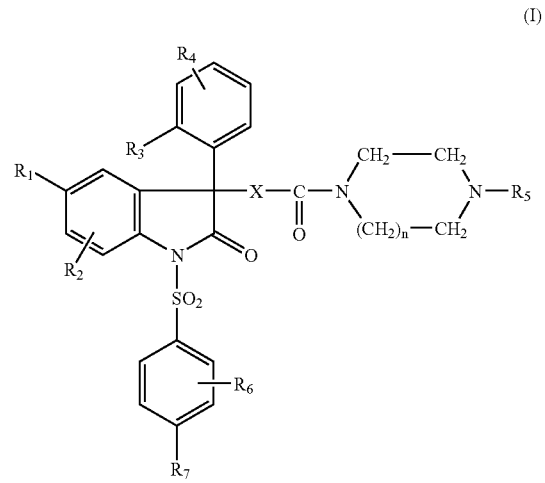

in which:
n is 1 or 2;
X represents —CH$_2$—; —O—; —NH—; —O—CH$_2$—; —NH—CH$_2$—; or —NH—CH$_2$—CH$_2$—;
R$_1$ represents halogen; a (C$_1$–C$_4$)alkyl; or (C$_1$–C$_4$)alkoxy;
R$_2$ represents hydrogen; halogen; (C$_1$–C$_4$)alkyl; (C$_1$–C$_4$) alkoxy; trifluoromethyl;
R$_3$ represents halogen; (C$_1$–C$_3$)alkyl; (C$_1$–C$_3$)alkoxy; trifluoromethyl; or trifluoromethoxy;
R$_4$ represents hydrogen; halogen; (C$_1$–C$_3$)alkyl; or (C$_1$–C$_3$)alkoxy;
R$_5$ is chosen from:

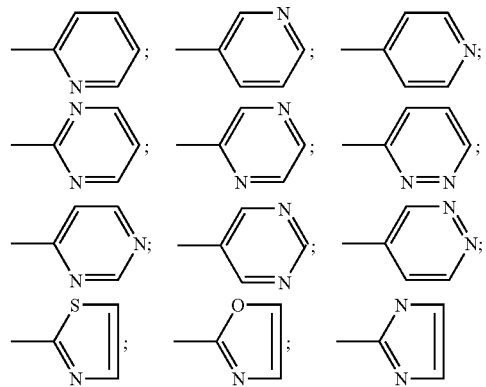

R$_6$ represents (C$_1$–C$_4$)alkoxy; and
R$_7$ represents (C$_1$–C$_4$)alkoxy;
or a salt or hydrate thereof.
2. A compound according to claim 1, in which:
R$_1$ represents chlorine or methyl;
R$_2$ represents hydrogen or is in position –6 of the indol-2-one and represents chlorine, methyl, methoxy or trifluoromethyl;
R$_3$ represents chlorine, fluorine, methoxy, ethoxy, isopropoxy, trifluoromethyl or trifluoromethoxy;
R$_4$ represents hydrogen or a methoxy;

$R_5$ represents 2-pyridyl, 3-pyridyl, 4-pyridyl, 2-pyrimidinyl, 2-pyrazinyl, 3-pyridazinyl or 1,3-thiazol-2-yl;

$R_6$ is in position -2 of the phenyl and represents methoxy; and $R_7$ represents methoxy.

3. A compound chosen from:

5-chloro-3-(2-ethoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one;

5-chloro-3-(2-isopropoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one;

5-chloro-1-[(2,4-dimethoxyphenyl)sulphonyl]-3-(2-methoxyphenyl)-2-oxo-2,3-dihydro-1H-indol-3-yl 4-(2-pyridyl)-1-piperazinecarboxylate;

5-chloro-1-[(2,4-dimethoxyphenyl)sulphonyl]-3-(2-isopropoxyphenyl)-2-oxo-2,3-dihydro-1H-indol-3-yl 4-(4-pyridyl)-1-piperazinecarboxylate;

N-[5-chloro-1-[(2,4-dimethoxyphenyl)sulphonyl]-3-(2-methoxyphenyl)-2-oxo-2,3-dihydro-1H-indol-3-yl]-4-(4-pyridyl)homopiperazine-1-carboxamide;

N-[5-chloro-1-[(2,4-dimethoxyphenyl)sulphonyl]-3-(2-isopropoxyphenyl)-2-oxo-2,3-dihydro-1H-indol-3-yl]-4-(3-pyridyl)piperazine-1-carboxamide;

N-[5-chloro-1-[(2,4-dimethoxyphenyl)sulphonyl]-3-(2-isopropoxyphenyl)-2-oxo-2,3-dihydro-1H-indol-3-yl]-4-(4-pyridyl)piperazine-1-carboxamide;

5-chloro-1-[(2,4-dimethoxyphenyl)sulphonyl]-3-(2-methoxyphenyl)-3-[[3-oxo-3-[4-(2-pyridyl)-1-piperazinyl]propyl]amino]-1,3-dihydro-2H-indol-2-one;

5,6-dichloro-1-[(2,4-dimethoxyphenyl)sulphonyl]-3-(2-methoxyphenyl)-3-[2-oxo-2-[4-(4-pyridyl)-1-piperazinyl]ethyl]-1,3-dihydro-2H-indol-2-one;

5-chloro-1-[(2,4-dimethoxyphenyl)sulphonyl]-3-(2-methoxyphenyl)-6-methyl-3-[2-oxo-2-[4-(4-pyridyl)-1-piperazinyl]ethyl]-1,3-dihydro-2H-indol-2-one;

5-chloro-1-[(2,4-dimethoxyphenyl)sulphonyl]-3-(2-methoxyphenyl)-6-methyl-2-oxo-2,3-dihydro-1H-indol-3-yl 4-(4-pyridyl)-1-piperazinecarboxylate;

5-chloro-1-[(2,4-dimethoxyphenyl)sulphonyl]-6-methoxy-3-(2-methoxyphenyl)-2-oxo-2,3-dihydro-1H-indol-3-yl 4-(4-pyridyl)-1-piperazinecarboxylate;

N-[5-chloro-3-(2-chlorophenyl)-1-[(2,4-dimethoxyphenyl)sulphonyl]-2-oxo-2,3-dihydro-1H-indol-3-yl]-4-(2-pyridyl)piperazine-1-carboxamide;

N-[5-chloro-1-[(2,4-dimethoxyphenyl)sulphonyl]-3-(2-methoxyphenyl)-6-methyl-2-oxo-2,3-dihydro-1H-indol-3-yl]-4-(4-pyridyl)piperazine-1-carboxamide;

N-[6-chloro-3-(2-chlorophenyl)-1-[(2,4-dimethoxyphenyl)sulphonyl]-5-methyl-2-oxo-2,3-dihydro-1H-indol-3-yl]-4-(4-pyridyl)piperazine-1-carboxamide;

5-chloro-1-[(2,4-dimethoxyphenyl)sulphonyl]-3-(2-fluorophenyl)-3-[2-oxo-2-[4-(4-pyridyl)-1-piperazinyl]ethyl]-1,3-dihydro-2H-indol-2-one;

5,6-dichloro-1-[(2,4-dimethoxyphenyl)sulphonyl]-3-(2-fluorophenyl)-3-[2-oxo-2-[4-(4-pyridyl)-1-piperazinyl]ethyl]-1,3-dihydro-2H-indol-2-one;

5-chloro-3-(2,3-dimethoxyphenyl)-1-[(2,4-dimethoxyphenyl)sulphonyl]-3-[2-oxo-2-[4-(4-pyridyl)-1-piperazinyl]ethyl]-1,3-dihydro-2H-indol-2-one;

5-chloro-1-[(2,4-dimethoxyphenyl)sulphonyl]-3-(2-ethoxyphenyl)-3-[2-oxo-2-[4-(3-pyridyl)-1-piperazinyl]ethyl]-1,3-dihydro-2H-indol-2-one;

5-chloro-1-[(2,4-dimethoxyphenyl)sulphonyl]-3-(2-isopropoxyphenyl)-3-[2-oxo-2-[4-(3-pyridyl)-1-piperazinyl]ethyl]-1,3-dihydro-2H-indol-2-one;

5-chloro-1-[(2,4-dimethoxyphenyl)sulphonyl]-3-(2-isopropoxyphenyl)-3-[2-oxo-2-[4-(4-pyridyl)-1-homopiperazine]ethyl]-1,3-dihydro-2H-indol-2-one;

5-chloro-1-[(2,4-dimethoxyphenyl)sulphonyl]-3-(2-isopropoxyphenyl)-3-[2-oxo-2-[4-(1,3-thiazol-2-yl)-1-piperazinyl]ethyl]-1,3-dihydro-2H-indol-2-one;

5-chloro-1-[(2,4-dimethoxyphenyl)sulphonyl]-3-(2-ethoxyphenyl)-2-oxo-2,3-dihydro-1H-indol-3-yl 4-(3-pyridyl)-1-piperazinecarboxylate; and 5-chloro-1-[(2,4-dimethoxyphenyl)sulphonyl]-3-(2-ethoxyphenyl)-2-oxo-2,3-dihydro-1H-indol-3-yl 4-(4-pyridyl)-1-piperazinecarboxylate or a salt or hydrate thereof.

4. A process for preparing a compound according to claim 1, wherein:

a compound of formula:

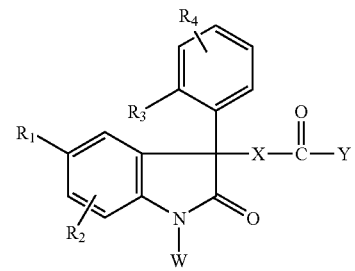

in which $R_1$, $R_2$, $R_3$, $R_4$ and X are as defined in claim 1, and:

Y represents hydroxyl or chlorine when X represents —$CH_2$—; —$OCH_2$—; —NH—$CH_2$—; or —NH—$CH_2$—$CH_2$—;

or Y represents phenoxy when X represents —O—; or —NH—;

W represents hydrogen when X represents —$CH_2$—; or —$OCH_2$—;

or W represents

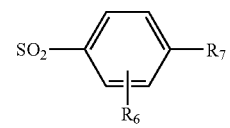

in which $R_6$ and $R_7$ are as defined in claim 1 when X represents —O—; —NH—; —NH—$CH_2$—; or —NH—$CH_2$—$CH_2$—;

is reacted with a compound of formula (III):

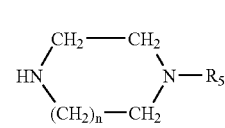

in which n and $R_5$ are as defined in claim 1;

when W represents

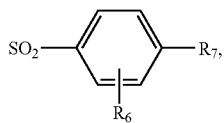

the corresponding compound of formula (I) is produced; or, when W represents hydrogen, the compound thus obtained of formula (IV):

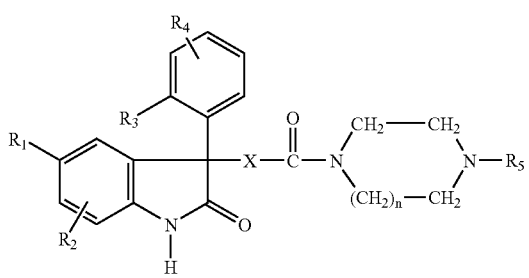

(IV)

is reacted, in the presence of a base, with a sulphonyl halide of formula (V):

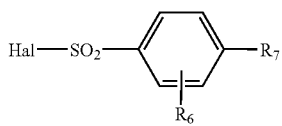

(V)

in which $R_6$ and $R_7$ are as defined in claim 1 and Hal represents a halogen atom to give the corresponding compound of formula (I).

5. A compound of formula (IV):

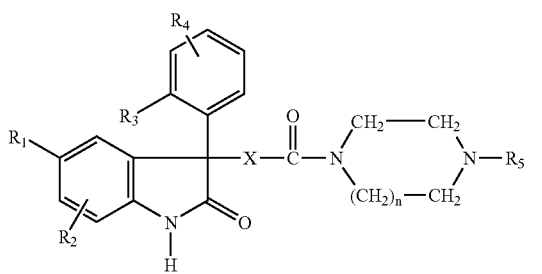

(IV)

in which:
n is 1 or 2;
X represents —CH$_2$—; or —O—CH$_2$—;
$R_1$ represents halogen; (C$_1$–C$_4$)alkyl; or (C$_1$–C$_4$)alkoxy;
$R_2$ represents hydrogen; halogen; (C$_1$–C$_4$)alkyl; (C$_1$–C$_4$)alkoxy; or trifluoromethyl;
$R_3$ represents halogen; (C$_1$–C$_3$)alkyl; (C$_1$–C$_3$)alkoxy; trifluoromethyl; or trifluoromethoxy;
$R_4$ represents hydrogen; halogen; (C$_1$–C$_3$)alkyl; (C$_1$–C$_3$)alkoxy;

$R_5$ is chosen from:

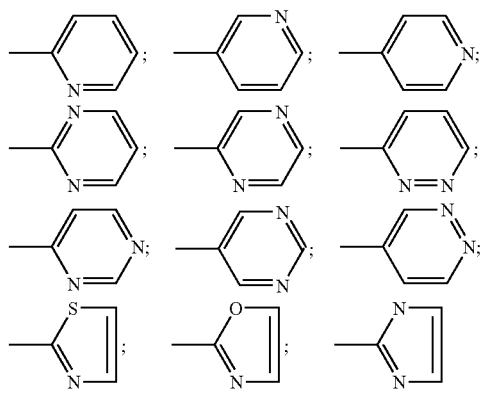

or a salt thereof.

6. A pharmaceutical composition comprising a compound according to claim 1 and one or more pharmaceutically acceptable excipients.

7. A compound according to claim 1 wherein:
$R_1$ is chlorine or methyl;
$R_2$ is hydrogen or is in position –4 or –6 of the indol-2-one and is chlorine, methyl, methoxy or trifluoromethyl;
$R_3$ is chlorine, fluorine, methoxy, ethoxy, isopropoxy, trifluoromethyl or trifluoromethoxy;
$R_4$ is hydrogen or methoxy;
$R_5$ is 2-pyridyl, 3-pyridyl, 4-pyridyl, 2-pyrimidinyl, 2-pyrazinyl, 3-pyridazinyl or 1,3-thiazol-2-yl;
$R_6$ is in position –2 of the phenyl and is methoxy; and
$R_7$ is methoxy.

8. A compound according to claim 1 wherein:
is 1 or 2;
X is —CH$_2$—, —O— or —NH—;
$R_1$ is chlorine;
$R_2$ is hydrogen;
$R_3$ is methoxy, ethoxy or isopropoxy;
$R_4$ is hydrogen;
$R_5$ is:

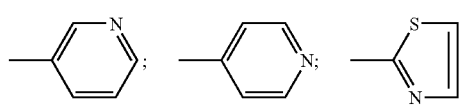

$R_6$ is in position –2 of the phenyl and is methoxy;
$R_7$ is methoxy.

9. A compound according to claim 1 wherein:
n is 1;
X is —CH$_2$—, —O— or —NH—;
$R_1$ is chlorine or methyl;
$R_2$ is hydrogen or is in position –4 or –6 of the indol-2-one and is chlorine, methyl or methoxy;
$R_3$ is chlorine, fluorine or methoxy;
$R_4$ is hydrogen;
$R_5$ is

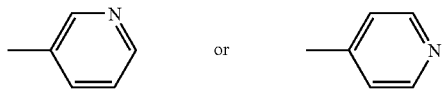

$R_6$ is in position −2 of the phenyl and is methoxy; and
$R_7$ is methoxy.

10. A compound according to claim 1 wherein:
n is 1;
X is —O—, —NH— or —NH—CH$_2$—CH$_2$—;
$R_1$ is chlorine;
$R_2$ is hydrogen;
$R_3$ is chlorine or methoxy;
$R_4$ is hydrogen;
$R_5$ is

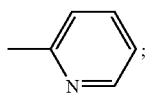

$R_6$ is in position −2 of the phenyl and is methoxy; and
$R_7$ is methoxy.

11. A pharmaceutical composition comprising a compound according to claim 2 and one or more pharmaceutically acceptable excipients.

12. A pharmaceutical composition comprising a compound according to claim 3 and one or more pharmaceutically acceptable excipients.

13. A pharmaceutical composition comprising a compound according to claim 7 and one or more pharmaceutically acceptable excipients.

14. A pharmaceutical composition comprising a compound according to claim 8 and one or more pharmaceutically acceptable excipients.

15. A pharmaceutical composition comprising a compound according to claim 8 and one or more pharmaceutically acceptable excipients.

16. A pharmaceutical composition comprising a compound according to claim 10 and one or more pharmaceutically acceptable excipients.

17. A method for the treatment of hypertension, pulmonary hypertension, Raynaud's disease, stress, anxiety, depression, obsessive-compulsive disorder, panic attacks, atherosclerosis, dysmenorrhoea, or premature labor, which comprises administering to a patient in need of such treatment a therapeutically effective amount of a compound according to claim 1.

18. A method for the treatment of hypertension, pulmonary hypertension, Raynaud's disease, stress, anxiety, depression, obsessive-compulsive disorder, panic attacks, atherosclerosis, dysmenorrhoea, or premature labor, which comprises administering to a patient in need of such treatment a therapeutically effective amount of a compound according to claim 2.

19. A method for the treatment of hypertension, pulmonary hypertension, Raynaud's disease, stress, anxiety, depression, obsessive-compulsive disorder, panic attacks, atherosclerosis, dysmenorrhoea, or premature labor, which comprises administering to a patient in need of such treatment a therapeutically effective amount of a compound according to claim 3.

20. A method according to claim 17 for the treatment of anxiety or depression.

21. A method according to claim 18 for the treatment of anxiety or depression.

22. A method according to claim 19 for the treatment of anxiety or depression.

23. A method for the treatment of anxiety or depression which comprises administering to a patient in need of such treatment a therapeutically effective amount of a compound according to claim 7.

24. A method for the treatment of anxiety or depression which comprises administering to a patient in need of such treatment a therapeutically effective amount of a compound according to claim 8.

25. A method for the treatment of anxiety or depression which comprises administering to a patient in need of such treatment a therapeutically effective amount of a compound according to claim 9.

26. A method for the treatment of anxiety or depression which comprises administering to a patient in need of such treatment a therapeutically effective amount of a compound according to claim 10.

* * * * *